(12) United States Patent
Hussain

(10) Patent No.: US 10,806,427 B2
(45) Date of Patent: Oct. 20, 2020

(54) SYSTEMS, DEVICES, AND METHODS FOR CAPTURING AND OUTPUTTING DATA REGARDING A BODILY CHARACTERISTIC

(71) Applicant: M3DICINE IP PTY LTD, Eight Mile Plains (AU)

(72) Inventor: Arsil Nayyar Hussain, Eight Mile Plains (AU)

(73) Assignee: M3DICINE IP PTY LTD, Brisbane (AU)

( * ) Notice: Subject to any disclaimer, the term of this patent is extended or adjusted under 35 U.S.C. 154(b) by 0 days.

(21) Appl. No.: 16/705,797

(22) Filed: Dec. 6, 2019

(65) Prior Publication Data

US 2020/0107808 A1 Apr. 9, 2020

Related U.S. Application Data

(63) Continuation of application No. 16/351,146, filed on Mar. 12, 2019, which is a continuation of application No. 14/882,921, filed on Oct. 14, 2015, now Pat. No. 10,265,043.

(60) Provisional application No. 62/210,558, filed on Aug. 27, 2015.

(30) Foreign Application Priority Data

Oct. 14, 2014 (AU) ................................ 2014904100
Nov. 24, 2014 (AU) ................................ 2014904742

(51) Int. Cl.
*A61B 7/04* (2006.01)
*A61B 5/0402* (2006.01)
*A61B 5/1455* (2006.01)

(52) U.S. Cl.
CPC .............. *A61B 7/04* (2013.01); *A61B 5/0402* (2013.01); *A61B 5/14551* (2013.01)

(58) Field of Classification Search
None
See application file for complete search history.

(56) References Cited

U.S. PATENT DOCUMENTS

| | | | |
|---|---|---|---|
| 4,129,125 A | 12/1978 | Lester et al. |
| 4,170,717 A | 10/1979 | Walshe |
| 4,377,727 A | 3/1983 | Schwalbach |
| 4,713,801 A | 12/1987 | Hale |
| 5,218,969 A | 6/1993 | Bredesen et al. |
| 5,636,041 A | 6/1997 | Pearce et al. |
| 5,638,453 A | 6/1997 | McLaughlin |
| 5,825,895 A | 10/1998 | Grasfield et al. |

(Continued)

*Primary Examiner* — Paul W Huber
(74) *Attorney, Agent, or Firm* — Saul Ewing Arnstein & Lehr LLP

(57) ABSTRACT

Systems, devices, and methods are provided for capturing and outputting data regarding a bodily characteristic. In one embodiment, a hardware device can operate as a stethoscope with sensors to detect bodily characteristics such as heart sounds, lung sounds, abdominal sounds, and other bodily sounds and other characteristics such as temperature and ultrasound. The stethoscope can be configured to work independently with built solid state memory or SIM card. The stethoscope can be configured to pair via a wireless communication protocol with one or more electronic devices, and upon pairing with the electronic device(s), can be registered in a network resident in the cloud and can thereby create a network of users of like stethoscopes.

25 Claims, 85 Drawing Sheets

(56) References Cited

U.S. PATENT DOCUMENTS

| | | | |
|---|---|---|---|
| 6,026,170 A | 2/2000 | Dieken et al. | |
| 7,300,406 B2 | 11/2007 | Carter | |
| 7,346,174 B1 | 3/2008 | Smith | |
| 8,696,587 B1 | 4/2014 | Whitfield | |
| 9,595,402 B2 | 3/2017 | Vansickle et al. | |
| 2001/0030077 A1 | 10/2001 | Watson | |
| 2002/0170193 A1 | 11/2002 | Townsend et al. | |
| 2002/0186850 A1 | 12/2002 | Deslauriers et al. | |
| 2005/0001821 A1 | 1/2005 | Low | |
| 2005/0113650 A1 | 5/2005 | Pacione et al. | |
| 2005/0119585 A1 | 6/2005 | Watrous | |
| 2006/0074321 A1 | 4/2006 | Kouchi et al. | |
| 2007/0004969 A1* | 1/2007 | Kong | A61B 5/0205 600/300 |
| 2007/0016091 A1 | 1/2007 | Butt et al. | |
| 2007/0106179 A1* | 5/2007 | Bagha | A61B 7/04 600/586 |
| 2008/0123472 A1 | 5/2008 | Bart | |
| 2008/0234594 A1 | 9/2008 | Brooks et al. | |
| 2008/0245602 A1 | 10/2008 | Nakamura | |
| 2008/0294019 A1 | 11/2008 | Tran | |
| 2009/0097623 A1* | 4/2009 | Bharadwaj | A61B 5/0002 379/106.02 |
| 2011/0245633 A1* | 10/2011 | Goldberg | A61B 5/681 600/301 |
| 2012/0041767 A1 | 2/2012 | Hoffman et al. | |
| 2013/0116513 A1* | 5/2013 | Smith | A61B 7/026 600/301 |
| 2013/0116584 A1 | 5/2013 | Kapoor | |
| 2014/0073486 A1 | 3/2014 | Ahmed et al. | |
| 2014/0155762 A1 | 6/2014 | Maskara et al. | |
| 2014/0201627 A1 | 7/2014 | Freeman et al. | |
| 2014/0235980 A1 | 8/2014 | Whitfield | |
| 2014/0245784 A1* | 9/2014 | Proud | A44C 5/0015 63/1.11 |
| 2014/0275824 A1* | 9/2014 | Couse | G16H 40/60 600/301 |
| 2014/0276133 A1 | 9/2014 | Schriefl et al. | |
| 2014/0278139 A1* | 9/2014 | Hong | A61B 5/7235 702/19 |
| 2014/0296658 A1 | 10/2014 | Yuen et al. | |
| 2015/0012877 A1 | 1/2015 | Lee et al. | |
| 2015/0126878 A1* | 5/2015 | An | A61B 5/7275 600/484 |
| 2015/0148618 A1* | 5/2015 | Sitko | A61B 5/7475 600/301 |
| 2015/0201272 A1 | 7/2015 | Wong | |
| 2015/0272511 A1 | 10/2015 | Najafi et al. | |
| 2015/0294440 A1 | 10/2015 | Roberts | |
| 2015/0297105 A1 | 10/2015 | Pahlevan et al. | |
| 2015/0297171 A1 | 10/2015 | Thiagarajan | |
| 2015/0327775 A1 | 11/2015 | Carter | |
| 2015/0327776 A1 | 11/2015 | Zhang et al. | |
| 2015/0359471 A1 | 12/2015 | Sperry | |
| 2015/0382147 A1 | 12/2015 | Clark et al. | |

* cited by examiner

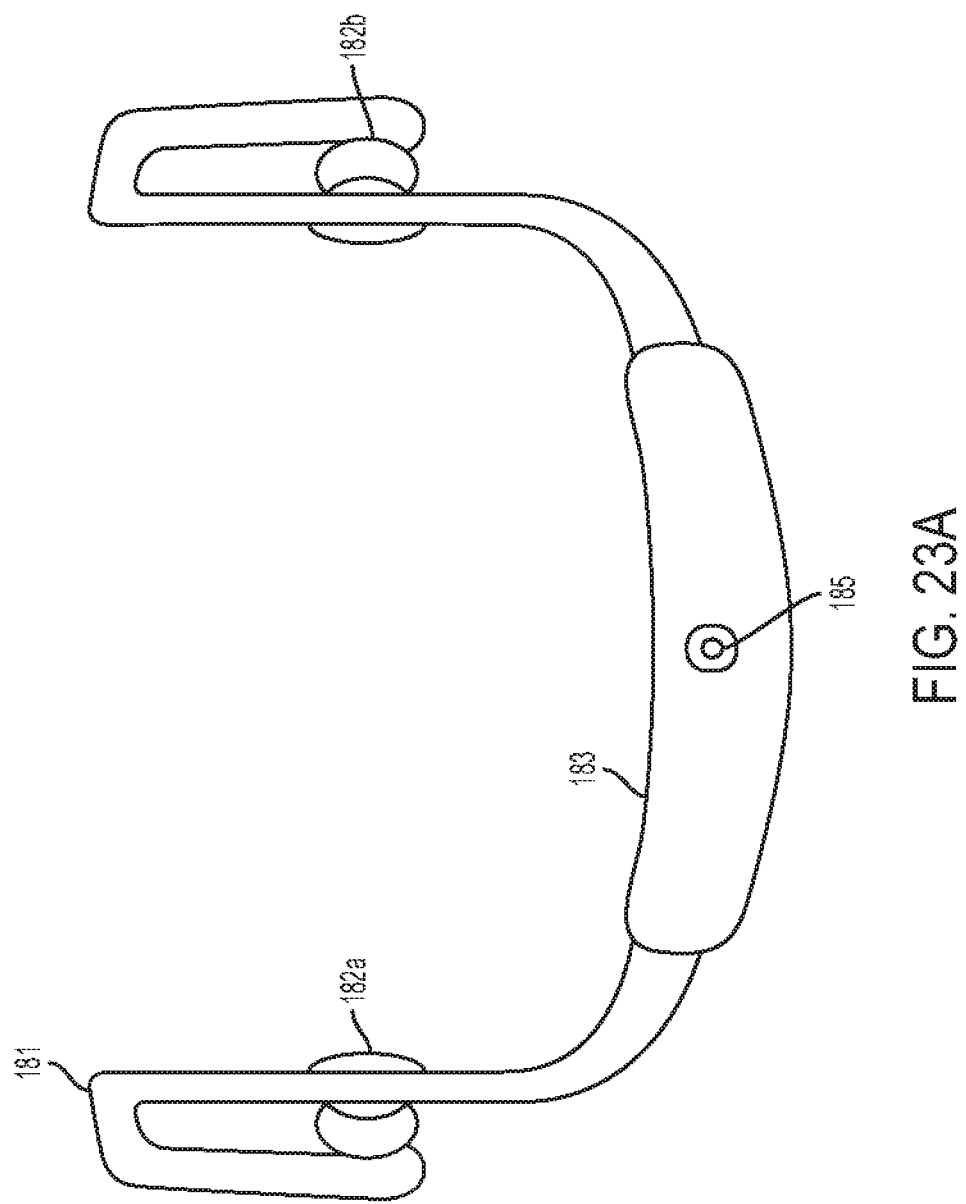

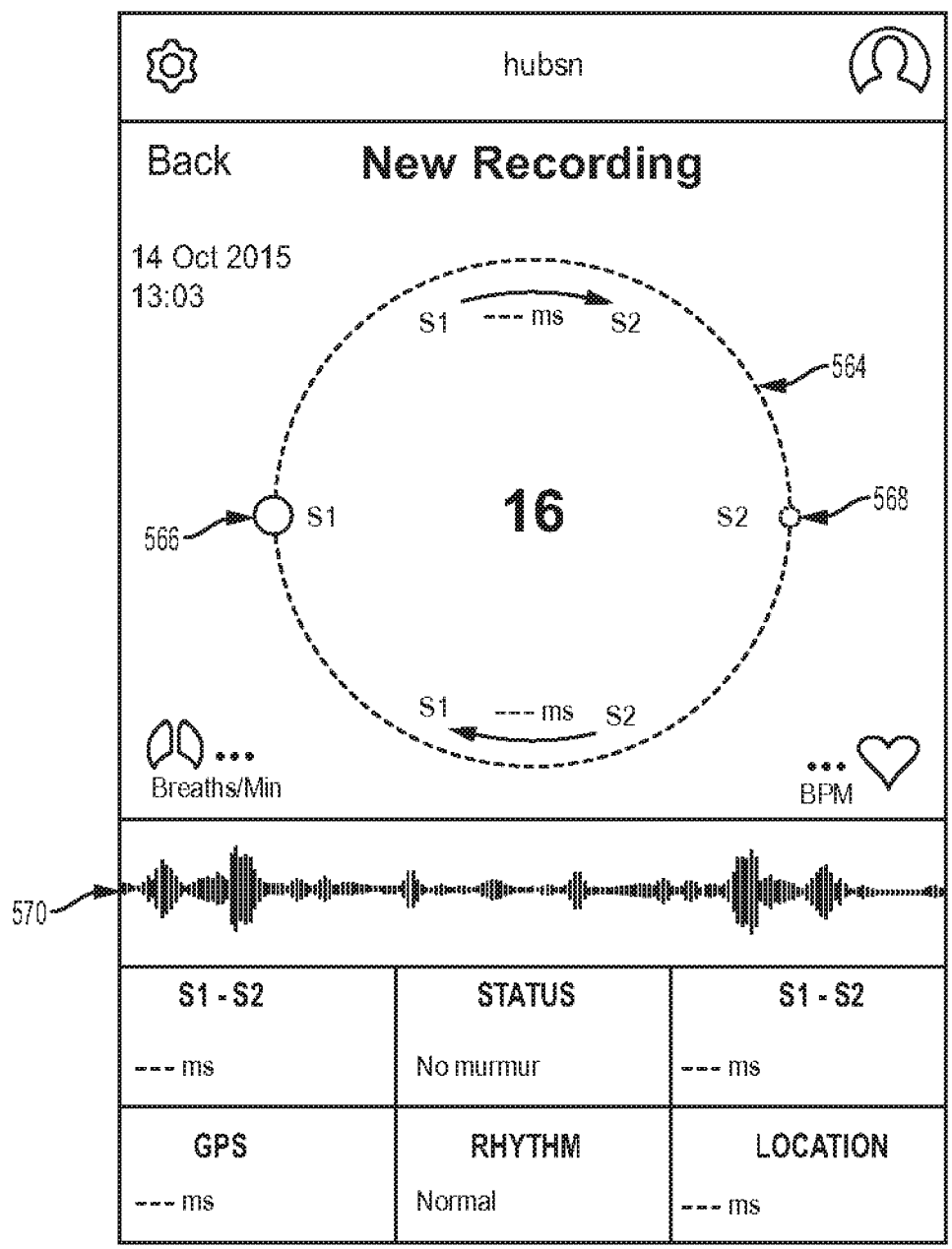
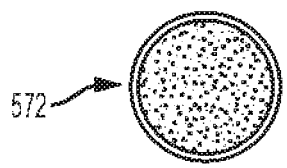
FIG. 84

SYSTEMS, DEVICES, AND METHODS FOR CAPTURING AND OUTPUTTING DATA REGARDING A BODILY CHARACTERISTIC

CROSS REFERENCE TO RELATED APPLICATIONS

This application is a continuation of U.S. patent application Ser. No. 16/351,146, filed Mar. 12, 2019, which is a continuation of U.S. patent application Ser. No. 14/882,921 entitled "Systems, Devices, and Methods for Capturing and Outputting Data Regarding a Bodily Characteristic" filed on Oct. 14, 2015, which claims priority to Australian Provisional Application No. 2014904100 entitled "Stethoscope" filed Oct. 14, 2014, to Australian Provisional Application No. 2014904742 entitled "Systems and Methods for Capturing Data, for Processing the Same and Delivering Output Representative of Body Sounds, Other Characteristics and Conditions" filed Nov. 24, 2014, and to U.S. Provisional Application No. 62/210,558 entitled "Systems and Methods for Capturing Data, for Processing the Same and Delivering Output Representative of Body Sounds, Other Characteristics and Conditions" filed Aug. 27, 2015, which are hereby incorporated by reference in their entireties.

FIELD OF THE INVENTION

The present disclosure relates generally to systems, devices, and methods for capturing and outputting data regarding a bodily characteristic.

BACKGROUND OF THE INVENTION

A conventional stethoscope is an acoustical device for auscultation or listening to internal sounds of a body. Conventional acoustical stethoscopes are often used to listen to lung and heart sounds as well as intestinal sounds and blood flow in arteries and veins. A conventional acoustical stethoscope typically has a chest piece which may be a diaphragm or plastic disc, or alternatively a bell or hollow cup. The chest piece is typically attached to air-filled hollow tubing that can form a pair of tubes which each have ear pieces for engagement with each ear of a general practitioner (GP) or other medical specialist. The bell transmits low frequency sounds while the diaphragm transmits higher frequency sounds. Using a conventional acoustical stethoscope, it can be difficult for a medical specialist to hear the internal sounds of a body due to any one or more issues such as low sound levels, a medical specialist's hearing deficiency, and/or ambient or background noise in the room or other location in which the conventional acoustical stethoscope is being used.

Some conventional stethoscopes are electronic and attempt to overcome the low sound levels of conventional acoustical stethoscopes by electronically amplifying body sounds. A conventional electronic stethoscope can be a wireless device, can be a recording device, and can provide noise reduction, signal enhancement, visual output, and audio output. Digitalization of heart sounds from conventional electronic stethoscopes has allowed collected heart sound data to be analysed, allowed graphic representations of cardiologic and pulmonologic sounds to be generated and transmitted for purposes of telemedicine (remote diagnosis) and teaching. Some conventional electronic stethoscopes feature audio output that can be used with an external recording device, such as a laptop or an MP3 recorder. Conventional electronic stethoscopes are typically complicated in structure, which makes manufacturing difficult, makes manufacturing expensive, results in an expensive device, and/or results in a device difficult for a user to learn how to use. Conventional electronic stethoscopes also use tubing. The tubing of conventional acoustical stethoscopes and of conventional electronic stethoscopes require medical specialists to be in close proximity to the subject on which the stethoscope is being used, which raises any one or more issues such as being disadvantageous for the control of infection, placing the medical specialist in harm's way in cases where the subject is unpredictable or dangerous (e.g., in the case of certain animals), and/or making the subject nervous due to close proximity and/or unfamiliarity (e.g., in the case of children who are comfortable only with daily caregivers or in the case of zoo animals who are most comfortable with certain zookeepers).

Listening to a conventional stethoscope requires a user to be highly trained and develop an expertise of detecting subtle sounds and nuances in the audio signal hear through the tubing. Medical professionals are taught the science of auscultation during medical school. Thus, use of conventional stethoscopes to listen to the sounds limits the use and understanding of the use of stethoscopes to medical professionals.

Accordingly, a need exists for improved systems, devices, and methods for capturing and outputting data regarding a bodily characteristic.

SUMMARY OF THE INVENTION

Systems, devices, and methods for capturing and outputting data regarding a bodily characteristic are provided.

In one aspect, a medical device is provided that in one embodiment includes a stethoscope that includes an audio sensor configured to sense body sounds of a subject from outside the subject's body, a vibration generator configured to vibrate, a light configured to illuminate, and a processor configured to cause the vibration generator to vibrate in a pattern indicative of the sensed body sounds in real time with the sensing of the body sounds, and configured to cause the light to illuminate in a pattern indicative of the sensed body sounds in real time with the sensing of the body sounds.

The medical device can have any number of variations. For example, the stethoscope can include a network interface configured to electronically communicate with an electronic device that is external to the stethoscope. The processor can be configured to cause data representing the sensed body sounds to the electronic device via the network interface in real time with the sensing of the body sounds.

For another example, the stethoscope can include an accelerometer and gyroscope, and the processor can be configured to cause the stethoscope to switch between an energy saving state and a normal energy consumption state based on movement of the stethoscope as sensed by the accelerometer and gyroscope. For yet another example, the body sounds can include heart sounds. For still another example, the body sounds can include lung sounds. For another example, the vibration can cause a sound to be emitted from the stethoscope such that the stethoscope is configured to simultaneously vibrate, illuminate, and emit sound. For yet another example, the stethoscope can include electrocardiogram (ECG) sensors, the processor can be configured to cause the vibration generator to vibrate in a pattern indicative of the data sensed by the ECG sensors in real time with the sensing of the data, and the processor can be configured to cause the light to illuminate in a pattern indicative of the data sensed by the ECG sensors in real time with the sensing of the data. For still another example, the stethoscope can include a wireless charging receiver configured to allow wireless charging of the stethoscope.

For another example, the stethoscope can include a base having a surface configured to contact the subject's body, a body having the processor contained therein, and a head. The head can be movable relative to the base and the body to selectively start the audio sensor sensing the body sounds and stop the audio sensor from sensing the body sounds. The head can be configured to rotate relative to the base and the body and is configured to move vertically relative to the base and the body. One of the rotation and the vertical motion can be configured to selectively start the audio sensor sensing the body sounds and stop the audio sensor from sensing the body sounds. The other of the rotation and the vertical motion can be configured to selectively turn network connectivity of the stethoscope on and off. The head can be configured to move relative to the base and the body to adjust a gain of the audio sensor.

In another aspect, a medical system is provided that in one embodiment includes a stethoscope and a display coupled to the stethoscope. The stethoscope includes a distal portion having a surface configured to contact a body of a subject, and a proximal head configured to move relative to the distal portion to selectively start a sensor sensing body sounds of the subject and stop the sensor from sensing the body sounds. The display is configured to show a graphical representation of the sensed body sounds in real time with the gathering of the signals.

The medical system can vary in any number of ways. For example, the display can be on the proximal head. The proximal head can be removably and replaceably coupled to the distal portion, or the proximal head can be non-removably coupled to the distal portion. The removable and replaceable proximal head can be configured to be removably and replaceably docked to a wearable electronic device following removal of the proximal head from the distal portion.

For another example, the display can be on an electronic device that is external to and separate from the stethoscope. For yet another example, the body sounds can include at least one of heart sounds and lung sounds. For still another example, the medical system can include a processor configured to cause the display to show the graphical representation in response to the sensing of the body sounds.

In another aspect, a method is provided that in one embodiment includes positioning the stethoscope on the patient's body, activating the audio sensor to begin the sensing of the body sounds and thereby begin causing the vibration generator to vibrate in the pattern indicative of the sensed body sounds in real time with the sensing of the body sounds and causing the light to illuminate in the pattern indicative of the sensed body sounds in real time with the sensing of the body sounds.

The method can have any number of variations. For example, the method can include transmitting data representing the sensed body sounds to an electronic device that is external to the stethoscope in real time with the sensing of the body sounds.

In another embodiment, a method is provided that includes receiving at a network-connected device data indicative of body sounds of a subject sensed by an electronic stethoscope in real time with the body sounds being sensed by the electronic stethoscope, and causing the network-connected device to provide an output detectable to a user of the network-connected device, the output being indicative of the received data. The output is provided in real time with the body sounds being sensed by the electronic stethoscope.

The method can vary in any number of ways. For example, providing the output can include displaying information indicative of the received data on a display of the network-connected device. For another example, providing the output can include at least one of the network-connected device vibrating, the network-connected device emitting audio, and a light of the network-connected device illuminating.

For yet another example, the electronic stethoscope can provide an output to a user of the electronic stethoscope indicative of the body sounds being sensed by the electronic stethoscope, and the output of the electronic stethoscope can include at least one of vibration of the electronic stethoscope and illumination of one or more lights on the electronic stethoscope. The output of the network-connected device can be the same as the output of the electronic stethoscope.

For still another example, the network-connected device can include a plurality of network-connected devices such that each of the plurality of network-connected devices provides real time output. For another example, the network-connected device can include an application downloaded thereto over a network, and the application can control the receiving of the data and the providing of the output. For yet another example, the network-connected device can include one of a phone, a headset, a watch, a tablet, a laptop computer, a desktop computer, and a server. For still another example, the network-connected device can include a second electronic stethoscope.

In another embodiment, a method is provided that includes electronically linking a first electronic stethoscope to a second electronic stethoscope, gathering at the first electronic stethoscope raw data signals representative of body sounds of a subject, and outputting at the first electronic stethoscope a first output that includes at least one of an audio output, a haptic output, and an illuminated output, the first output being indicative of the gathered signals. The outputting at the first electronic stethoscope occurs in real time with the gathering. The method also includes transmitting the gathered signals from the first electronic stethoscope to the second electronic stethoscope, and outputting at the second electronic stethoscope a second output that includes at least one of an audio output, a haptic output, and an illuminated output. The second output is indicative of the gathered signals, and the outputting at the second electronic stethoscope occurs in real time with the gathering.

The method can vary in any number of ways. For example, the first output can include at least two of the audio output, the haptic output, and the illuminated output. For another example, the first output can include all of the audio output, the haptic output, and the illuminated output. For yet another example, the body sounds can include at least one of heart sounds and lung sounds. For still another example, the second output can be identical to the first output. For another example, the method can include analyzing the gathered signals to determine whether a possible anomaly exists in the body sounds of the patient, and when it is determined that a possible anomaly exists, the first output can be indicative of the possible anomaly.

For yet another example, the method can include pairing the first electronic stethoscope to a first external electronic device. The first external electronic device can display on a first display thereof first information indicative of the gathered signals. The displaying on the first display can occur in real time with the gathering. The method can also include pairing the second electronic stethoscope to a second external electronic device. The second external electronic device can display on a second display thereof second information indicative of the gathered signals. The displaying on the second display can occur in real time with the gathering.

In another embodiment, a method is provided that includes gathering via an electronic stethoscope raw data signals representative of body sounds of a subject, and causing a display to show a graphical representation of the gathered signals in real time with the gathering of the signals. The graphical representation includes a track along which a marker traverses in sync with the gathered signals. The method also includes analyzing the gathered signals in real time with the gathering to determine whether a possible anomaly exists in the body sounds of the patient, and when it is determined that a possible anomaly exists, causing a mark to appear on the track at a position along the track corresponding to a time at which the possible anomaly exists, the mark being indicative of the possible anomaly.

The method can have any number of variations. For example, the display can be on the stethoscope. For another example, the display can be on an electronic device physically independent of and electronically linked to the stethoscope. For yet another example, the method can include outputting at the electronic stethoscope an output that includes at least one of an audio output, a haptic output, and an illuminated output, the output being indicative of the gathered signals, and the outputting at the electronic stethoscope can occur in real time with the gathering.

For another example, the body sounds can include heart sounds. A length of the track can correspond to one heart beat cycle. The mark can appear on the track at a time where the possible anomaly exists relative to a first heart sound (SI) and a second heart sound (S2) in the heart beat cycle.

For still another example, the body sounds can include lung sounds. A length of the track can correspond to one breath cycle. The mark can appear on the track at a time where the possible anomaly exists relative to a start of inspiration and a start of expiration in the breath cycle.

In another embodiment, a method includes gathering via an electronic stethoscope raw data signals representative of cardiac sounds of a subject, analyzing the gathered signals in real time with the gathering to determine a heart rate of the subject, and analyzing the determined heart rate in real time with the gathering to determine a breathing rate of the subject.

The method can vary in any number of ways. For example, the method can include causing a display to show a graphical representation of the determined breathing rate in real time with the gathering.

Non-transitory computer program products (i.e., physically embodied computer program products) are also provided that store instructions, which when executed by one or more processors of one or more computer systems, causes at least one processor to perform operations herein. Similarly, computer systems are also provided that can include one or more processors and one or more memories coupled to the one or more processors. Each of the one or more memories can temporarily or permanently store instructions that cause at least one processor to perform one or more of the operations described herein. In addition, methods can be implemented by one or more processors either within a single computer system or distributed among two or more computer systems. Such computer systems can be connected and can exchange data and/or commands or other instructions or the like via one or more connections, including but not limited to a connection over a network (e.g., the Internet, a wireless wide area network, a local area network, a wide area network, a wired network, etc.), via a direct connection between one or more of the multiple computer systems, etc.

BRIEF DESCRIPTION OF DRAWINGS

This invention will be more fully understood from the following detailed description taken in conjunction with the accompanying drawings, in which:

FIG. 23A is an end view of one embodiment of a Bluetooth headset;

FIG. 84 is a showing another embodiment of a recording detail screen; and

DETAILED DESCRIPTION OF THE INVENTION

Figure 1:
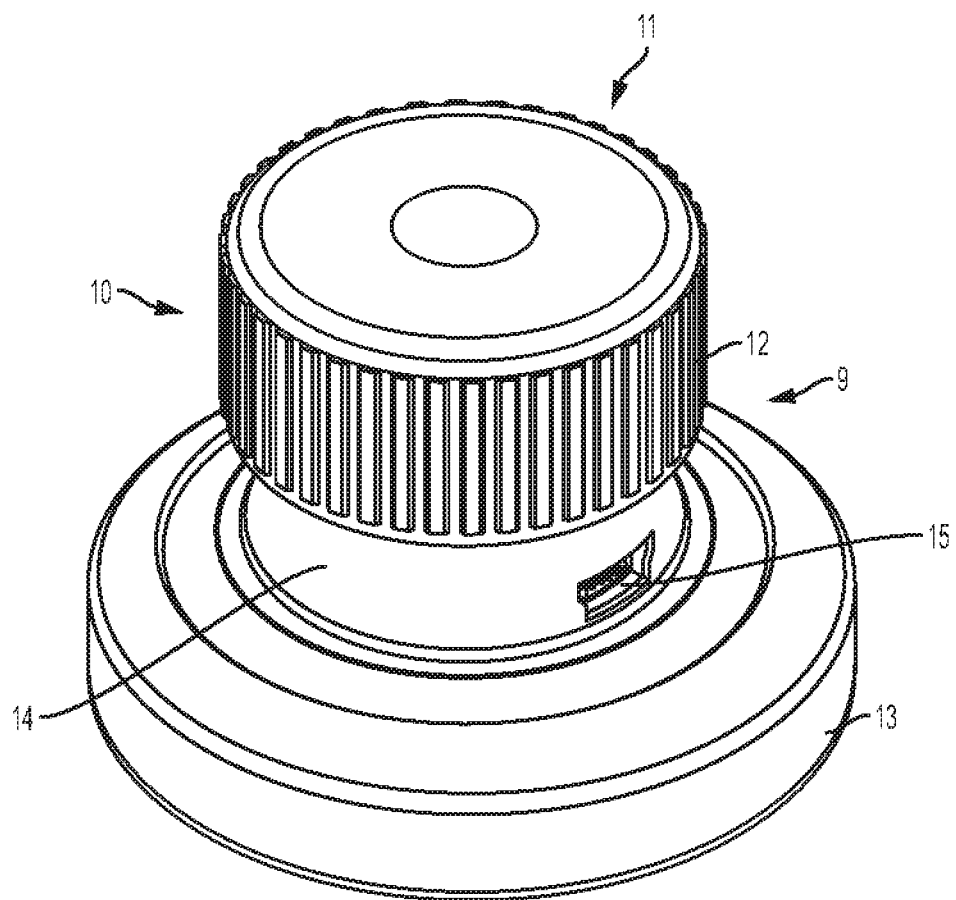
FIG. 1 is a perspective view of one embodiment of a stethoscope.

Certain exemplary embodiments will now be described to provide an overall understanding of the principles of the structure, function, manufacture, and use of the devices and methods described herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon.

Systems, devices, and methods are provided for capturing and outputting data regarding a bodily characteristic. In at least some embodiments, a hardware device can be configured to operate as a stethoscope with one or more sensors configured to detect bodily characteristics of a subject such as a heart sounds (e.g., heartbeat and other heart sounds), lung sounds, abdominal sounds, and other bodily sounds and other characteristics such as temperature and ultrasound. The stethoscope can be configured to work independently with built solid state memory or SIM card. The stethoscope can be configured to communicate with one or more electronic devices, such as a mobile device, a laptop, etc. Data collected by the stethoscope related to the bodily characteristics can be transmitted from the stethoscope to a diagnostic model. The output of the diagnostics model can provide a diagnosis and can provides a graphical user interface with an interpretation of the output. The stethoscope can be configured to pair via Bluetooth, Wi-Fi, or other wireless communication protocol with the one or more electronic devices, and upon pairing with the electronic device(s), can be registered in a network resident in the cloud and can thereby create a network of users of like stethoscopes.

The stethoscope can thus include a sensor design featuring integrated Bluetooth and integrated visual system that can allow a user of the stethoscope to hear through any Bluetooth wireless telephone, mobile, or other device and also to see through integrated lighting a visual representation of the detected bodily characteristics, e.g., a visual representation of heart beat and pulse, a visual representation of breathing rate, etc. The stethoscope thus need not rely on listening intensely by one GP or other medical specialist, unlike with conventional stethoscopes, and/or does not require tubing that limits the movement of the stethoscope's user and hence the stethoscope does not requires a user's close proximity to the subject, nor does it require user expertise to translate the audio to meaningful information, unlike with conventional stethoscopes.

The stethoscope can include a combination of auditory and visual auscultation and can be configured to provide analysis of the detected bodily characteristics, e.g., detected heart beat and pulse, etc. The stethoscope can have a multiple sync function configured to allow the stethoscope's gathered sound to be shared with multiple other devices, e.g., other stethoscopes or various types of electronic devices such as Bluetooth headsets and mobile phones. Thus, multiple people not using the stethoscopes, such as onlookers, family members of the subject, owners of pets, medical students, colleagues, etc. can receive the stethoscope's sound through the use of the other devices. Each of the other devices can have installed thereon an application (APP) that can be configured to store, transmit, analyze, and display the received sound information and present possible diagnosis on based thereon, e.g., based on received heartbeat and pulse information. Thus, people other than a user directly using the stethoscope can evaluate the subject's condition and make diagnosis and/or treatment decisions based at least in part of the stethoscope's gathered information. For example, in the case of a detected bodily characteristic including heart rate, the heartbeat can be averaged to present an approximate heart rate to the user and/or to the other multiple people. A series of colors provided via illuminated lights can be used to indicate a range of different heart rates and can thereby be used to easily detect heart rates outside an expected norm.

The stethoscope including a combination of auditory and visual auscultation and being configured to provide analysis of the detected bodily characteristics may allow any user, with or without medical training, to understand the detected bodily characteristics by translating gathered audio signals into a visual output (e.g., lights) and a haptic output (e.g., vibration). For example, with respect to detected cardiac sounds, the stethoscope can be configured to output light of a first color (e.g., green) to indicate normal heart conditions, to not vibrate when normal heart conditions are detected, to output light of a second, different color (e.g., orange) to indicate a detected possible anomaly such as a murmur, and to vibrate when a detected possible anomaly exists. For another example, with respect to detected lung sounds, the stethoscope can be configured to output light of a first color (e.g., green) to indicate normal breathing conditions, to not vibrate when normal breathing conditions are detected, to output light of a second, different color (e.g., orange) to indicate a detected possible anomaly such as wheezing, and to vibrate when a detected possible anomaly exists.

In at least some embodiments, the systems, devices, and methods for capturing and outputting data regarding a bodily characteristic can include capturing data, processing the same, and delivering output representative of body sounds. The systems, devices, and methods can include a stethoscope configured to pair to other devices to thus allow the sharing of immersive three-dimensional feedback experiences with one or more users in addition to a user of the stethoscope.

In at least some embodiments, the systems, devices, and methods for capturing and outputting data regarding a bodily characteristic can increase the accuracy of detection of heart sounds, murmurs, and other body sounds, there thus may achieve a reduction in unnecessary referrals and cardiac events. The systems, devices, and methods can provide a manner to track representative raw data and study the representative raw data over time. With available machine learning and predictive modeling and artificially intelligent search engines, clinical software and electronic health record (EHR) platforms, a stethoscope of the systems, devices, and methods can provide raw data and therefore representative raw data for analysis for diagnosis and tracking, sharing of information, teaching, as well as allow for a platform for a network of health care professionals so that the health care professionals can send and receive data as well as engage in written and oral and visual communication with one another in real time. A person skilled in the art will appreciate that "real time" may involve some minor time delay due to any one or more factors, such as network data transmission capability and minor limits to processor processing speed. Not only are health care professionals (for humans and for animals) capable of utilizing the stethoscope, but non-health care individuals (e.g., patients, family members of patients, pet owners, youth, etc.) may as well, with the representative data being transmitted via a network to one or more health care professionals at remote locations for evaluation.

In at least some embodiments, a stethoscope can be configured to search and connect to other similar stethoscopes located either locally or remotely. The stethoscope can be configured to provide an immersive three-dimensional feedback experiences with one or more users of the connected stethoscopes, thus allowing users to simultaneously hear, feel, and share the same detected body sounds, e.g., heartbeat, breathing, etc. In this way, the stethoscope may provide bedside teaching capability where students do not individually need to place their equipment on a patient. This may provide for less intrusion on patients and/or provide for better hygiene.

In at least some embodiments, a stethoscope and/or an electronic device to which the stethoscope transmits sensed data can be configured to compare previously recorded representative data and/or to compare that data to family data. The data can be utilized in studies, particularly since sensors of the stethoscope can acquire other data, such as ambient conditions and location data, as discussed herein. For athletes, for example, such functionality may be beneficial since the stethoscope can monitor heart valve performance, not just simple heart rate.

In at least some embodiments, a stethoscope can be configured to provide an immersive three-dimensional feedback experience for a user of the stethoscope as well as for remote users not directly using the stethoscope. When the stethoscope's one or more sensors are activated, for example, by pushing down on a head or knob of the stethoscope, so that the one or more sensors begin receiving input from a subject's body, the stethoscope can be configured to vibrate to the heart beat input, light up to the heart beat input, and transmit sound signals sensed by the one or more sensors to one or more headsets in real-time synchronization with the person's bodily sounds. When the stethoscope is paired to one or more other stethoscopes either directly, or via, for example, a mobile device, the other stethoscope(s) can be similarly configured provide the immersive three-dimensional feedback experience. The sensor data of the stethoscope can be transmitted in real-time via telecommunications to a remote location, for example, via a remote server in communication with the stethoscope for the same three-dimensional feedback experience at a different location.

In at least some embodiments, a stethoscope can be configured to pair to a headset, and at least one of a mobile device and a personal computer (PC). Either or both of the mobile device and PC can be in communication with a remote server, otherwise known as the cloud. The stethoscope can include memory configured to store data for later transmission for analysis, and/or on the mobile device and/or PC paired to the stethoscope, or to any other suitable device. The stethoscope can be configured for analytics as computing capability is available for such analytics.

In at least some embodiments, a stethoscope can be configured to receive raw data, including those of heart and lung sounds of a subject, via one or more sensors. The stethoscope can include sensors such as a gyroscope and accelerometer to provide the subject's position information that can be noted and/or recorded while the heart sound/lung sound sensors and/or other sensors are receiving signals for diagnosis. The subject's position while the data is taken may be useful in particular when comparing previously recorded data to later recorded data. The position of the subject, e.g., sitting up or lying down, may have an impact on the resultant data. The one or more sensors can be configured to sense any one or more of ECG signals, gyroscope signals, temperature signals, infrared signals, and ultrasound signals, as well as others. The signals can be processed so that a diagnosis may be presented. The diagnosis can be delivered, for example, via a graphical user interface on a display device of an electronic device such as a mobile device or PC.

In at least some embodiments, a headset can be configured to be paired to a stethoscope by wired connection or wireless connection. The headset can include a behind-the-neck configuration and can include light emitting diode (LED) indicators on earpieces of the headset that can sync to sounds (e.g., heart sounds, lung sounds, etc.) sensed by the paired stethoscope. The lights can indicate to colleagues or other nearby persons when the user of the headset is listening to sounds so that the user is not disturbed and/or can provide information to the colleagues or other nearby persons who may observe the synced lights. The headset can have an LED indicator housed in the behind-the-neck member that can serve to indicate to colleagues or other nearby persons when the user is listening to body sounds. The LED indicator can have at least two states of illumination. The illumination can be in a low state when the stethoscope is not in use, and can be in a high state when the stethoscope is in use. Any other color can be used for the LED indicator, as can any combination of colors to create indications.

In at least some embodiments, a stethoscope can be configured for use with or without a paired electronic device (mobile device, PC, etc.). A paired electronic device can be configured to provide analytics of data for representation. If a paired electronic device is not allowed to be used, for example in an operating room or on an airplane, if the paired electronic device must access a remote server to provide analytics, a PC or other computer system can instead be used for analytics. This disclosure is not intended to limit what type of device carries out analytical functions.

In at least some embodiments, a stethoscope can include controls to turn down or off features such as vibration and illumination sync to sensed body sounds. Audio frequency can be configured to be fine-tuned and enhanced to filter out unwanted noise to isolate desired sounds, either in real time or later, such as later via mobile app. The data collected by the stethoscope can be stored on the stethoscope, and at a later time, the data may be transmitted to an electronic device that can provide visual output of the data. In other words, the electronic device can provide output in real time with the stethoscope's sensing or not in real time but instead at a subsequent time.

Figure 2:
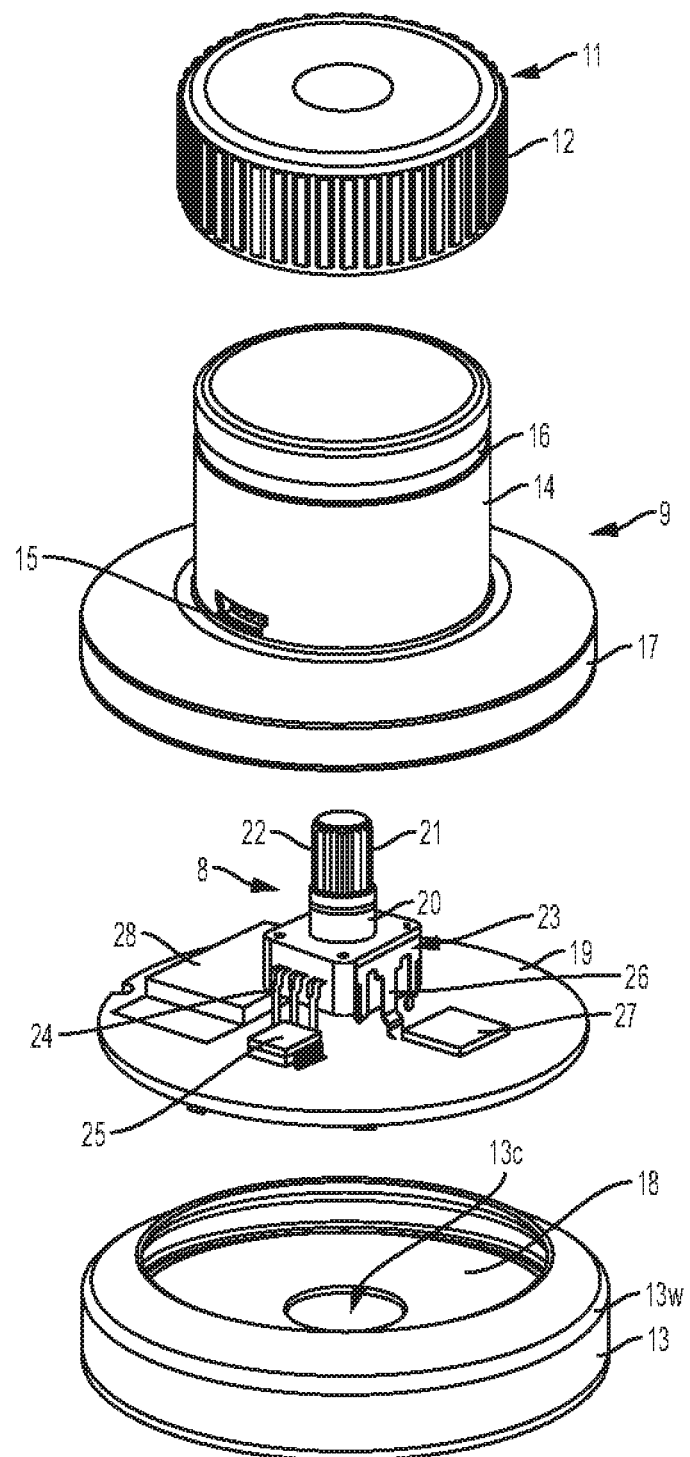
FIG. 2 is an exploded view of the stethoscope of FIG. 1.
Figure 5:
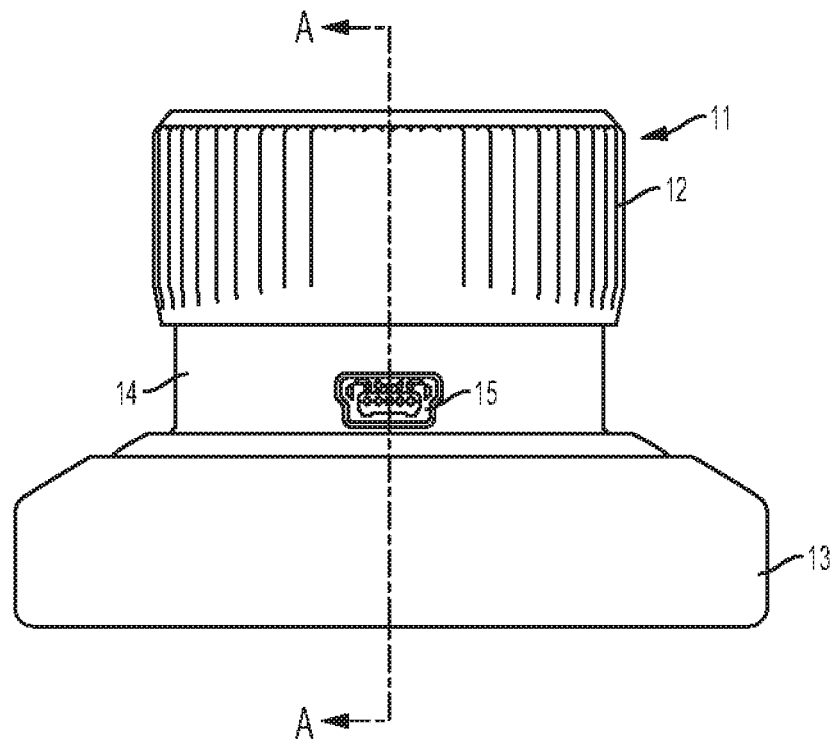
FIG. 5 is a side view of the stethoscope of FIG. 1.

FIGS. 1 and 2 illustrate one embodiment of a stethoscope 10. As in this illustrated embodiment, the stethoscope can include a knob 11 (also shown in FIGS. 5-7), a hollow body 9 (also shown in FIGS. 3, 5 and 6) having the knob 11 movably coupled to a proximal end thereof, a rotary potentiometer 8 (also shown in FIGS. 3, 4, 6, and 7) disposed in the hollow body 9 and the knob 11, and a base 13 (also shown in FIGS. 5 and 6) having a distal end of the hollow body 9 seated therein. The knob 11 can have a variety of configurations. As shown the knob 11 can include a gripping feature such as a plurality of milled edges 12 around a circumference thereof configured to provide traction when being gripped by a hand (not shown) of a user. Instead of or in addition to the plurality of milled edges 12, the knob 11 can include another type of gripping feature, such as one or more finger depressions, a tacky surface, etc.

The knob 11 can include a central boss 44 extending distally from a proximal inner surface thereof. The central boss 44 can have a bottom or distal cavity 45 formed therein configured to receive the rotary potentiometer 8 therein. The cavity 45 can include longitudinal splines 21A formed on an inner surface thereof.

The hollow body 9 can have a variety of configurations. As shown, the hollow body 9 can include a proximal upstanding body portion 14 configured to movably engage the knob 11 and a distal portion 17 configured to be seated in a hollow interior 18 of the base 13. The hollow body 9 can include a universal serial bus (USB) port 15, which may facilitate electronic connection of the stethoscope 10 to an electronic device such as a computer, a mini USB jack into a standard 3.5 mm headphone jack to allow any wired headphone set to be attached to the stethoscope 10, or a portable USB drive. Instead of or in addition to the USB port 15, the stethoscope 10 can have any one or more other types of wired data connection port, as will be appreciated by a person skilled in the art. As will also be appreciated by a person skilled in the art, in addition or in alternative to being configured to communicate via wired connection with another electronic device via the USB port 15 and/or other port, the stethoscope 10 can be configured to communicate wirelessly, such as via Bluetooth, with another electronic device.

The proximal portion 14 of the hollow body 9 can have a circular groove 16 (also referred to herein as an "annular recess" or "recess") formed in an exterior surface thereof. The annular recess 16 can be configured to engage a peripheral rib 45A formed on and extending radially outward from an inner surface of the rotatable knob 11 (see FIGS. 6 and 7). The recess 16 can be configured to retain the knob 11 in non-removable engagement with the hollow body 9. The rib 45A can be configured to slide within the recess 16 during rotation of the knob 11 about a longitudinal axis thereof, which is represented by line A-A in FIG. 5. The longitudinal axis of the knob 11 can, as shown, be the same as a longitudinal axis of the stethoscope 10 overall. The groove 16 can have a height B (FIG. 6) that is greater than a height of the rib 45A. The rib 45A can thus be configured to move vertically (e.g., proximally and distally) within the groove 16 at a maximum distance defined by the height B. The knob 11 can thus be configured to have two distinct ranges of motion relative to the hollow body 9, the rotation of the knob 11 being one range of motion and the vertical movement of the knob 11 being another range of motion. The knob 11 can be biased to a proximal position within the groove 16, e.g., the rib 45A can be biased to abut a proximal surface of the rib 45A. The knob 11 is shown in this biased, or default, position in FIGS. 6 and 7. The knob 11 can be so biased in a variety of ways, such as by being biased upwards or proximally by a bias element such as a spring disposed within the stethoscope 10, as discussed further below.

Figure 3:
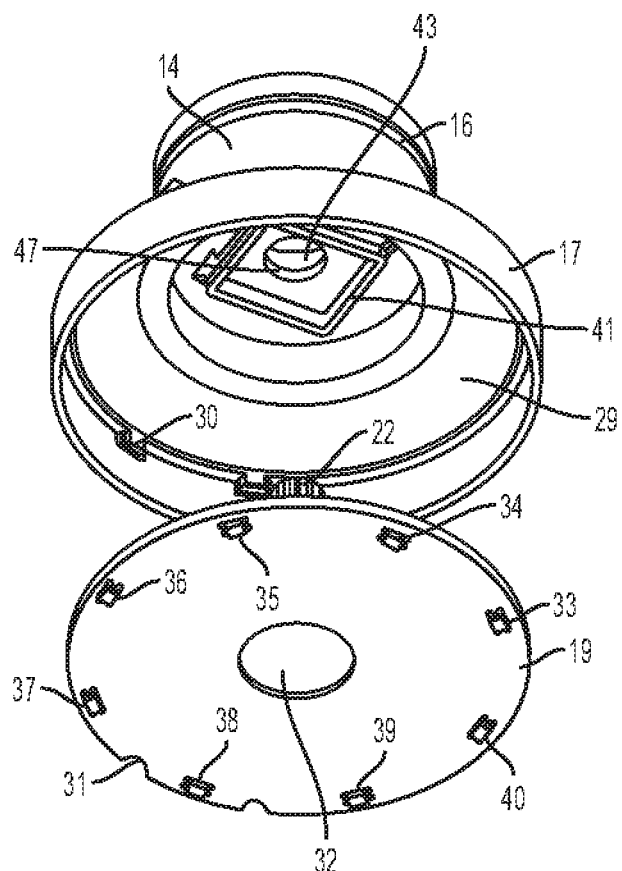
FIG. 3 is an exploded view of a hollow body, rotary potentiometer, and a circuit board of the stethoscope of FIG. 1.
Figure 4:
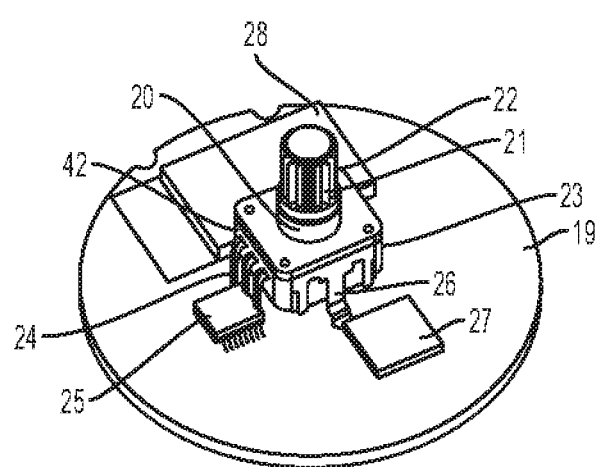
FIG. 4 is a perspective view of the circuit board and rotary potentiometer of FIG. 3.

As shown in FIG. 3, the distal portion of the hollow body 9 can have a hollow interior 29. One or more projections 30 can extend radially inward from an inner surface of the hollow body 9 in the hollow interior 29. The hollow body 9 includes two projections 30 in this illustrated embodiment. The one or more projections 30 can be configured to engage corresponding one or more recesses 31 formed in a perimeter of a circuit board 19 to facilitate secure seating of the circuit board 19 within the hollow body 9, e.g., within the hollow interior 29, and within the base 13, e.g., within the hollow interior 18.

Figure 6:
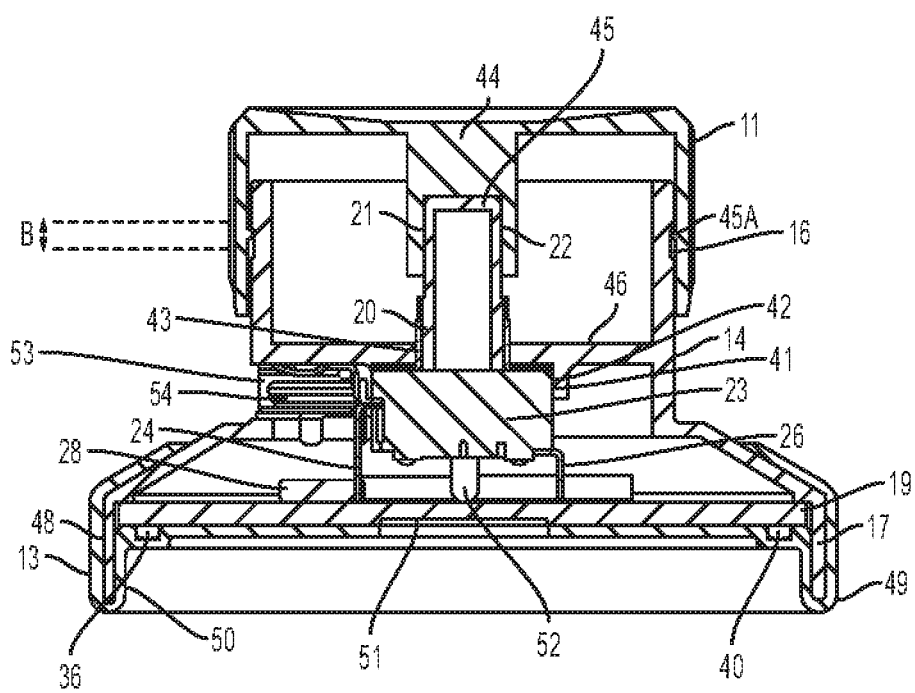
FIG. 6 is a cross-sectional view of the stethoscope of FIG. 5 along line A-A.
Figure 7:
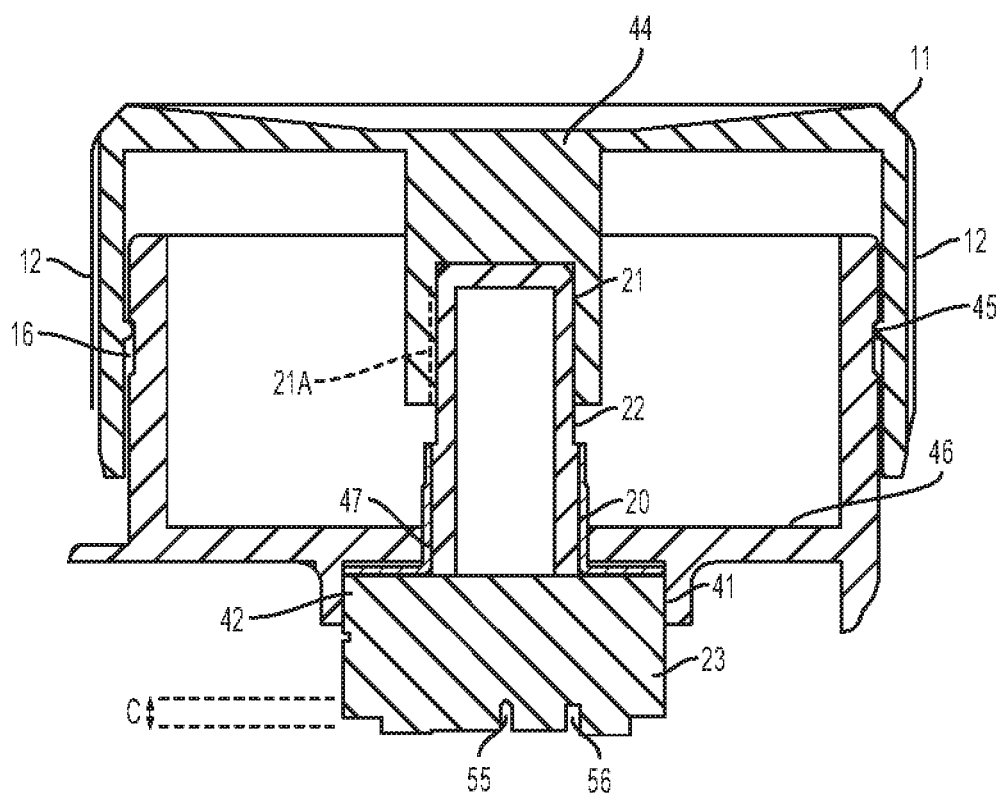
FIG. 7 is a zoomed-in view of a knob and the rotary potentiometer of the stethoscope of FIG. 6.

The hollow body 9 can include a hollow recess 41 proximal to the hollow interior 29. The hollow recess 41 can, as in this illustrated embodiment, have a rectangular shape. The hollow recess 41 can be configured to engage a top edge part 42 of the rotary potentiometer 8 (e.g., a lower or distal portion 23 thereof), as shown in FIG. 6. The hollow recess 41 can have a central opening 43 configured to engage with a connection post 22 of the rotary potentiometer 8, as also shown in FIG. 6. The central opening 43 can have a peripheral surface 47 that defines a perimeter of the central opening 43. The peripheral surface 47 can be configured to contact a bearing surface 20 of the rotary potentiometer 8. The hollow body 9 can include a transverse portion 46 integral with the hollow recess 41 and defining an upper end thereof.

The stethoscope 10 can include an on-board power source, which may facilitate portability of the stethoscope 10. The hollow body 9 can include a cavity 53 configured to seat the power source, such as a battery 54, therein. The battery 54 can be configured to be rechargeable, such as via power connection via the USB port 15, which may prolong the useful life of the stethoscope 10. In other embodiments, the battery 54 can be non-rechargeable.

Figure 8:
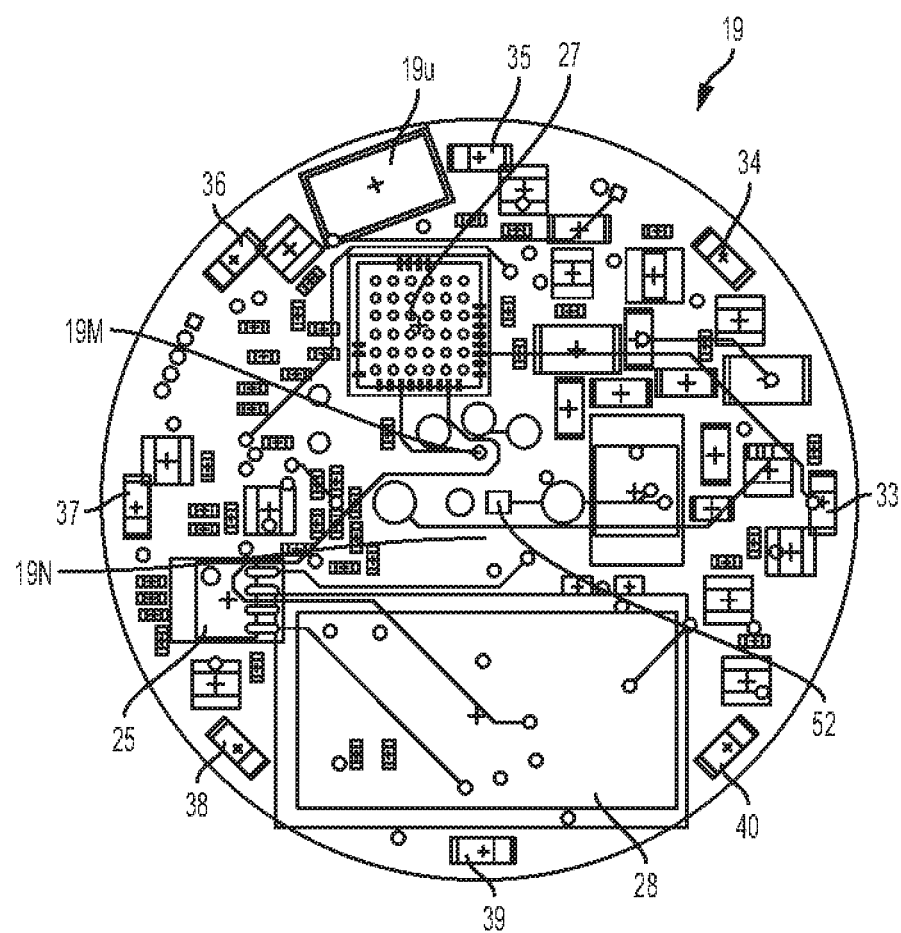
FIG. 8 is a top view of circuit board of the stethoscope of FIG. 1.

The circuit board 19 (also shown in FIG. 8) can have a variety of configurations. In general, the circuit board 19 can have electronic components of the stethoscope 10 mounted thereon or otherwise attached thereto. The circuit board 19 can include an amplifier chip 25 connected to the potentiometer 8 (e.g., the distal portion 23 thereof) by first connection elements 24, which include multiple connection elements in this illustrated embodiment but can be a single connection element. The amplifier chip 25 can be configured as a digital signal processor (DSP) or processing chipset.

The circuit board 19 can include a processor chipset 27 (also referred to herein as a "processor") connected to the potentiometer (e.g., the distal portion 23 thereof) by a second connection element 26, which includes a single connection element in this illustrated embodiment but can be multiple connection elements.

The circuit board 19 can include a Bluetooth chip 28 configured to facilitate wireless communication with external electronic devices (e.g., a Smart phone, a Smart watch, a tablet, a laptop, a headset, etc.) via Bluetooth. The Bluetooth chip 28 can be configured to be selectively activated, which may allow Bluetooth to be active only when needed, which may help conserve power and/or conserve processor resources. Bluetooth can be configured to automatically turn off or disconnect after a certain amount of time (e.g., one minute, two minutes, five minutes, etc.), which may help conserve power and/or conserve processor resources. When Bluetooth is active, the stethoscope 10 can be paired with an external electronic device having Bluetooth capability, as discussed further below. The knob 11 being rotated in a first direction (e.g., clockwise) can be configured to activate the Bluetooth chip 28 so as to turn on Bluetooth functionality. This rotation can be configured to cause an audible sound such as a click to indicate that Bluetooth is active, such as by the knob 11 and the hollow body 9 having corresponding engagement features that engage one another after the knob 11 has been rotated a certain amount in the first direction so as to produce the audible sound as the engagement members pass during the rotation. The knob 11 being rotated in a second, opposite direction (e.g., counterclockwise) can be configured to de-activate the Bluetooth chip 28 so as to turn off Bluetooth functionality. This rotation can be similarly configured to cause an audible sound to indicate that Bluetooth is inactive.

The circuit board 19 can include a USB unit 19u configured to electronically communicate with a USB device inserted into the USB port 15.

The circuit board 19 can include at least one audio sensor (also referred to herein as a "microphone"), which includes first and second microphones 19M, 19N in this illustrated embodiment. Gain of the at least one microphone can be configured to be adjusted so as to adjust volume. The knob 11 can be configured to be pushed downwardly (distally), as shown by arrow B in FIG. 6, to activate (e.g., turn on) the at least one microphone and thereby allow the stethoscope 10 to collect sounds indicate a bodily characteristic, e.g., a heartbeat or breathing Rotating the pushed-down knob 11 in a first direction (e.g., clockwise) while being held down can be configured to cause a positive microphone gain and rotating the pushed-down knob 11 in a second, opposite direction (e.g., counterclockwise) can be configured to cause a negative microphone gain. Movement of the knob 11 upward (proximally), such as by release of the knob 11 to allow the knob 11 to move to its biased proximal position, can cause the at least one microphone to be de-activated (e.g., turn off), which may protect the user from auditory spikes. The at least one microphone can thus be configured to be selectively activated and to have its gain adjusted while activated. The proximal movement of the knob 11 can be configured to cause data transmission from the stethoscope 10 to an external electronic device, such as wireless transmission of gathered data for off-board storage and/or analysis. Instead of the knob 11 being configured to be pushed down and rotated to adjust microphone gain and rotated without being pushed down to adjust Bluetooth capability, the knob can be configured to be pushed down and rotated to adjust Bluetooth capability and rotated without being pushed down to adjust microphone gain. In at least some embodiments, the at least one microphone can be configured to be powered off so as to be unable to emit sound when the knob 11 is in its proximal position, which can help conserve power.

The circuit board 19 can include a microphone pickup 51 configured to facilitate sound receipt by the at least one microphone. The microphone pickup 51 can face the base 13, as shown in FIG. 6, since the base 13 is positioned on a subject during use of the stethoscope 10.

The circuit board 19 can include one or more lights, which includes eight light emitting diodes (LEDs) 33, 34, 35, 36, 37, 38, 39 and 40 in this illustrated embodiment. In the case of a single light, the light can be fitted to a center of the circuit board 19. In the case of a plurality of lights, the plurality of lights can be configured as a light ring or light pipe extending around a perimeter of the stethoscope 10. The lights can be arranged equidistantly around a perimeter of the circuit board 19, which may facilitate even lighting around a perimeter of the stethoscope 10.

The one or more lights can be configured to illuminate in a single color. The single color can be used to indicate a characteristic of the stethoscope 10, such as the lights illuminating for a brief period of tie in response to the stethoscope 10 being powered on or off or the lights blinking during data transmission and/or receipt via the USB port 15, and/or to indicate a bodily characteristic of the subject with which the stethoscope 10 is associated, such as the lights blinking in conjunction with sensed heart beats or the lights illuminating at a point in time corresponding to a detected abnormality such as a heart murmur or a breath wheeze. Alternatively, the lights can be configured to illuminate in a plurality of different colors, e.g., red, blue, green, orange, yellow, purple, white, etc. As will be appreciated by a person skilled in the art, each of the lights can be configured to illuminate in multiple colors to produce the different colored lights, or different ones of the lights can be configured to illuminate in different colors to produce the different colored lights. The plurality of colors can be used to indicate a characteristic of the stethoscope 10 and/or a bodily characteristic of the subject with which the stethoscope 10 is associated similar to that discussed above regarding the lights being configured to illuminate in a single color. Each of the plurality of colors in a steady (non-blinking) illuminated state can be associated with a different characteristic, which may facilitate fast user identification of the characteristic being indicated by the lights. Similarly, each of the plurality of colors in a blinking state can be associated with a different characteristic, which may facilitate fast user identification of the characteristic being indicated by the lights. For example, steady light in a first color for a brief period of time can indicate the stethoscope 10 being powered on/off, blinking in a second color can indicate data transmission or receipt via the USB port 15, blinking in a third color can indicate that the battery 54 needs recharging, steady light in a fourth color can indicate that the stethoscope 10 has properly powered on and is now ready for use, spinning light in a fifth color (e.g., successive ones of the lights being illuminated in a track-like pattern) during stethoscope 10 use on a subject with the spinning lights changing to a sixth color at a point in time corresponding to a detected abnormality and back to the fifth color when the detected abnormality ceases, blinking light in the first color can indicate that the stethoscope 10 has been properly synced with another stethoscope, etc.

Brightness of the one or more lights can be configured to be adjusted. The stethoscope 10 can include a light sensor (not shown) built into the circuit board 19. The light sensor can be configured to detect external lighting conditions and adjust the intensity of the one or more lights to suit the intensity of the one or more lights. For example, when a low level light setting is detected, the light intensity can be automatically reduced so as to not cause an extremely bright display. For another example, if the stethoscope 10 is used outdoors, the light sensor can detects this operation setting and result in the one or more lights emitting a more intense setting. In addition to or in alternative to the stethoscope 10 including a light sensor configured to facilitate automatic brightness adjustment, the brightness can be adjusted similar to that discussed above regarding adjustment of microphone gain, e.g., pushing down the knob 11 and rotating the knob 11 in the first direction to increase brightness and pushing down the knob 11 and rotating the knob 11 in the second direction to reduce brightness. Rotation of the knob 11 can thus be configured to adjust any two of Bluetooth capability, microphone gain, and brightness of the lights with one of these features being adjustable when the knob 11 is rotated in its proximal position and another one of these features being adjustable when the knob 11 is rotated in its pushed-down, distal position. Alternatively, the knob 11 can be configured to adjust all of Bluetooth capability, microphone gain, and brightness of the lights with one of these features (e.g., Bluetooth capability) being adjustable when the knob 11 is rotated in its proximal position and the other two of these features (e.g., microphone gain and brightness of the lights) being adjustable when the knob 11 is rotated in its pushed-down, distal position. In at least some embodiments, the lights can be configured to be powered off so as to be unable to illuminate when the knob 11 is in its proximal position, which can help conserve power.

The circuit board 19 can include a central aperture 32. The central aperture 32 can be configured to facilitate coupling of the rotary potentiometer 8 to the circuit board 19 via a central connection element 52 configured to extend through the central aperture 32, as shown in FIG. 6. The central aperture 32 can be configured to facilitate microphone pickup by helping sound from outside the stethoscope 10, e.g., sound from a subject on which an exterior distal surface of the stethoscope 10 (e.g., an exterior distal surface of the base 13) is placed, be picked up by the first and second microphones 19M, 19N.

The rotary potentiometer 8 can have a variety of configurations. The rotary potentiometer 8 can include the distal portion 23, an upper or proximal portion, and an intermediate portion 20 between the upper and lower portions. The distal portion 23 can be positioned over the central aperture 32 of the circuit board 19, to which the distal portion 23 can be attached. The upper portion of the rotary potentiometer 8 can include a post 22 configured to be seated in the cavity 45 of the knob 11. The post 22 can have longitudinal splines 21 formed thereon configured to operatively engage with the longitudinal splines 21A of the knob 11 such that rotation of the knob 11 can cause corresponding rotation of the post 22 and hence of the distal portion 23 of the potentiometer 8 attached thereto. The intermediate portion 20 of the rotary potentiometer 8 can be configured as a bearing surface for rotation of the hollow body 9 in conjunction with rotation of knob 11.

The rotary potentiometer 8, e.g., the distal portion 23 thereof, can include a bias element (not shown), such as a spring. The bias element can be configured to bias, e.g., spring-load, the rotary potentiometer 8 to a proximal position. This biasing can bias the post 22 upwards, which in turn can bias the knob 11 to be in its default, proximal-most position within the groove 16 of the hollow body 9.

The rotary potentiometer 8 can include one or more slots formed therein, e.g., in a distal surface of the distal portion 23. The stethoscope 10 includes first and second slots 55, 56 in this illustrated embodiment. A height of the first and second slots 55, 56 can define an amount of vertical (proximal/distal) movement of the potentiometer 8 (and the knob 11) relative to the base 13, as shown by arrow C in FIG. 7, in response to pressing and release of the knob 11 as shown by arrow B. A length of the engagement between the splines 21A, 21 of the knob 11 and the post 22 can also define the amount of vertical movement of the potentiometer 8 (and the knob 11) relative to the base 13.

The rotary potentiometer 8 can generally be configured as a variable resistor or rheostat and can thus generally function as a voltage divider that can measure electric potential. The rotary potentiometer 8 can be used to control adjustable microphone output, such as to increase or decrease sounds provided by the stethoscope's at least one microphone and/or to provide positive or negative microphone gain.

The base 13 can have a variety of configurations. As mentioned above, the hollow interior 18 of the base 13 can be configured to seat the distal portion 17 of the hollow body 9 therein and configured to seat the circuit board 19 therein. The base 13 can include a peripheral cavity 48 configured to retain the distal portion 17 of the hollow body 9 therein. The base's cavity 48 can be defined by a flexible outer wall 49 and a flexible inner wall 50.

The base 13 can have a central opening 13c formed in a distal surface thereof. The central opening 13c can be configured to facilitate microphone pickup and can be aligned with the central aperture 32 of the circuit board 19 to further facilitate microphone pickup.

The base 13 can include a viewing window 13w configured to facilitate visualization of light emitting by the one or more lights 33, 34, 35, 36, 37, 38, 39 and 40. For example, the viewing window 13w can be a transparent or translucent portion configured to allow light to shine therethrough. The viewing window 13w can extend fully around a perimeter of the base 13, which may facilitate visualization of emitted light from nearly any angle of viewing. In an exemplary embodiment, the viewing window 13w is at a proximal end of the base 13 or is part of a distal portion of the hollow body 9. Such positioning can facilitate visualization of the one or more lights 33, 34, 35, 36, 37, 38, 39 and 40 since the illuminated display will be above (proximal to) the bottom of the base 13 that is positioned on a subject. A user of the stethoscope 10, as well as the subject, can thus be able to see the body sound pulse via light display.

The base 13 can be non-removably attached to the hollow body 9, which may help provide a waterproof device and/or a device resistant to tampering or damage. Alternatively, the base 13 can be a modular component configured to be removably and replaceably coupled to the hollow body 9, which may facilitate cleaning of the base 13 and/or may allow different bases having different functionalities to be coupled to a remainder of the stethoscope 10. The stethoscope 10 can be provided as part of a kit including a plurality of different bases each configured to be removably and replaceably attached to the hollow body 9, which may allow a user to swap bases as desired for particular uses of the stethoscope 10. Examples of modular bases include a base configured for heart sound detection that includes ECG sensors, a base configured for non-heart sound detection that does not include any ECG sensors, a base configured for respiratory sound detection that includes one or more oxygen saturation sensors, a base configured for infrared sensing of temperature that includes one or more infrared sensors, and a base configured for ultrasound sensing that includes one or more ultrasound sensors.

The base 13 can include a wireless charging receiver (not shown), such as a wireless charging copper plate, to allow for wireless charging of the stethoscope 10. The wireless charging receiver can be in addition to or instead of the USB port 15 that can be configured to facilitate charging of the stethoscope 10.

The knob 11, the hollow body 9, and the base 13 can be formed from any of a variety of materials. In an exemplary embodiment, the knob 11 and the hollow body 9 can be formed from one or more biocompatible rigid materials, such as stainless steel, titanium, or any of a number of polymers. Rigid material may help provide durability to the stethoscope 10. In an exemplary embodiment, the base 13 can be formed from neoprene or other flexible or resilient plastics material configured to resiliently retain the distal portion 17 of the hollow body 9. The flexible inner and outer walls 49, 50 of the base 13 can facilitate this resilient retention.

Figure 9:
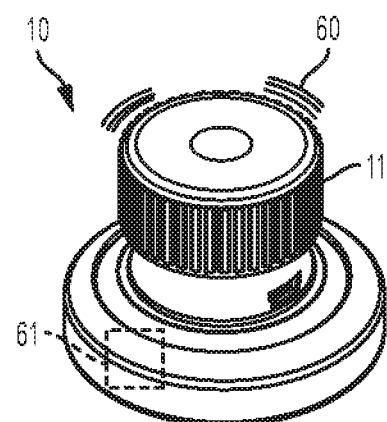
FIG. 9 is a perspective view of the stethoscope of FIG. 1, the stethoscope vibrating.
Figure 10:
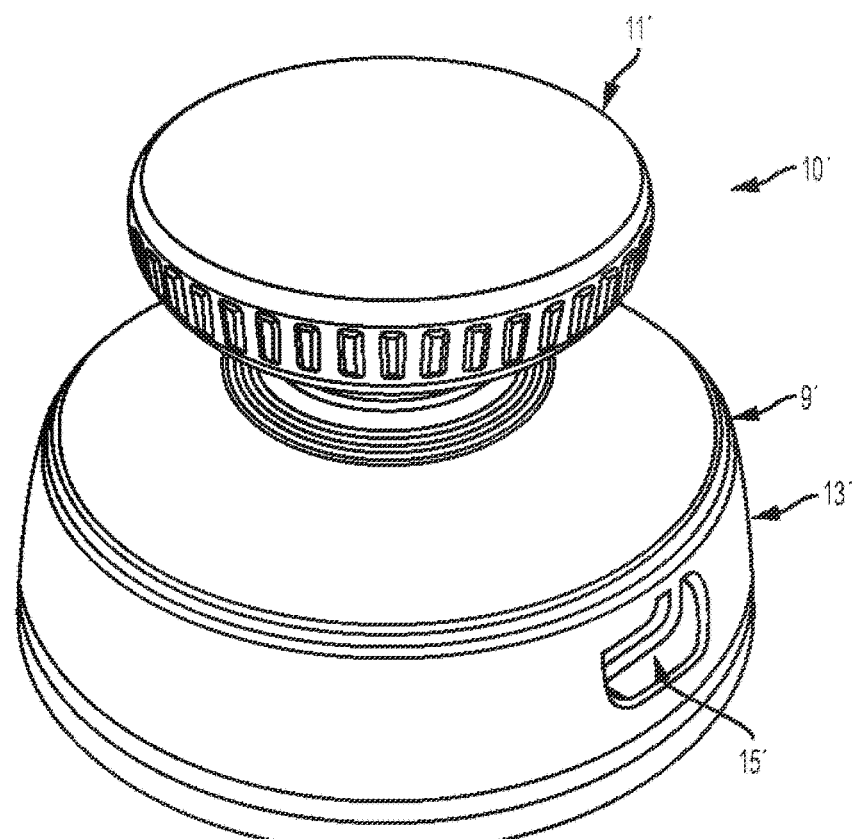
FIG. 10 is a perspective view of another embodiment of a stethoscope.
Figure 11:
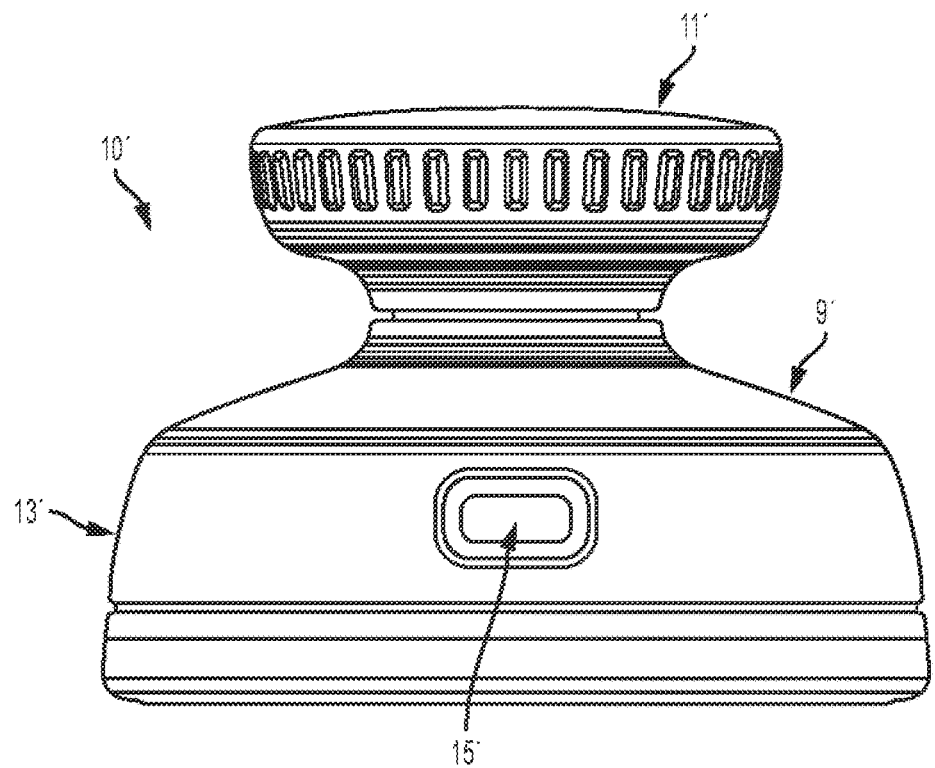
FIG. 11 is a side view of the stethoscope of FIG. 10.
Figure 12A:
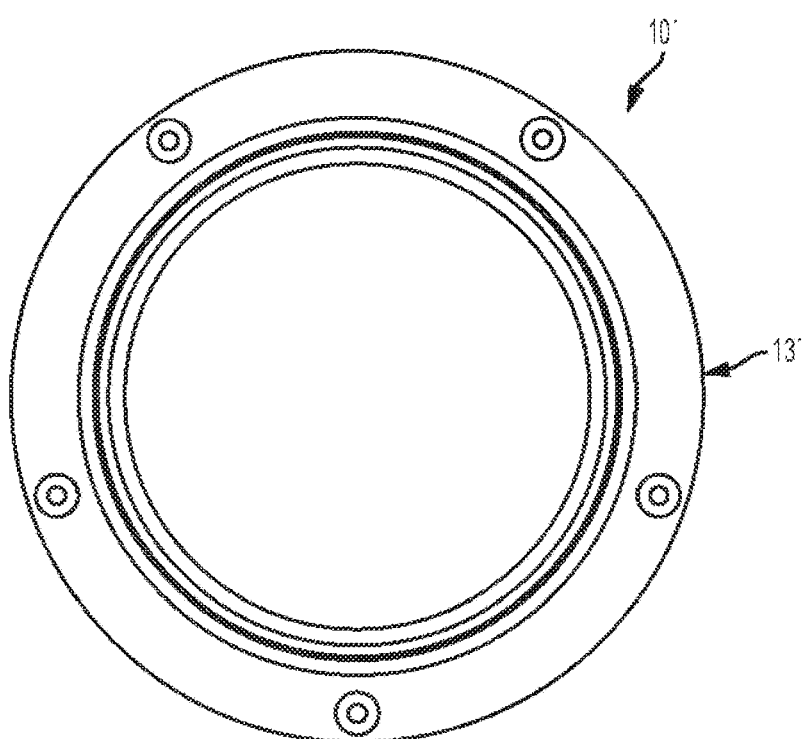
FIG. 12A is a distal end view of the stethoscope of FIG. 10.
Figure 12B:
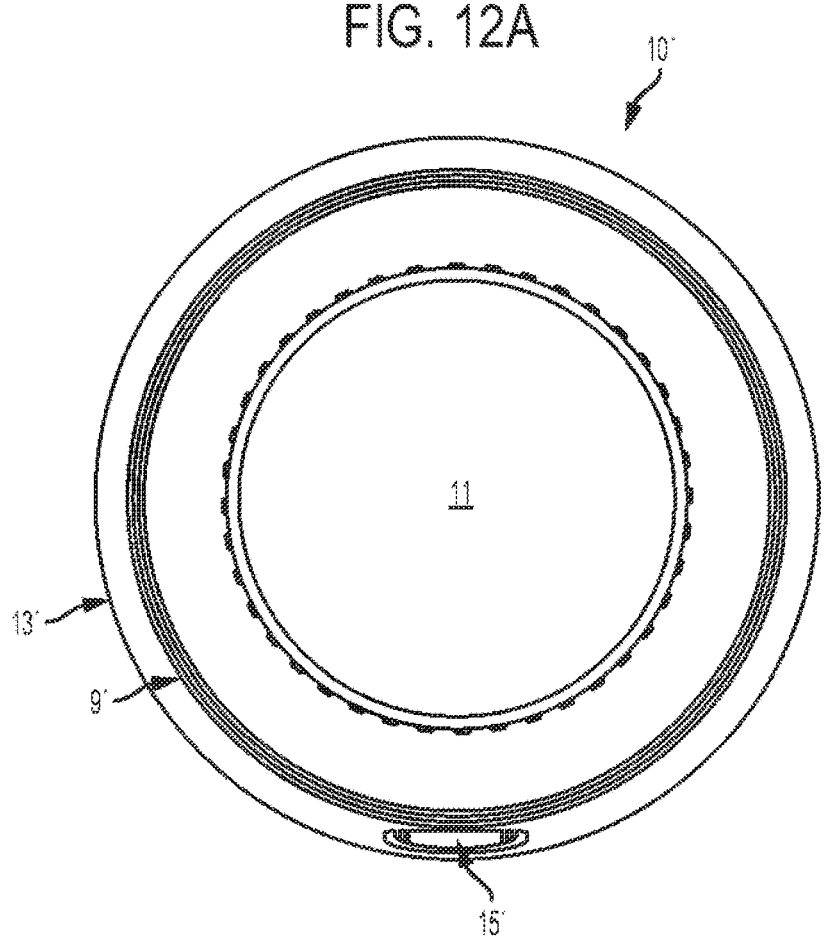
FIG. 12B is a proximal end view of the stethoscope of FIG. 10.

As shown in FIG. 9, the stethoscope 10 can include a vibration motor 61 (also referred to herein as a "vibration generator") configured to vibrate in response to occurrence of a trigger event.

The vibration generator 61 can include any type of vibration generator, as will be appreciated by a person skilled in the art. The vibration motor 61 can, as shown in this illustrated embodiment, be internal to the stethoscope 10, such as by being attached to the circuit board 19, which may help protect the vibration motor 61 from being damaged. The vibration of the vibration motor 61 can cause a sound to be emitted, as represented by sound lines 60 in FIG. 9. The sound can be heard by a user handling the stethoscope 10 and any other nearby people, thereby signaling that a trigger event occurred. The vibration of the vibration motor 61 can be palpably felt by the user handling the stethoscope 10, thereby signaling to the user that a trigger event occurred. The vibration motor 61 can thus be configured to provide two types of signal, audible (sound) and tactile (palpable vibration), which may help ensure that the user handling the stethoscope 10 realizes that a trigger event occurred because at least one of the audible and tactile signals should be detectable even if both types of signals are not detected for any reason and may help ensure that interested parties not handling the stethoscope 10, and thus unable to feel the vibration, can realize that a trigger event occurred because the sound can be heard. As discussed herein, the vibration can be felt by the user holding the stethoscope 10 as well as by each of one or more other users who each have a linked stethoscope to the stethoscope 10 and by each of one or more users who has a mobile device or other electronic device linked to the stethoscope 10 that uses its own internal vibration mechanism to provide the vibration.

A variety of trigger events can be configured to cause the vibration motor 61 to vibrate. For example, the vibration motor 61 can be configured to vibrate in conjunction with detected heart sounds (e.g., as short and sharp vibrations) so as to provide a sound and feel of the heartbeat. For another example, the vibration motor 61 can be configured to vibrate in conjunction with detected beginning of breathing inspiration and with detected beginning of breathing expiration so as to provide a sound and feel of a breathing cycle. For yet another example, the vibration motor 61 can be configured to vibrate once or in a short series of vibrations in response to the stethoscope 10 being powered on or off so as to provide confirmation of the stethoscope's power status.

The stethoscope 10 can include a multi-axis accelerometer (not shown) that can be used to determine an axis and position of placement of the stethoscope 10 on a subject's body when a measurement using the stethoscope 10 was taken. The multi-axis accelerometer can include any type of multi-axis accelerometer, as will be appreciated by a person skilled in the art. The accelerometer can, similar to the vibration motor 61, be internal to the stethoscope 10, such as by being attached to the circuit board 19, which may help protect the accelerometer from being damaged. Data regarding the axis and position determined using the accelerometer may help to describe the subject's position (e.g. lying down, sitting in a chair, etc.) when the stethoscope 10 reading was taken, and/or the amount of movement or force of the heartbeat on the subject's chest wall. This data can be useful in enabling the subject, a user handling the stethoscope 10, and/or other person to determine an optimal seating position, angle, etc. for the subject and/or an optimal area on the subject's chest to pick-up the best sound (e.g., heart sound or lung sound) from the subject using the stethoscope 10.

The accelerometer can be configured to help indicate when the stethoscope 10 is being actively used on a subject, as opposed to when it is being carried between locations. When, with the assistance of the accelerometer, the stethoscope 10 (e.g., the processor 27 thereof) determines that the stethoscope 10 is being actively used, the stethoscope 10 can be configured to put itself into a normal energy consumption state (e.g., the processor 27 can cause the stethoscope 10 to move from an energy saving state to the normal energy consumption state). Similarly, then the stethoscope 10 determines with the aid of the accelerometer that the stethoscope is not being used and just being carried, the stethoscope 10 can be configured to put itself into the energy saving state.

The stethoscope 10 can include an audio filter (not shown) configured to filter out noise from audio that is output from the stethoscope 10. The audio filter can include any type of audio filter, as will be appreciated by a person skilled in the art. The audio filter can, similar to the vibration motor 61, be internal to the stethoscope 10, such as by being attached to the circuit board 19, which may help protect the audio filter from being damaged. The audio filter can be configured to remove unwanted surface movement and scratch noises. If the accelerometer detects movement of the stethoscope 10 (e.g., if the processor 27 interprets the accelerometer's gathered data to indicate movement of the stethoscope 10), the audio filter can be configured to automatically turn on so that it can filters out any movement or scratch noises from output audio. If the accelerometer detects that the stethoscope 10 is stationary (e.g., if the processor 27 interprets the accelerometer's gathered data to indicate that the stethoscope 10 is not moving), the audio filter can be configured to automatically turn off since it is not needed to clean output audio, thereby helping to conserve power and/or processor resources.

The stethoscope 10 can include one or more sensors configured to sense a body characteristic. The sensed data may facilitate a medical professional's understanding of the bodily sounds gathered by the stethoscope 10 and/or facilitate diagnosis of the subject. The one or more sensors can be configured to be activated in the same way and at the same time as the stethoscope's at least one audio sensor, e.g., by pushing down the knob 11.

For example, the stethoscope 10 can include three electrocardiogram (ECG) EPIC™-type sensors (not shown) (e.g., a sensor plate). In an exemplary embodiment, the ECG sensors can be positioned on the exterior distal surface of the base 13 of the stethoscope at the 3 o'clock and 9 o'clock positions (e.g., 180° apart from one another on opposite sides of the stethoscope 10). Having ECG sensors can allow a two-lead ECG to be taken using the stethoscope 10. For example, in use, a user can grip the base 13 of the stethoscope 10 with the user's index finger and thumb resting on the knob 11 of the stethoscope 10 and then push the knob 11 of the stethoscope 10 down using the thumb so as to activate the ECG sensors, e.g., to electronically connect the ECG sensors. Electrical signals output from the ECG sensors can then be used to develop a basic two-lead ECG by processor 27 analysis and/or by off-board processor analysis.

Electrical signals output by the ECG sensors can define a trigger event that causes the one or more lights of the stethoscope 10 and/or the vibration motor of the stethoscope 10 to be activated. More particularly, the one or more lights of the stethoscope 10, e.g., the LEDs 33, 34, 35, 36, 37, 38, 39 and 40 and/or the vibration motor can be controlled in response to the electrical signals output by the ECG sensors to indicate any anomalies detected by the ECG sensors as analyzed by the processor 27 and/or an off-board processor.

For another example, the stethoscope 10 can include at least one non-contact thermometer sensor (not shown) configured to detect body temperature. In an exemplary embodiment, the at least one temperature sensor can be positioned on the exterior distal surface of the base 13 so as to be configured to contact a subject's skin surface during use of the stethoscope 10.

For yet another example, the stethoscope 10 can include at least one oxygen saturation sensor (not shown) configured to detect a percentage of oxygen (pO2) in vessels in the subject's blood when the stethoscope's pO2 sensor is placed on a finger tip of the subject. In an exemplary embodiment, the at least one oxygen saturation sensor can be positioned on the exterior distal surface of the base 13.

The stethoscope 10 can be configured to stream data from the accelerometer and/or the ECG sensors to a software application executing on an external electronic device (e.g., a Smart phone, a laptop, a server, etc.). The data can be streamed via a wired connection (e.g., a connection via the USB port 15) or wirelessly. The processor 27 can be configured to control the streaming.

The stethoscope 10 can include a speech recognition facility for enabling the operation of the stethoscope 10 to be controlled using verbal commands. For example, the speech recognition facility can be configured to, in response to a verbal command prompt such as "OK Stethee" spoken to the stethoscope 10, allow the processor 27 to cause the stethoscope 10 to wake-up from the low energy consumption state to the normal energy consumption state. For another example, the speech recognition facility can be configured to, in response to a verbal command prompt such as "volume up" spoken to the stethoscope 10, allow the processor 27 to cause the at least one microphone to increase in gain.

The stethoscope 10 can include a touch button (not shown) configured to keep the at least one microphone active and to keep Bluetooth active. The touch button can thus allow the at least one microphone and Bluetooth active without the knob 11 having to be pushed and held down, which may not be appropriate in all circumstances, such as when pressure placed on a subject's abdomen is not appropriate, the subject is particularly sensitive to pressure, etc. The touch button can be configured to be pressed instead of the knob 11 being pressed and held during sound detection. Pressing and holding the touch button for a predetermined amount of time (e.g., one second) can be configured to keep the stethoscope 10 in the energy saving state, and pressing the touch button again can be configured to turn off the energy saving state. The touch button can be configured to illuminate, e.g., flash green or another color, to indicate this power state change. Pressing and holding the touch button for a longer predetermined amount of time (e.g., five seconds) can be configured to place the stethoscope 10 into Bluetooth connect mode, e.g., to allow Bluetooth connection. The touch button can be configured to illuminate in a different way than is indicate of the energy state change, e.g., by flashing blue or other color. In addition to or instead of the stethoscope 10 including the touch button, an electronic device linked to the stethoscope 10 can provide the touch button via an APP installed on the electronic device so as to allow the stethoscope 10 to be activated by remote control. All functions of the stethoscope 10 can be configured to be accessed via the APP and controlled like a remote control device.

The stethoscope 10 can include a display (not shown) such as an LED display, Smart watch type organic light-emitting diode (OLED) display, etc. In an exemplary embodiment, the display can be on the knob 11, which may facilitate visualization of the display when the stethoscope 10 is in use, e.g., when the base 13 contacts a subject. The display can include a screen that allows a user of the stethoscope 10 to see information that would be normally visualized on a computer or other electronic device, such as via an APP installed thereon. The stethoscope 10 including the built in display can allow the stethoscope 10 to function as a standalone device without needing to be linked to a mobile device or other electronic device to view information on a graphical user interface (GUI), such as GUIs discussed further below. The display can be configured as a touch screen that allows the user to change various settings on the stethoscope 10 from a settings menu, such as the settings discussed further below with respect to various GUIs.

The stethoscope 10 can have a variety of sizes and weights. The stethoscope 10 can be portable and can consequently have a size and weight that facilitates easy portability of the stethoscope 10. In one embodiment, the stethoscope 10 can have a maximum height (measured vertically) of about 38 mm, a maximum width (measured horizontally) of about 55 mm, and a weight of about 110 grams.

FIGS. 10-12B illustrate another embodiment of a stethoscope 10'. The stethoscope 10' can generally be configured and used similar to the stethoscope 10 of FIGS. 1 and 2, e.g., can include a knob 11', a hollow body 9', a rotary potentiometer (not shown), a base 13', a USB port 15', and a circuit board (not shown) having electronic components (not shown) (e.g., an amplifier chip, a processor, a Bluetooth chip, a USB unit, one or more microphones, one or more lights, a vibration motor, etc.), a voltage regulator, etc.

Figure 13A:
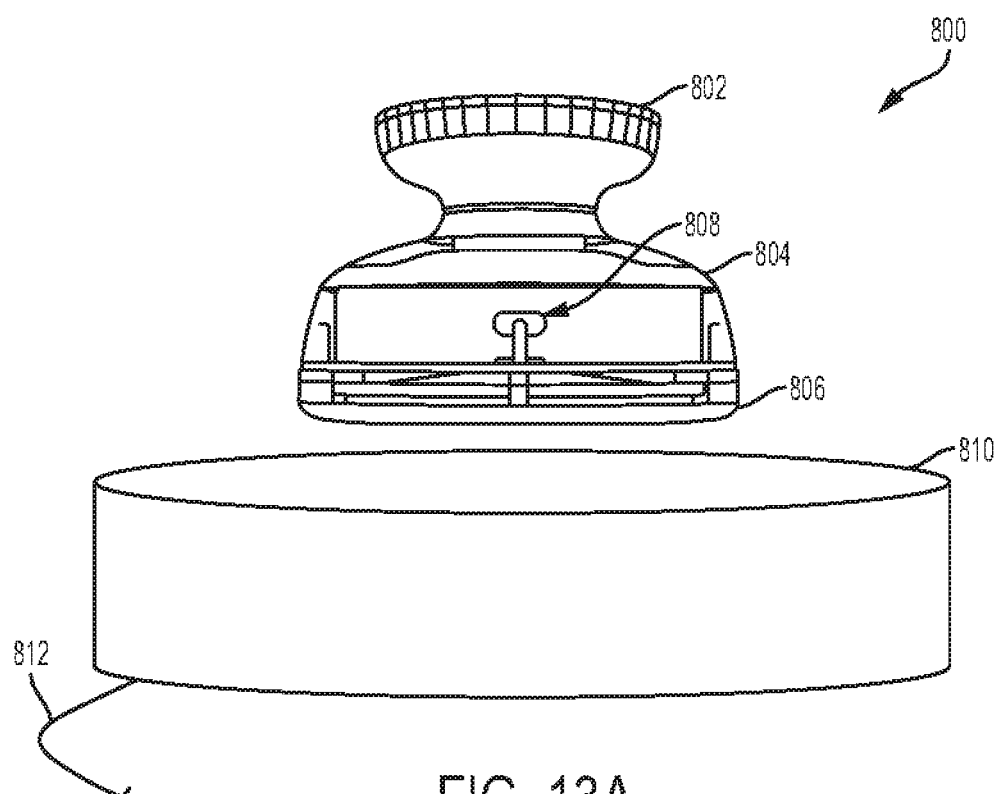
FIG. 13A is a side view of another embodiment of a stethoscope and one embodiment of a wireless transmitter.
Figure 13B:
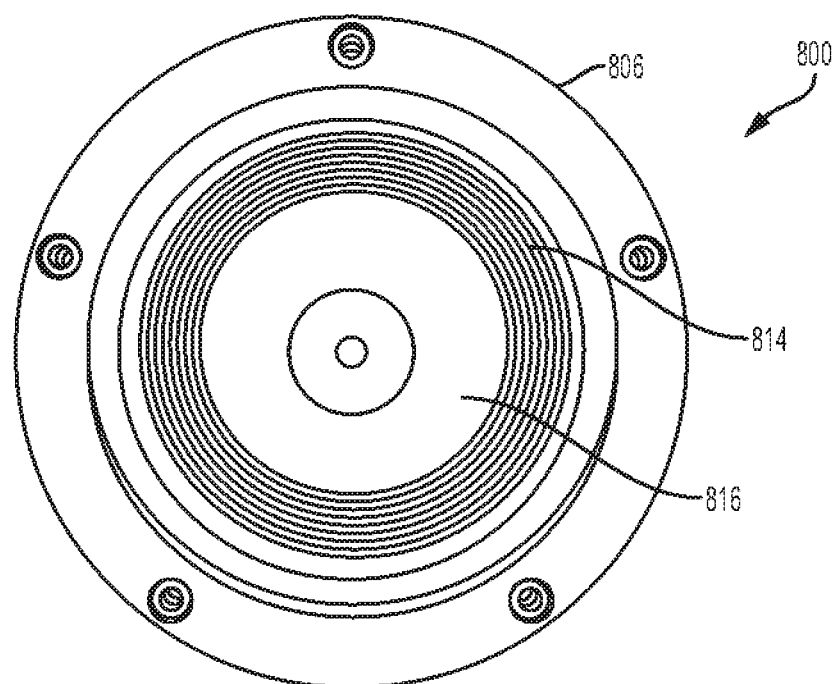
FIG. 13B is a bottom view of the stethoscope of FIG. 13A.

FIGS. 13A and 13B illustrate another embodiment of a stethoscope 800. The stethoscope 800 can generally be configured and used similar to the stethoscope 10 of FIGS. 1 and 2, e.g., can include a knob 802, a hollow body 804, a rotary potentiometer (not shown), a base 806, a USB port 808, and a circuit board (not shown) having electronic components mounted thereon or otherwise attached thereto, etc. The stethoscope 800 in this illustrated embodiment is configured to be wirelessly charged using a charging dock 810. The charging dock 810 can have any of a variety of configurations, as will be appreciated by a person skilled in the art. As in this illustrated embodiment, the charging dock 810 can include a wireless transmitter therein (obscured in FIG. 13A) and can include a USB charging cord 812 extending therefrom.

Figure 13C:
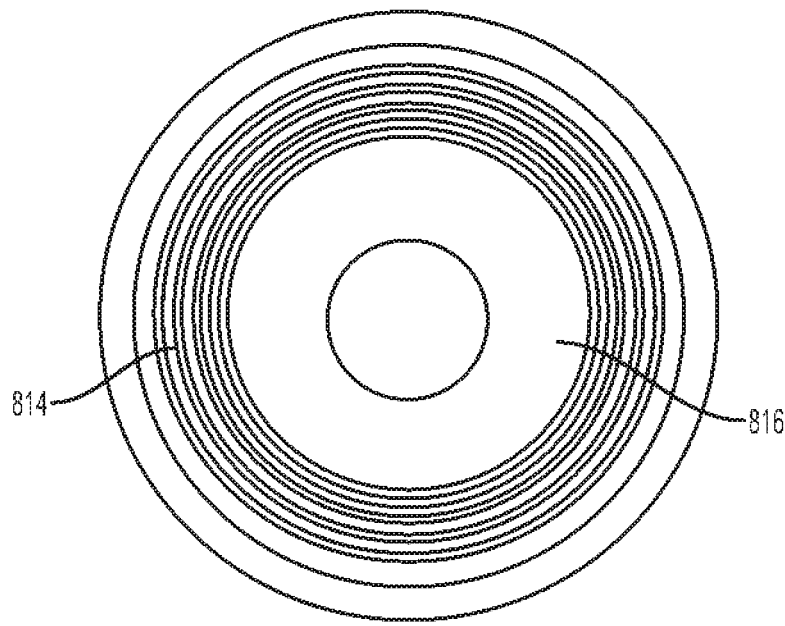
FIG. 13C is a bottom view of a diaphragm of the stethoscope of FIG. 13A.
Figure 13D:
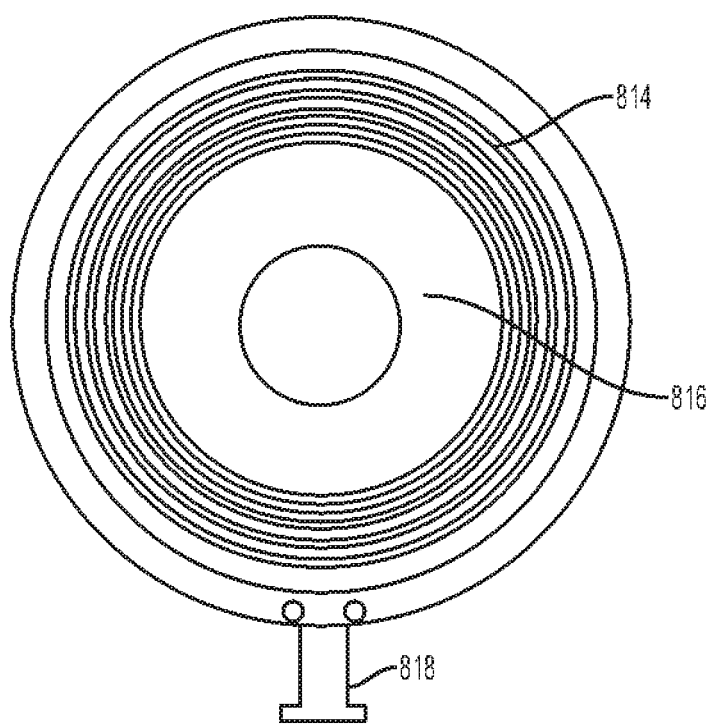
FIG. 13D is a bottom view of a diaphragm of the stethoscope of FIG. 13A coupled to one embodiment of a charging cable.

As shown in FIGS. 13B-13D, the base 806 can include a wireless charging receiver 814, in the form of a wireless charging coil, coupled to a diaphragm 816 on a bottom (distal) surface of the base 806. The wireless charging receiver 814 can, for example, be embedded into the material that forms the diaphragm 816. The wireless charging receiver 814 can be configured to facilitate wireless charging of the stethoscope 800 via the charging dock 810 when the stethoscope 800 is sufficiently within transmission range of the charging dock's wireless transmitter, such as by using the Qi interface standard. As will be appreciated by a person skilled in the art, the Qi interface standard facilitates inductive electrical power transfer from a distance of up to about 4 cm. In use, the bottom surface of the base 806 that includes the wireless charging receiver 814 can be placed directly on or within an effective range of a top (proximal) surface of the dock 810, which can allow wireless charging of the stethoscope 800 via resonant inductive coupling.

The diaphragm 816 can include a first portion that includes the wireless charging receiver 814 and a second, free portion that is free of the wireless charging receiver 814. The diaphragm 816 having a free portion may facilitate sound transmission therethrough. As in this illustrated embodiment, the first portion can be an outer ring of the diaphragm 816, and the second portion can be an inner area of the diaphragm 816 within the outer ring.

As shown in FIG. 13D, the stethoscope 800 can be configured to couple to a charging cable 818, e.g., via the stethoscope's USB port, to allow wired charging of the stethoscope 800. A user can thus selectively charge the stethoscope wirelessly or by wired connection.

Figure 14:
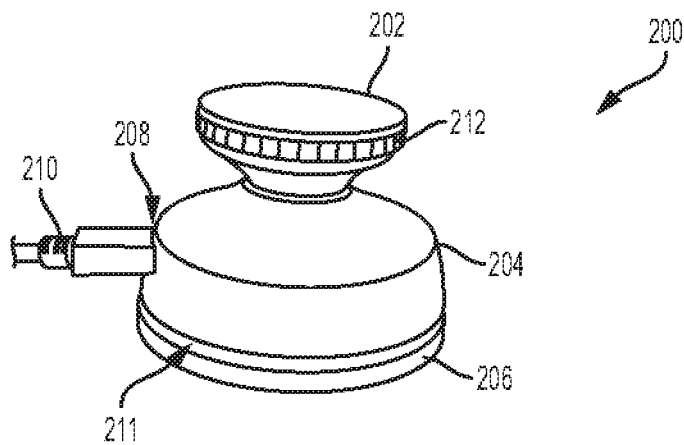
FIG. 14 is a perspective view of yet another embodiment of a stethoscope, the stethoscope having a USB cord coupled thereto.

FIG. 14 illustrates yet another embodiment of a stethoscope 200. The stethoscope 200 can generally be configured and used similar to the stethoscope 10 of FIGS. 1 and 2, e.g., can include a knob 202, a hollow body 204, a rotary potentiometer (not shown), a base 206, a USB port 208, and a circuit board (not shown) having electronic components mounted thereon or otherwise attached thereto, etc. FIG. 14 shows a USB cord 210 inserted in the USB port 208 and a blue light illuminating through a viewing window 211 of the base 206 indicating the active USB connection. The knob 202 and the hollow body 204 in this illustrated embodiment are formed from stainless steel. The knob 202 in this illustrated embodiment has a gripping feature 212 in the form of a rubber ring.

Figure 15:
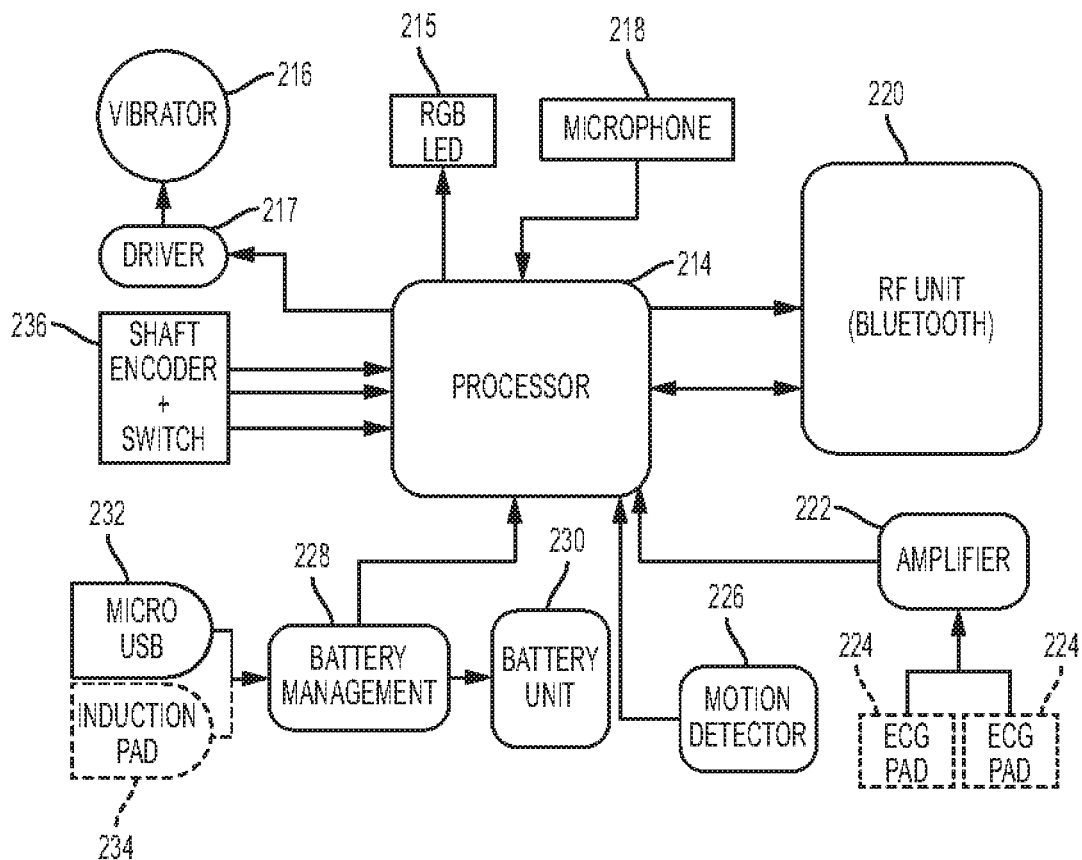
FIG. 15 is a schematic circuit of the stethoscope of FIG. 14.

FIG. 15 illustrates electronic components mounted on or otherwise attached to the circuit board of the stethoscope 200. As shown, the electronic components can include a processor 214, one or more lights 215 (at least one RGB LED in this illustrated embodiment) configured to be controlled by the processor 214, a vibrator (vibration motor) 216 configured to be controlled by the processor 214 via a driver 217, one or more microphones 218 configured to provide output to the processor 214, an RF unit 220 configured to provide Bluetooth functionality and to electronically communicate with the processor 214, an amplifier 222 configured to provide amplified data to the processor 214 from ECG sensors 224 (ECG pads in this illustrated embodiment) on the base 206, an accelerometer (motion detector) 226 configured to provide data to the processor 214, a battery manager (battery management) 228 configured to communicate with a battery unit (power source) 230 and the processor 214 and to receive charge via a micro USB 232 in electronic communication with an induction pad 234 of the USB port 208, and a shaft encoder and switch 236 configured to provide output to the processor 214.

Figure 16A:
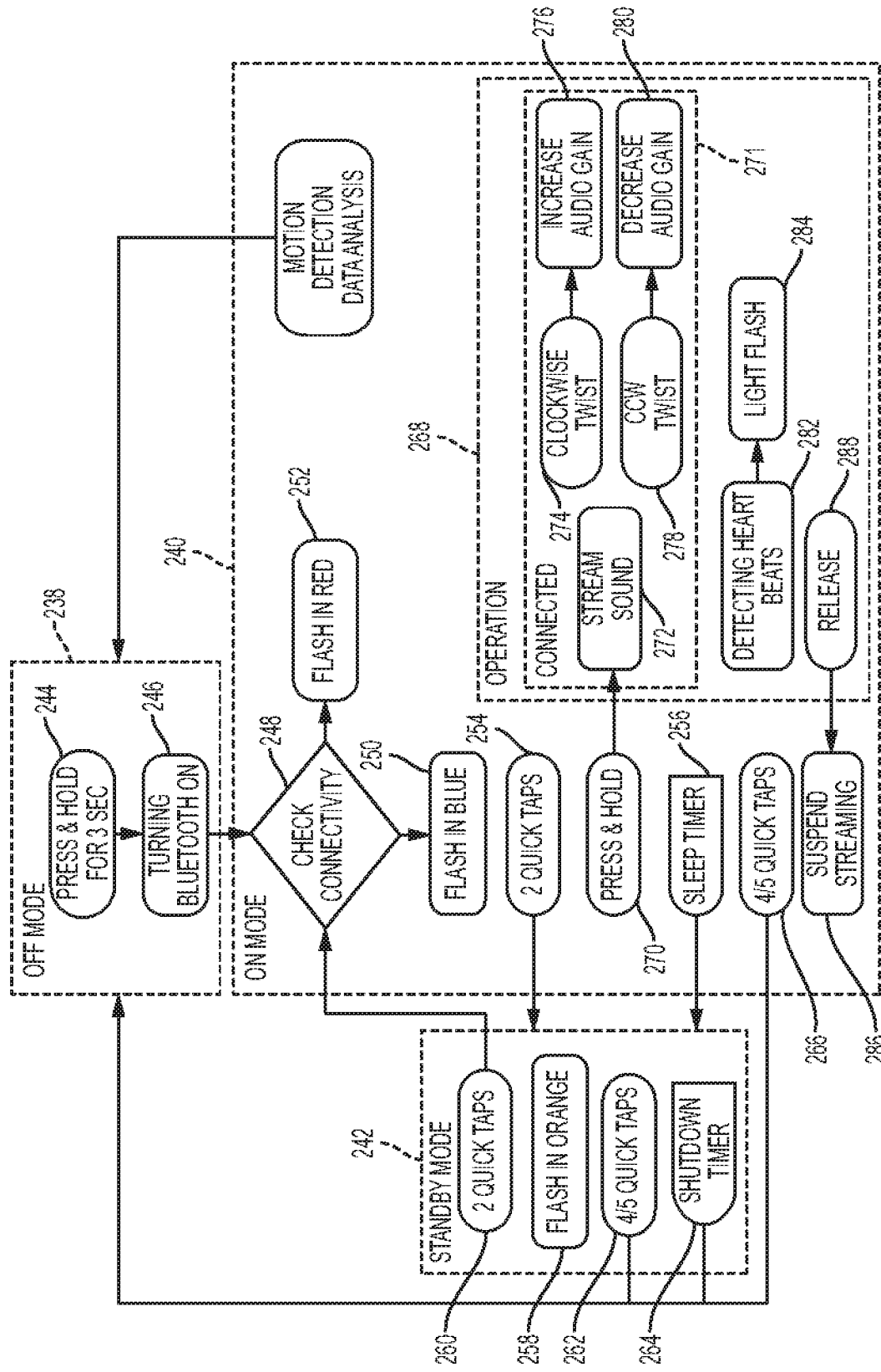
FIG. 16A is a flowchart of modes of the stethoscope of FIG. 14.

As shown in FIG. 16A, the stethoscope 200 can have three modes of operation: an OFF mode 238 in which the stethoscope 200 is powered off, an ON mode 240 in which the stethoscope 200 is powered on and is in a normal energy consumption state, and a STANDBY mode 242 in which the stethoscope 200 is powered on and is in an energy saving state. Other stethoscopes described herein can be configured to similarly have three modes of operation.

In the OFF mode 238, the knob 202 can be pushed down (distally) 244 relative to the hollow body 204 and the base 206 and held 244 down for a predetermined amount of time (three seconds in this illustrated example) to turn 246 on Bluetooth (e.g., to activate the RF unit 220) and transition the stethoscope 200 from the OFF mode 238 to the ON mode 240. When the stethoscope 200 enters the ON mode 240, the stethoscope 200 (e.g., the processor 214 thereof) can be configured to check 248 connectivity of the stethoscope 200 with a network and/or with an external electronic device. If connectivity exists, the one or more lights can flash (blink) 250 a number of times in a first color (blue in this illustrated embodiment) to signal the connectivity to a user of the stethoscope 200. If connectivity does not exist, the one or more lights can flash (blink) 252 a number of times in a second color (red in this illustrated embodiment) to signal the lack of connectivity to the user of the stethoscope 200, who may then troubleshoot to establish a connection.

In the ON mode 240, the stethoscope 200 can be operated 268 to detect a bodily characteristic, e.g., a heartbeat or breathing. The knob 202 can be configured to be pushed down and held 270 to activate 271 the at least one microphone 218 and thereby allowing the streaming 272 of sound received by the at least one microphone 218. The knob 202 can be configured to be rotated 274 in a first direction (clockwise in this illustrated embodiment) to increase 276 gain of the at least one microphone 218 and to be rotated 278 in a second, opposite direction (counterclockwise in this illustrated embodiment) to decrease 280 gain of the at least one microphone 218. In response to detected 282 heart beats (or breathing sounds), the one or more lights 215 can be configured to illuminate (e.g., flash 284). The stethoscope 200 can be configured to be moved from operation 268 to suspend 286 the streaming 272 by, e.g., releasing 288 the knob 202 from its held down position.

In the ON mode 240, the stethoscope 200 can be configured to be manually moved 266 by the user to the OFF mode 238, e.g., when the user knows that use of the stethoscope 200 on the subject is over or will not be resumed until after a break of time. The movement in this illustrated embodiment includes the user giving the knob 202 four or five quick downward taps.

In the ON mode 240, the stethoscope 200 can be configured to be manually moved by the user to the STANDBY mode 242, e.g., to conserve power and/or processor resources when the user knows the stethoscope 200 will not be immediately used on a subject. The movement 254 in this illustrated embodiment is caused by the user giving the knob 202 two quick downward taps. In addition to being manually movable to the STANDBY mode 242, the stethoscope 200 can be configured to automatically move from the ON mode 240 to the STANDBY mode 242 in response to a sleep timer 256 counting passage of a predetermined amount of time (e.g., an amount of time preprogrammed into the processor 214 as triggering STANDBY mode 242). In some embodiments, the stethoscope 200 can be configured to be only manually movable to the STANDBY mode 242 or to be only automatically movable to the STANDBY mode 242. Whether the STANDBY mode 242 is reached manually or automatically, the one or more lights 215 can be configured to flash 258 in a third color (orange in this illustrated embodiment) to indicate the mode change from ON to STANDBY.

The stethoscope 200 can be configured to move from the STANDBY mode 242 to the ON mode 240 or to the OFF mode 238. The stethoscope 200 can be configured to be manually moved 260 by the user from the STANDBY mode 242 to the ON mode 240, e.g., by the user giving the knob 202 two quick downward taps. The user can thus prepare the stethoscope 200 for use when the user is ready. The stethoscope 200 can be configured to be manually moved 262 by the user from the STANDBY mode 242 to the OFF mode 240, e.g., by the user giving the knob 202 four or five quick downward taps. In addition, the stethoscope 200 can be configured to automatically move 264 to the OFF mode 238 from the STANDBY mode 242, which may help conserve power and/or processor resources during lack of stethoscope 200 use. In some embodiments, the stethoscope 200 can be configured to be only manually movable from the STANDBY mode 242 to the OFF mode 238 or to be only automatically movable from the STANDBY mode 242 to the OFF mode 238.

Figure 16B:
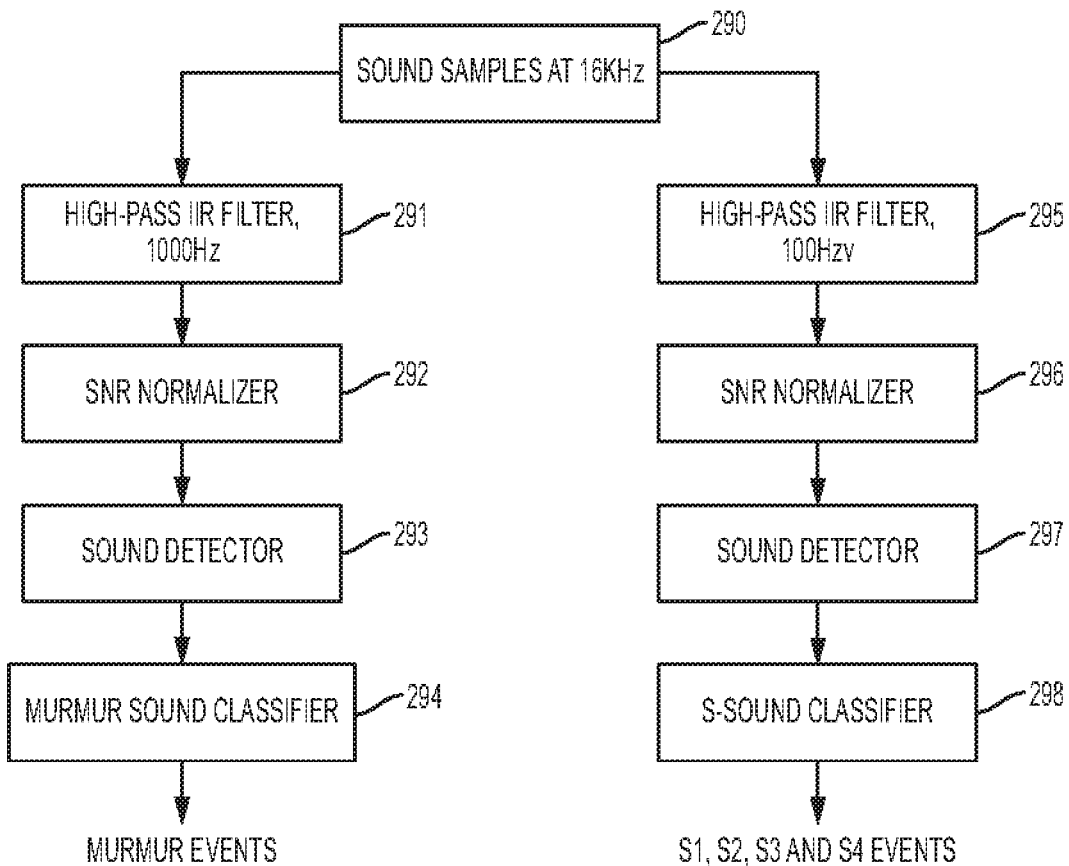
FIG. 16B is a flowchart of sound analysis of the stethoscope of FIG. 14.

Gathered cardiac body sounds can be analyzed in a variety of ways. FIG. 16B illustrates an embodiment of cardiac sound analysis that the processor 214 can perform with respect to audio gathered by the at least one microphone 218. Other stethoscopes described herein can have their gathered audio subjected to similar cardiac sound analysis. In general, the processor 214 can be configured to process sound in real time with its gathering for detection of a heart murmur and for detection of SI (first heart sound), S2 (second heart sound), S3 (third heart sound or protodiastolic gallop), and S4 (fourth heart sound or presystolic gallop) heart sound events. The vibrator 216 and the one or more lights 215 can be configured to provide output in response to the detected murmur and/or the detected SI, S2, S3, and S4 events, as discussed herein, such as by the one or more lights 215 pulsing in accordance with the detected heart rate. Other stethoscopes described herein can be configured to similarly process sound.

The at least one microphone 218 can be configured to gather sound samples 290 at 16 kHz and provide the gathered data to the processor 214. The stethoscope 200 can include an analog/digital (A/D) converter, which alone or with a pick-up of the at least one microphone 218, to convert the gathered audio sounds to a digital signal that the processor 214 can process. To detect a heart murmur, the processor 214 can be configured to process the received data through 291 a high-pass infinite impulse response (IIR) filter (e.g., a high-pass Butterworth IIR filter) with a cutoff frequency set at 1000 Hz, through 292 an SNR normalizer to normalize the filtered sound, through 293 a sound detector to combine the sample SNR values previously calculated 291, 292 into isolated sounds (e.g., to combine two sounds within a predetermined time period into a single sound), and through 294 a murmur sound classifier to determine whether any of the isolated sounds are indicative of a murmur based on, e.g., any combination of historical data for the subject, historical data for a plurality of subjects, length of the sound, amplitude of the sound, relation between detected individual sounds such as distance in time between the currently analyzed sound and one or more previous sounds, etc. To detect S-sounds, the processor 214 can be configured to process the received data through 295 a high-pass IIR filter with a cutoff frequency set at 100 Hz to eliminate at least some of the low frequency noise and to bring out S-sounds of the heart by increasing their signal to noise ratio (SNR), through 296 an SNR normalizer to normalize the filtered sound, through 297 a sound detector to combine the sample SNR values previously calculated 295, 296 into isolated sounds, and through 298 a sound classifier to determine whether any of the isolated sounds are indicative of any of an SI, S2, S3, or S4 event based on, e.g., any combination of historical data for the subject, historical data for a plurality of subjects, length of the sound, amplitude of the sound, relation between detected individual sounds such as distance in time between the currently analyzed sound and one or more previous sounds, etc.

Also or instead of processing sound in real time, the sound can be processed later (e.g., not in real time), which may allow for more robust analysis and/or for comparison with data not available to the processor 214 in real time. A sampling rate of the gathered data can be used as a time reference for the gathered sound, which may facilitate analysis of the data in real time with the gathering and after the gathering since it can be known at which time the sound was gathered.

Gathered respiratory sounds can be analyzed in a variety of ways. As will be appreciated by a person skilled in the art, heart rate is related to breathing rate, with heart rate naturally varying during a breathing cycle (respiratory sinus arrhythmia (RSA)). The stethoscope 200 can gather cardiac sounds, as discussed herein, and the gathered cardiac sounds can be used to determine respiratory rate since a correlation exists between heart rate variability in the heart beat and heart rate. In other words, heart rate can be used to determine inspiration and expiration, the phases of respiration, which can then be used to determine respiratory rate. Other stethoscopes described herein can have their gathered audio subjected to similar respiratory sound analysis.

Respiratory sounds can be initially processed similar to that discussed above regarding FIG. 16B and the processing of cardiac sounds. Namely, sound samples 290 can be sampled at 16 kHz, the received data can be processed through 295 a high-pass IIR filter with a cutoff frequency set at 100 Hz to eliminate at least some of the low frequency noise and to bring out breathing sounds of the lungs by increasing their SNR, processed through 296 an SNR normalizer to normalize the filtered sound, processed through 297 a sound detector to combine the sample SNR values previously calculated 295, 296 into isolated sounds, and through 298 a sound classifier to determine whether any of the isolated sounds are indicative of inspiration and expiration via S1 and S2 patterns in the gathered sound. An interval (Ti) can be measured between peaks in the S1/S2 heart rate cycle, and the respiration rate can be defined as 60/Ti.

The stethoscope 200 can be configured to confirm the respiratory rate determined using cardiac sounds in any of one or more additional ways. The respiratory rate, confirmed through multiple methods, may therefore be more accurate. Additional ways in which respiratory rate can be determined include using data gathered from a spirometer such as a peak flow spirometer, using body sound data gathered by the stethoscope's one or more microphones to identify sounds of inspiration, exhalation, and possible breathing anomalies, and using a gyroscope and accelerometer. The spirometer may also allow estimation of lung volume for each of the inspiration and expiation phases.

Figure 17A:
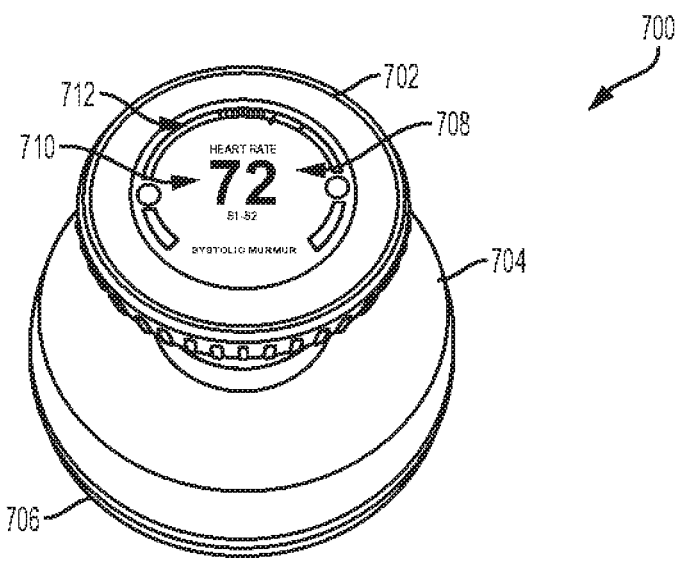
FIG. 17A is a perspective view of another embodiment of a stethoscope, the stethoscope including a display thereon.

FIG. 17A illustrates yet another embodiment of a stethoscope 700. The stethoscope 700 can generally be configured and used similar to the stethoscope 10 of FIGS. 1 and 2, e.g., can include a knob 702, a hollow body 704, a rotary potentiometer (not shown), a base 706, a USB port (not shown), and a circuit board (not shown) having electronic components mounted thereon or otherwise attached thereto, etc. The stethoscope 700 in this illustrated embodiment includes a display 708 thereon. The display 708 can, as discussed above with respect to the stethoscope 10 of FIG. 1, include any type of display, such as an LED display, Smart watch type OLED display, etc. As in this illustrated embodiment, the display 708 can be on a top (proximal) surface of the knob 702, which may facilitate visualization of the display 708 when the stethoscope 700 is in use, e.g., when the base 706 contacts a subject.

Figure 17B:
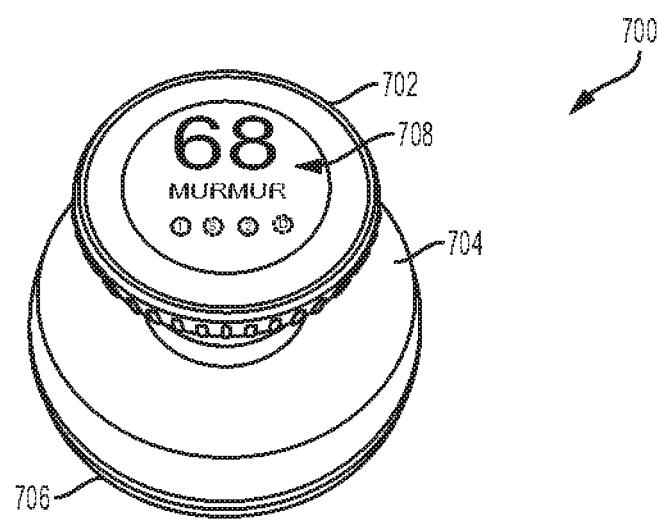
FIG. 17B is a perspective view of the stethoscope of FIG. 17A with different information shown on the display than in FIG. 17A.

FIG. 17A shows the display 708 displaying information indicative of gathered heart sounds via one embodiment of an interface. The stethoscope 700 can be configured to gather heart sounds and/or other types of body sounds, as discussed herein. The information in this illustrated embodiment includes a heart rate 710 of the subject and a "circle display" 712 providing real time cardiac data, which in this illustrated embodiment includes an indication of a systolic murmur between SI and S2. Configurations of the circle display 712 are discussed further below, e.g., with respect to the embodiment of FIG. 79. FIG. 17B shows the display 708 displaying information indicative of gathered heart sounds via another embodiment of an interface.

A head of a stethoscope can be configured to be removably and replaceably coupled to a distal remainder of the stethoscope. Such removability and replaceability may facilitate repair of the stethoscope, may facilitate cleaning of the stethoscope, and/or may allow the head to be coupled to another stethoscope (e.g., a distal portion of another stethoscope) or to an external electronic device, which may allow for more versatile use of the head. In an exemplary embodiment, the external electronic device configured to removably and replaceably couple to the head can include a wearable electronic device such as a Smart watch or a belt configured similar to a Smart watch.

Figure 17C:
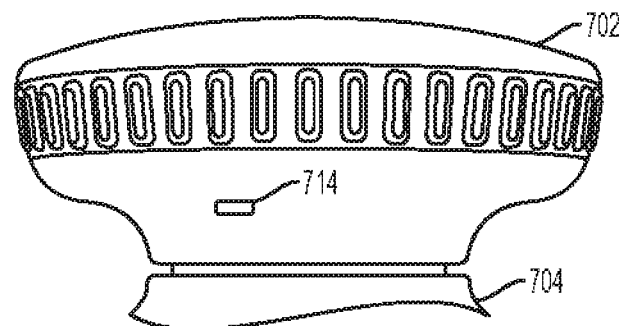
FIG. 17C is a side schematic view of a proximal portion of the stethoscope of FIG. 17A.
Figure 17D:
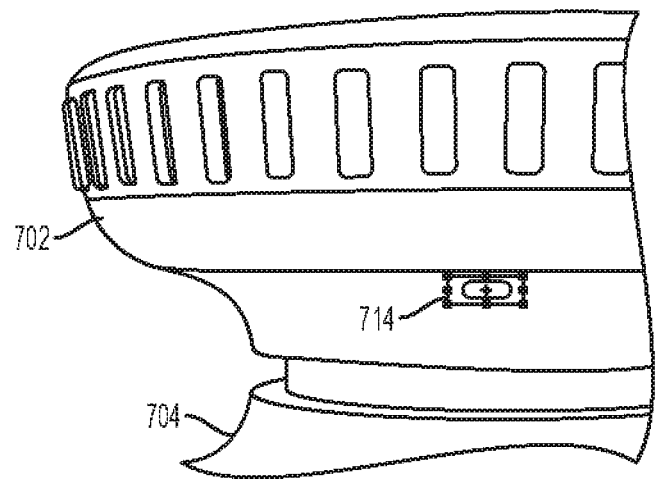
FIG. 17D is a side perspective view of a portion of the proximal portion of the stethoscope of FIG. 17A.
Figure 17E:
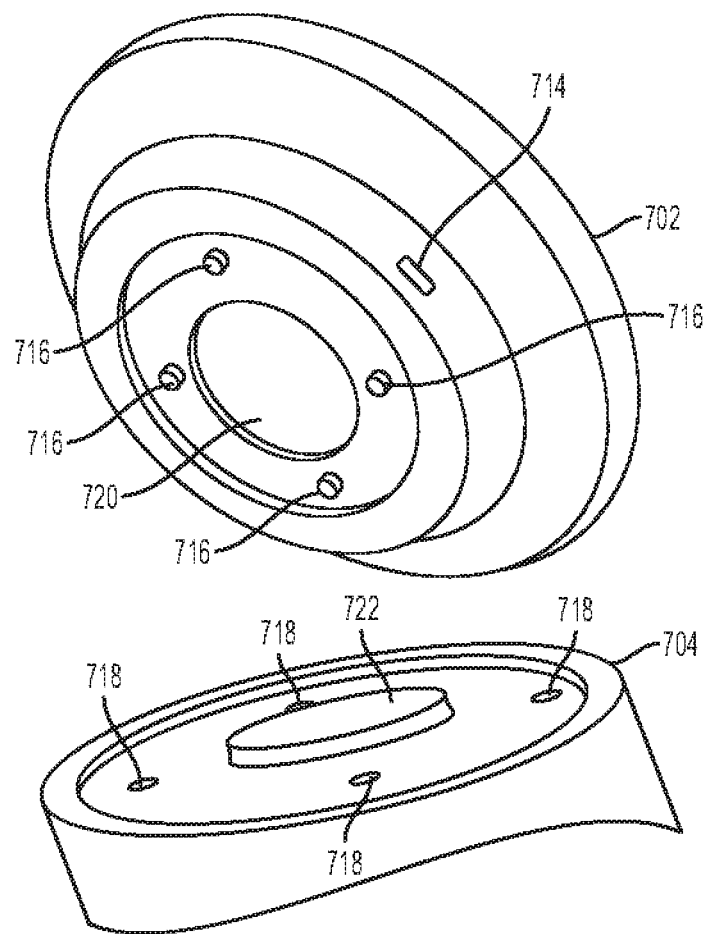
FIG. 17E is a perspective schematic view of a head of the stethoscope of FIG. 17A and a portion of a distal portion of the stethoscope of FIG. 17A.

The head 702 of the stethoscope 700 of FIG. 17A, which is also shown in FIGS. 17C-17E, is one example of a head configured to be removably and replaceably coupled to a distal portion of the stethoscope, e.g., to the body 704 and the base 706 of the stethoscope 700. The head 702 can be configured to be released from the distal portion of the stethoscope 700 in a variety of ways. As in this illustrated embodiment, the head 702 can include a push button 714 configured to be depressed to release the head 702 from the distal portion of the stethoscope 700, e.g., to release the head 702 from the body 704 to which the head 702 can be directly attached.

The head 702 can be configured to be removably and replaceably coupled to the distal portion of the stethoscope 700 via a release mechanism. As in this illustrated embodiment, the release mechanism can include a magnetic connector. The head 702 can include one or more magnetic elements 716 (four magnetic elements 716 in this illustrated embodiment) configured to magnetically engage one or more corresponding magnetic contacts 718 (four magnetic contacts 718 in this illustrated embodiment) on the distal portion of the stethoscope 700, e.g., on the body 704, and the head 702 can include one or more magnetic contacts 720 (one magnetic contact 720 in this illustrated embodiment) configured to magnetically engage one or more corresponding magnetic elements 722 (one magnetic element 722 in this illustrated embodiment) on the distal portion of the stethoscope 700, e.g., on the body 704. The magnetic elements 716, 722 can be configured to attract their respective magnetic contacts 718, 720 thereto to keep the head 702 coupled to the distal portion of the stethoscope 700 until actuation of the release mechanism (e.g., until the push button 714 is pushed). The actuation of the release mechanism can be configured to "break" the magnetic force to allow release of the head 702 from the stethoscope's distal portion.

Figure 17F:
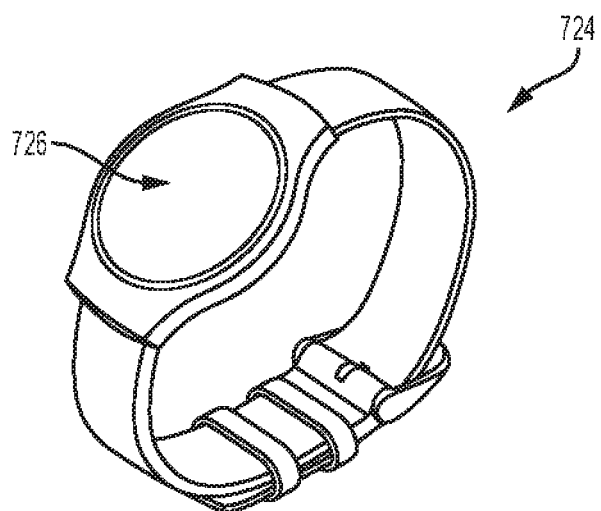
FIG. 17F is a perspective view of one embodiment of a wearable electronic device configured to couple to a head of a stethoscope.

As mentioned above, a head of a stethoscope can be configured to be removably and replaceably coupled to an external electronic device. FIG. 17F illustrates one embodiment of such an external electronic device, a Smart watch 724 configured to have a head of a stethoscope, e.g., the head 702 of the stethoscope 700 of FIG. 17A, removably and replaceably coupled to a face 726 thereof. The face 726 can, similar to the distal portion of the stethoscope 700, include one or more magnetic contacts configured to magnetically engage the head's one or more magnetic elements 716 and one or more magnetic elements configured to magnetically engage the head's one or more magnetic contacts 722.

The stethoscopes described herein can be made from any one or more of a variety of materials. In at least some embodiments, all or a substantial portion of a stethoscope can be made from stainless steel, which may provide durability to the stethoscope and/or facilitate its cleaning. In at least some embodiments, all or a substantial portion of a stethoscope can be made from aluminum anodised or plastic, which may allow the stethoscope to be manufactured at a lower cost than a metallic (e.g., stainless steel, etc.) stethoscope and thus be more easily obtainable by doctors and/or other users in particularly cost-conscious markets.

Figure 18:
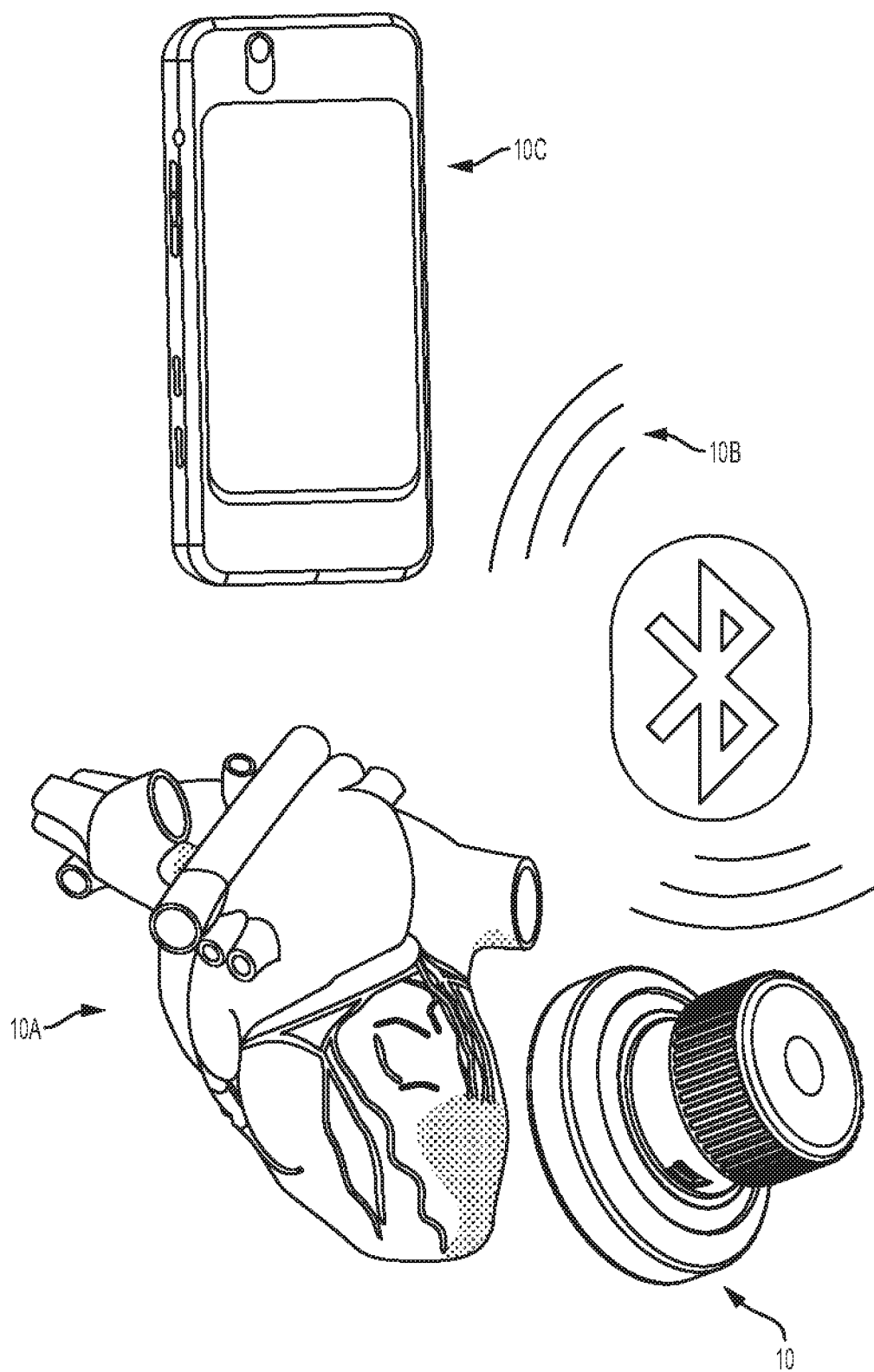
FIG. 18 is a perspective view of a system including the stethoscope of FIG. 1.

The stethoscopes described herein can be configured to electronically connect to one or more additional devices via a wired communication link, such as via a wired USB connection, and/or via a wireless communication link, such as via Bluetooth. FIG. 18 illustrates an embodiment of a wireless communication link between the stethoscope 10 of FIGS. 1 and 2 with a cell phone 10C via Bluetooth 10B. FIG. 18 also illustrates a heart 10A of a subject (not shown) whose sounds the stethoscope 10 can be configured to detect. Although FIG. 18 shows the stethoscope 10 of FIGS. 1 and 2, other stethoscopes described herein can be similarly linked. The cell phone 10C can have an APP installed thereon configured to, as discussed further below, display a waveform of the audio signal gathered and processed by the stethoscope 10 and to display other data analytics sent from the stethoscope 10. The APP can be configured to control the configuration and set up of the stethoscope 10. By accessing the settings on the APP these changes can be passed on to hardware associated with stethoscope 10, e.g., to the processor 27 that can cause the requested changes to occur. The APP can be configured to allow the user to change settings of the stethoscope's hardware. For example, the APP can be configured to allow the user to change the rate of the heart rate that triggers colors of the at least one light. The APP can be configured to allow the user to turn off the one or more lights if required, turn off vibration, or turn off audio signals. Alternatively, instead of having the APP installed thereon, the cell phone 10C can access a web page through which similar functionality can be achieved.

In the case of a wireless communication link, a stethoscope can be configured to automatically detect a device once the device moves in close enough proximity to the stethoscope. For example, the stethoscope can be configured to read a chip (e.g., an identification microchip implanted in an animal, a radio frequency identification (RFID) tag storing patient information, etc.) when the stethoscope is moved into proximity of the device. The stethoscope can thus be configured to identify the subject on which the stethoscope is to be used, which may facilitate comparison of newly gathered data with historical data for the subject and/or may allow the stethoscope to provide more accurate output regarding abnormality of detected sounds since currently gathered data for the patient can be compared with historical data for the patient. For another example, the stethoscope can be configured to automatically connect to the most recently connected device when the most recently connected device moves into range of the stethoscope. For yet another example, the stethoscope can be configured to automatically connect to any device to which the stethoscope was previously connected when the previously connected device moves into range of the stethoscope.

The stethoscopes described herein can be configured for use on human subjects and on animal subjects. For example, in the case of an animal, a user can use a stethoscope directly on the animal in the same way the stethoscope would be used directly by the user on a human. For another example, a user can use a stethoscope on a pregnant woman to detect heart sounds and/or respiratory sounds of the fetus. For still another example, a non-medically trained user can use a first stethoscope on a subject at a home of the subject, and a medically trained user can use a second stethoscope linked to the first stethoscope. The medically trained user may thus be able to interpret detected bodily sounds without the medically trained user being physically proximate to the subject. For yet another example, in the case of an animal, a handler of the animal (e.g., a zookeeper, an animal trainer, etc.) can use a first stethoscope on the animal. A second stethoscope can be linked (e.g., electronically connected) to the first stethoscope such that in real time the first and second stethoscopes can generate the same output, e.g., same haptic response to representative raw data signals, same illuminated response to the representative raw data signals, and/or same audio response to the representative raw data signals. The animal may thus be approached by the handler, who is typically a person known to the animal, and accordingly be more likely to be calm and/or allow use of the stethoscope thereon. The handler using the first stethoscope need not be able to interpret the output of the first stethoscope at all and/or in real time with the output since the user of the second stethoscope, e.g., a medically trained person, can receive the same output and interpret the output as needed. The user of the second stethoscope need not be in proximity of the animal to receive the output via the second stethoscope, which may help provide user safety, particularly in the case of more dangerous and/or unpredictable animals and/or in the case of nervous users.

The stethoscopes described herein can be configured to facilitate medical education. For example, in the case of either a human subject or an animal subject, a teacher, professor, or other educator can use a first stethoscope on a subject. Each of one or more students can have a stethoscope linked to the first stethoscope. Each of the student(s) can thus receive the same real-time output from their individual stethoscopes as the real-time output from the first stethoscope. The student(s) may thus learn how to properly interpret the output of the stethoscope based on commentary and instruction from the educator and thus be better able to treat future subjects. The student(s) may be in the same classroom as the educator, but any one or more of the students can be remotely located from the educator since the linked stethoscopes need not be physically near each other to provide the same outputs as one another, which may allow more students to have access to and receive education.

The stethoscopes described herein can be configured to facilitate analysis of an effect of a subject's location on the subject's breathing. As discussed herein, a stethoscope can be configured to facilitate determination of respiratory rate and detection of possible breathing anomalies. Using this information with one or more location-specific factors of the subject at the time the stethoscope gathers information, the effect of a subject's location on the subject's breathing can be evaluated. For example, a subject may be with a Smart phone or other portable electronic device configured to detect one or more factors specific to the subject's current location, such as geo-location (e.g., using a mobile phone's GPS functionality, etc.), ambient temperature, pollen count, UV index, wind speed, wind direction, humidity, pollution index, and altitude. The data gathered for these factors can be time-stamped such that the gathered factor data can be time-matched to gathered respiratory sound data to facilitate evaluation of the effect of the subject's location on breathing. The stethoscope can be configured to receive the data gathered for these factors, e.g., via a wired or wireless communication link, and be configured to perform this analysis. Additionally or alternatively, an off-board processor can be configured to perform this analysis.

The stethoscopes described herein can be configured to facilitate determining the severity of a subject's asthma attacks or pneumonia infection. A baseline of the patient's breathing can be established over time can be established using data gathered from a stethoscope so as to allow comparison of data thereto in the event of anomalies subject conditions such as asthma attacks or pneumonia.

The stethoscopes described herein can be used in a variety of ways. FIGS. 19-22 illustrate embodiments of using the stethoscope 10 of FIGS. 1 and 2. Although these uses are described with respect to the stethoscope 10 of FIGS. 1 and 2, other stethoscopes described herein can be similarly used.

Figure 19:
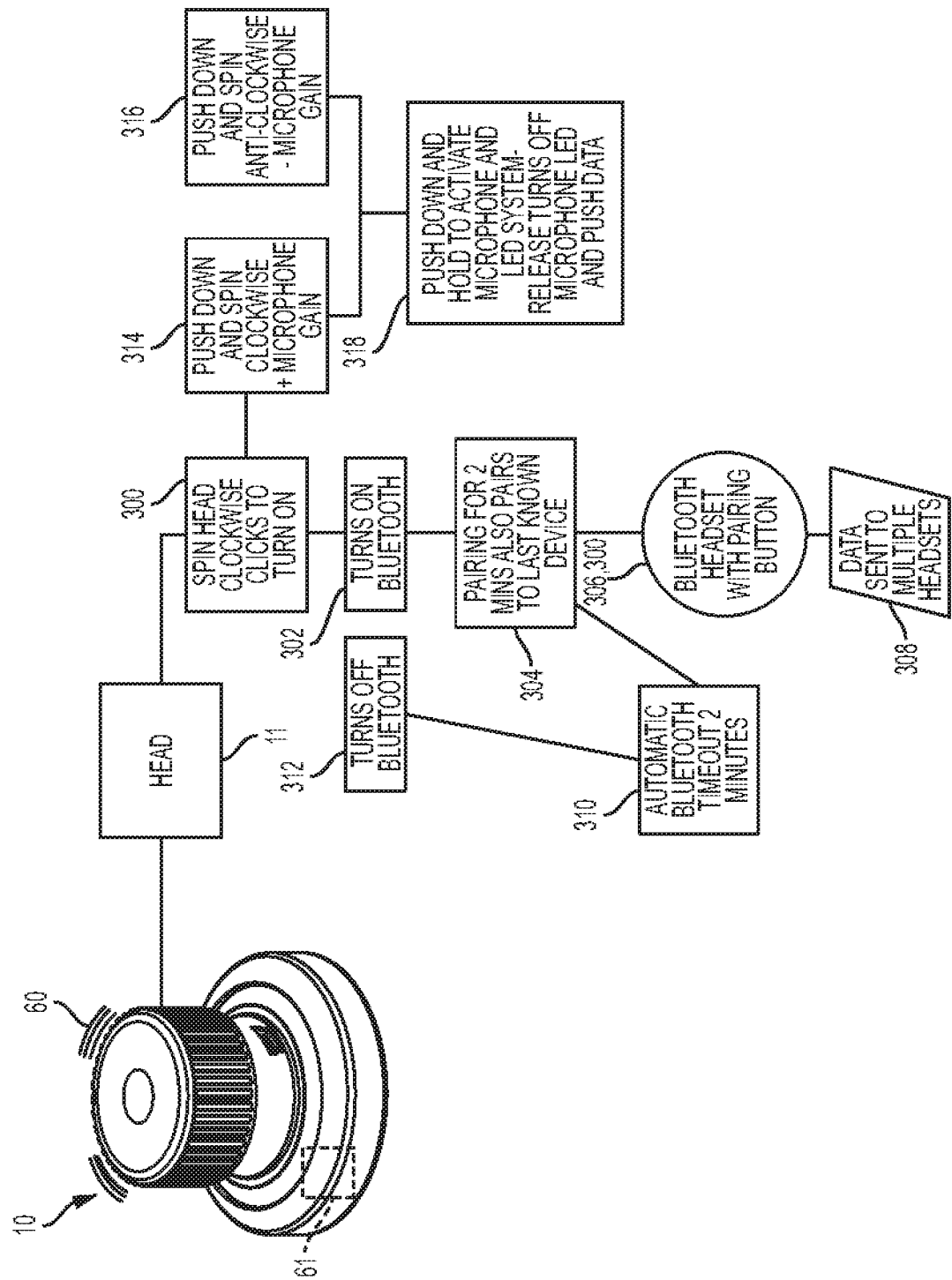
FIG. 19 is a schematic flowchart illustrating one embodiment of using the stethoscope of FIG. 1.

As shown in FIG. 19, the knob 11 (also referred to herein as a "head") can be rotated 300 (e.g., spun) in a first direction (e.g., clockwise) to turn the stethoscope 10 on, e.g., move the stethoscope 10 from an OFF mode to an ON mode, and to turn on 302 Bluetooth, e.g., to activate the Bluetooth chip 28. With Bluetooth on, the stethoscope 10 can pair for a predetermined amount of time (e.g., two minutes) with an external electronic device, such as by automatically pairing 304 with the external electronic device most recently linked to the stethoscope 10, by manually pairing 306 with a Bluetooth headset upon actuation (e.g., pushing) of a pairing button on the headset or the stethoscope 10, and/or by manually or automatically pairing 308 with multiple Bluetooth headsets. Automatic pairing such as the pairing 304 with the most recent device can be automatically terminated 310 after elapse of a predetermined amount of time (e.g., two minutes) and thereby turn off 312 Bluetooth, e.g., de-activate the Bluetooth chip 28.

With the stethoscope 10 on, the knob 11 can be pushed down to activate the at least one microphone and the at least one light. With the knob 11 held down, the knob 11 can be selectively rotated 314 in a first direction (e.g., clockwise) to increase microphone gain and rotated 316 in a second, opposite direction (e.g., counterclockwise) to decrease microphone gain. Releasing 318 the knob 11 can cause the knob 11 to move up (proximally), due to its biased nature, and thereby deactivate the at least one microphone and the at least one light. The release 318 can be configured to trigger the processor 27 to transmit to an external electronic device data generated and/or gathered by the at least one microphone during the immediately preceding listening session. At least some of the data transmitted, such as the gain(s), can be processed by a DSP, e.g., the amplifier 25, before being transmitted.

Figure 20:
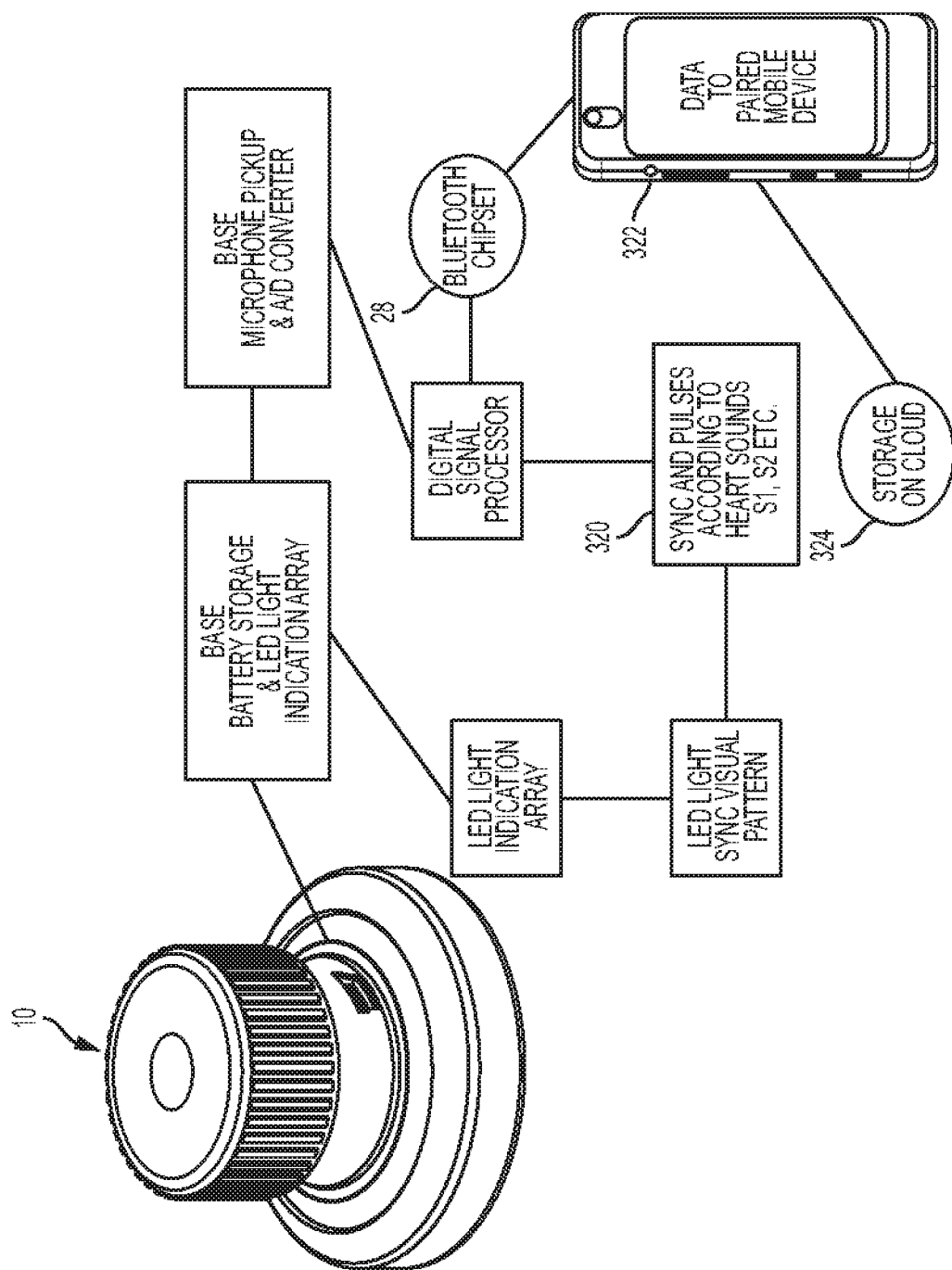
FIG. 20 is a schematic flowchart illustrating another embodiment of using the stethoscope of FIG. 1.
Figure 21:
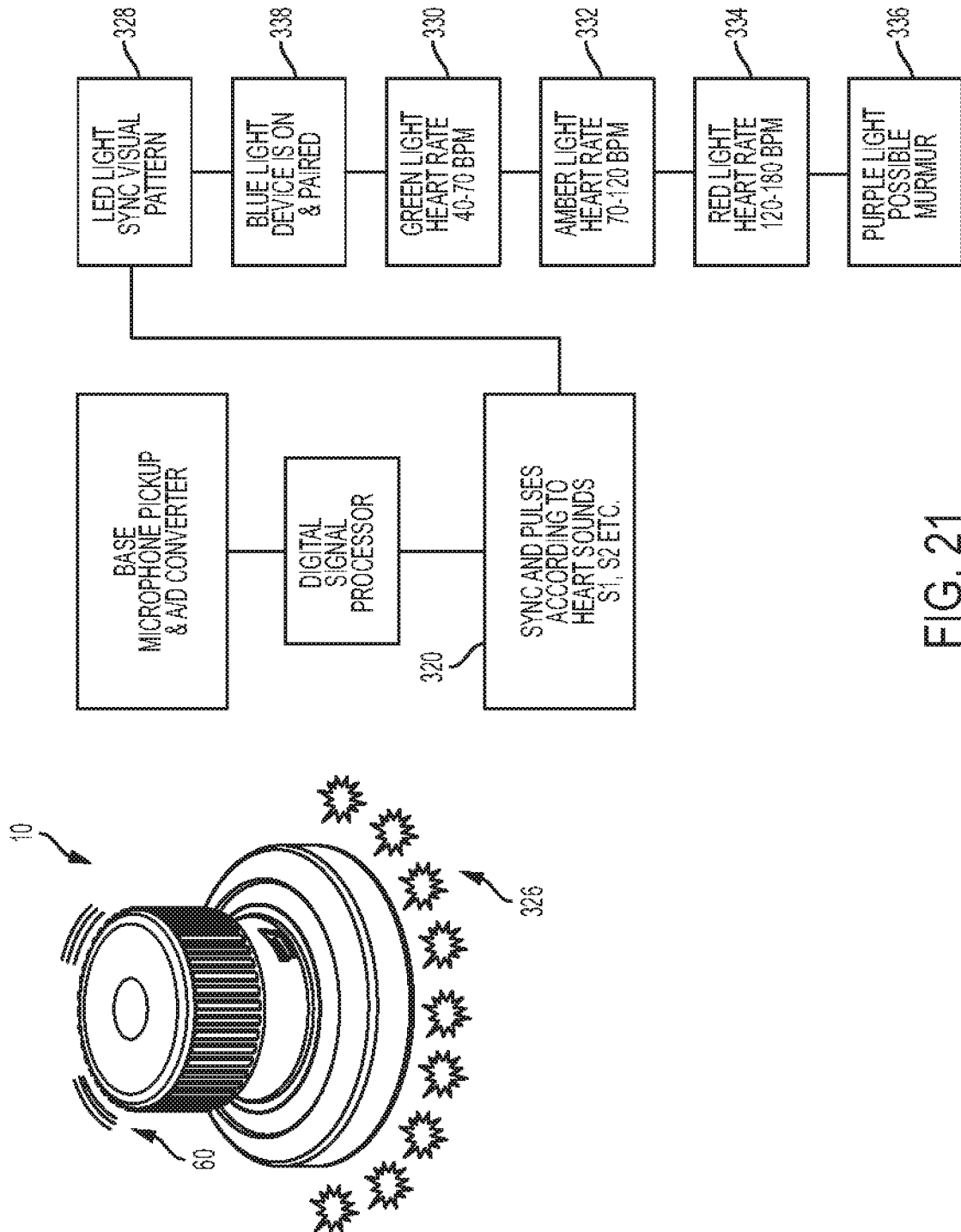
FIG. 21 is a schematic flowchart illustrating yet another embodiment of using the stethoscope of FIG. 1.

The knob 11 can be pushed down with the exterior distal surface base 13 of the stethoscope 10 positioned on a target skin surface area of a subject, e.g., an area adjacent a heart of the subject or an area adjacent a lung of the patient. As shown in FIG. 20, sound from within the subject at the target area at which the stethoscope 10 is positioned can be picked up via the at least one microphone and microphone pick up 51. The gathered sounds can be transmitted to and processed under instruction of the processor 27, e.g., to remove noise, to combine sounds as needed, etc. The processor 27 can cause the LEDs 33, 34, 35, 36, 37, 38, 39 and 40 to pulse (spin) 320 in sync with the gathered sounds, which include heart sounds SI, S2, etc. in this illustrated embodiment in which the stethoscope 10 is positioned adjacent (e.g., above) the subject's heart. As shown in FIG. 21, the LEDs 33, 34, 35, 36, 37, 38, 39 and 40 can illuminate 326 in a spin pattern 328 (e.g., successive ones of the lights being illuminated in a track-like pattern) in a first color (e.g., green) 330 for a heart rate of 40-70 bpm, a second color (e.g., amber) 332 for a heart rate of 70-120 bpm, a third color (e.g., red) 334 for a heart rate of 120-180 bpm, and a fourth color (e.g., purple) 336 for a possible heart murmur. FIG. 21 also illustrates the vibration of the knob 11, as indicated by the sound lines 60, in sync with the gathered sounds and hence also in sync with the at least one light.

FIG. 21 also shows that, prior to the at least one light's synced illumination, the LEDs 33, 34, 35, 36, 37, 38, 39 and 40 can illuminate 338 (e.g., blink, spin, or be steady) in a fifth color (e.g., blue) to indicate that the processor 27 is on and paired with the external electronic device 322 and is transmitting data thereto. In an exemplary embodiment, the LEDs 33, 34, 35, 36, 37, 38, 39 and 40 can illuminate 338 spin in the fifth color during pairing to indicate a search mode until a connection is established, at which time the synced illumination 326 may begin.

The processor 27 can be configured to cause the gathered sound data (raw and/or as processed by the processor 27) and/or the synced light color pattern to an external electronic device 322, which includes a mobile phone in this illustrated embodiment, via Bluetooth using the Bluetooth chip 28. In an exemplary embodiment, the data is transmitted after the current session of the stethoscope's use is completed, e.g., after the knob 11 is released to turn off the at least one microphone, which may help maximize and amount of capabilities available on board the stethoscope 10 to handle the gathering and analyzing of sound data. In other embodiments, the data can be transmitted in real time with its gathering and analysis or in batches during the current session of stethoscope 10 use. The external electronic device 322 can cause the received sound data to be stored 324 in a cloud based system, website, and/or other storage system for archiving and/or for further analysis.

Figure 22:
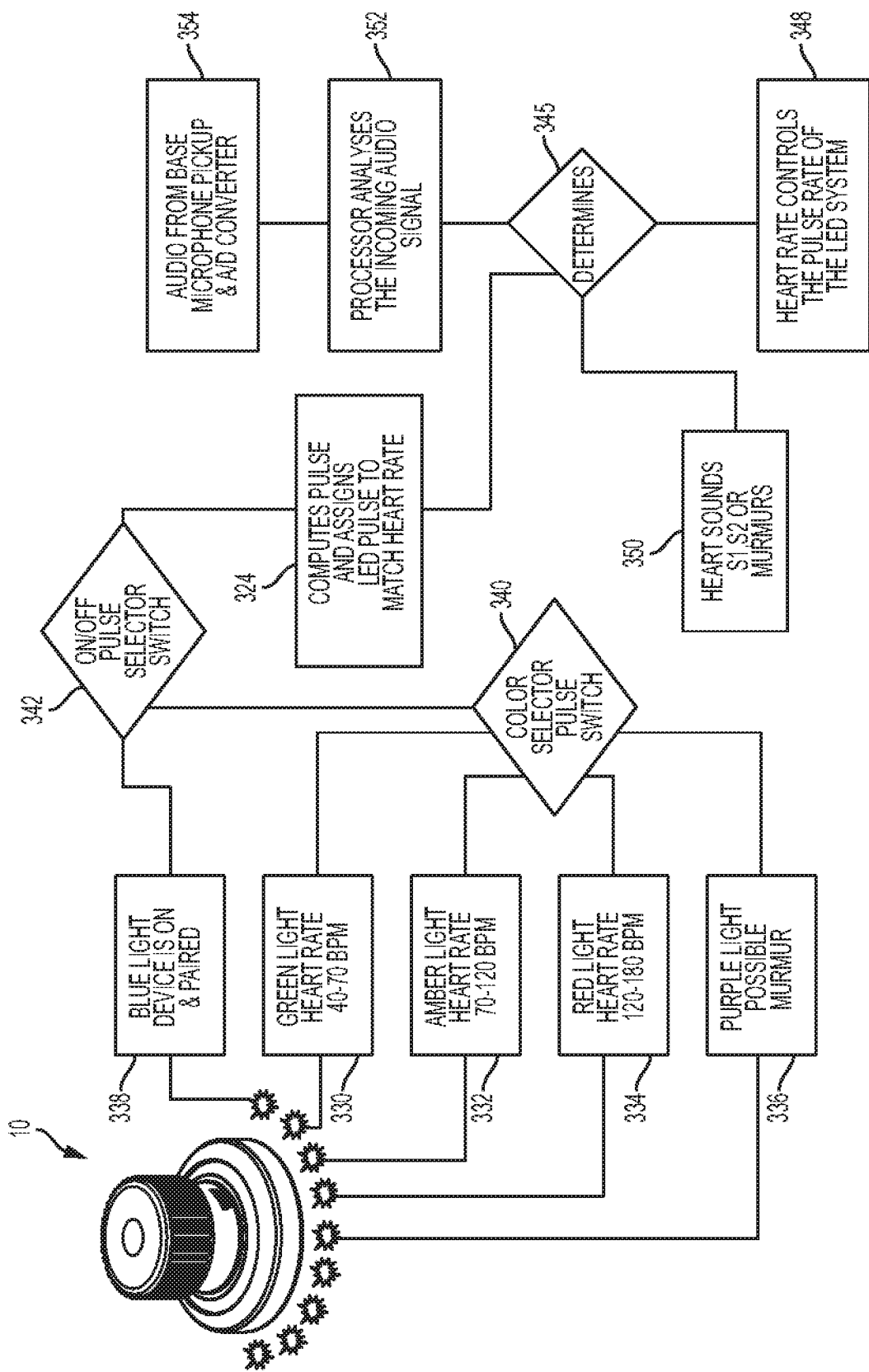
FIG. 22 is a schematic flowchart illustrating still another embodiment of using the stethoscope of FIG. 1.

As shown in FIG. 22, the stethoscope 10 can include a color selector pulse switch 340 and an ON/OFF pulse selector switch 342 that can be coupled to the color selector pulse switch 340. The color selector pulse switch 340 and the ON/OFF pulse selector switch 342 can be configured to allow color selection by a user of the colors used to indicate various statuses related to the gathered sounds. The colors can be set to an initial default that can be changed as desired by the user. The at least one light indicating ON/OFF and pairing status of the stethoscope 10 can be controlled via the ON/OFF pulse selector switch 342. The ON/OFF pulse selector switch 342 can be configured to be controlled by the external electronic device 322 paired with the stethoscope 10, e.g., with an APP installed on the external electronic device 322 or via web page accessed by the external electronic device 322, and/or controlled by the processor 27, e.g., via a software application installed on the stethoscope 10. The at least one light indicating gathered sounds can be controlled via the color selector pulse switch 340. The color selector pulse switch 340 can allow a user to select the ranges for various conditions that may be indicated by the gathered sounds (e.g., heart bpm ranges for each of a plurality of light colors or number of breaths per minute for each of a plurality of light colors).

The processor 27 can be configured to compute 344 a pulse indicated by the gathered sounds (which as mentioned above include heart sounds in this illustrated embodiment) and assign a light pulse that matches subject's heart rate. The computed pulse and the gathered sounds 350 (e.g., gathered heart sounds SI, S2, murmur, etc.) determines 346 heart rate, which controls 348 the pulse rate of the at least one light. The processor 27 can also be configured to analyze 352 the gathered sounds 354, in addition to the external electronic device 322 being configured to analyze the gathered sounds received from the stethoscope 10.

Figure 23:
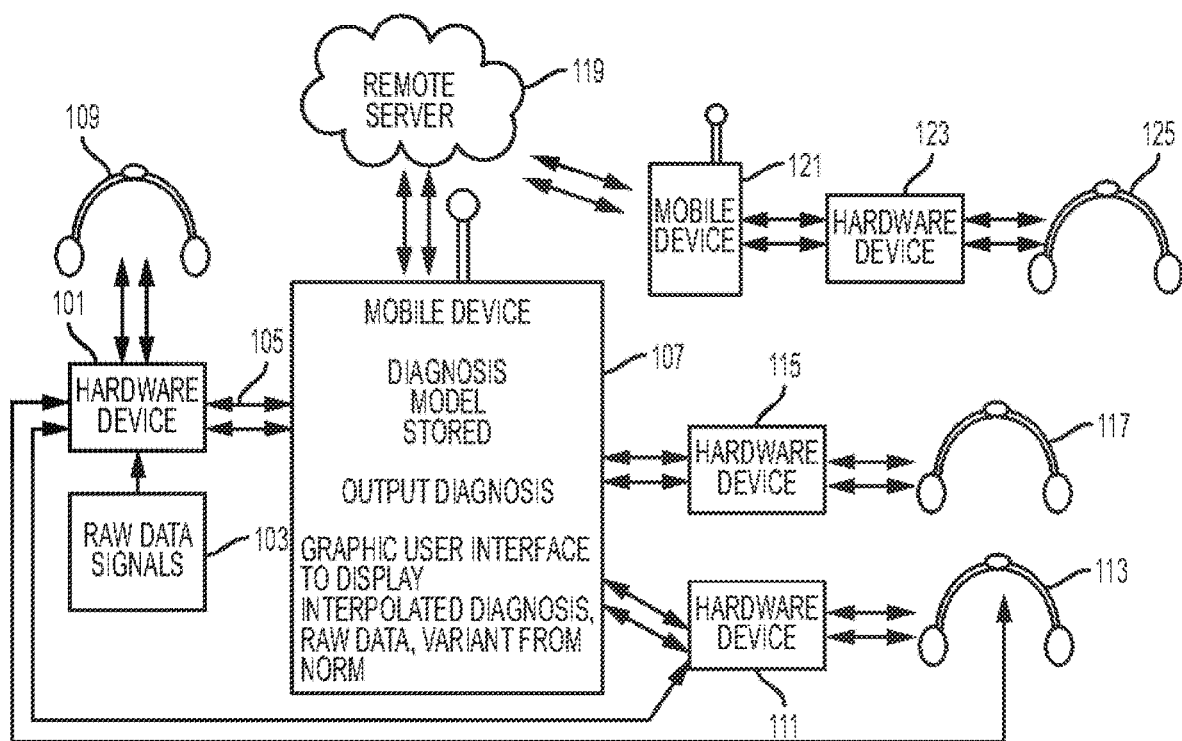
FIG. 23 is a schematic view of a system including a plurality of stethoscopes and a plurality of electronic devices.

FIG. 23 illustrates an embodiment of pairing (linking) arrangements and network configuration of a stethoscope (e.g., any of the stethoscopes described herein) and an electronic device external to the stethoscope. Stethoscopes are referred to "hardware devices" 101, 111, 115, 123 in FIG. 23, and the terms are used interchangeably herein. External electronic devices in FIG. 23 include Bluetooth headsets 109, 113, 117, 125 and mobile devices 107, 121, such as Smart phones, Smart watches, tablets, and laptops, but as mentioned above, external electronic devices paired with stethoscopes can be other types of electronic devices, such as non-mobile servers and non-mobile desktop computers. As shown in FIG. 23, a first hardware device 101 can be paired to a first headset 109, a second headset 113, a first mobile device 107, and a second hardware device 111; the second hardware device 111 can also be paired to the second headset 113 and to the first mobile device 107, a third hardware device 115 can be paired to a third headset 117 and to the first mobile device 107, and a fourth hardware device 123 can be paired to a fourth headset 125 and to a second mobile device 121. Thus, a stethoscope can be configured to be simultaneously paired with one or more external electronic devices (e.g., the first hardware device 101 being paired with both the first headset 109 and the first mobile device 107), and an electronic device can be configured to be simultaneously paired with one or more stethoscopes (e.g., the first mobile device 107 being paired with the first, second, and third hardware devices 101, 111, 115).

A stethoscope can be configured to pair (link) with one or more other stethoscopes. In this way, when one of the linked stethoscopes gathers data, the one or more others of the linked stethoscopes can receive the gathered data directly from the stethoscope that gathered the data, thereby allowing all of the stethoscopes to output the same sound, light, and/or vibration indicative of the sounds gathered by just one of the stethoscopes. For example, as shown in FIG. 23, the first hardware device 101 is paired with the second hardware device 111. Therefore, when the first hardware device 101 receives raw data signals representative of bodily characteristic (e.g., heart sounds, lung sounds, or other body sounds), and trans representative raw data signals, the second hardware device 111 can receive the representative raw data signals from the first hardware device 101. Therefore, the first hardware device 101 and the second hardware device 111 in real-time can generate the same output that can include a haptic response to the representative raw data signals, an illuminated response to the representative raw data signals, and/or an audio response to the representative raw data signals.

FIG. 23 also illustrates a remote server 119 that can be configured to be in electronic communication with an electronic device paired with a stethoscope, which may facilitate storage of historical data and/or secure backup of data. In this illustrated embodiment, the mobile devices 107, 121 are in electronic communication with the remote server 119. Thus, a remote server can be configured to electronically communicate with a plurality of electronic devices and thus be configured to receive data relating to a plurality of stethoscopes.

From a remote location, the first mobile device 107 and the second mobile device 121 can each be configured to download an application (APP) from the remote server 119, which can then be installed on the first mobile device 107 and the second mobile device 121, as will be appreciated by a person skilled in the art. The APP can facilitate the pairing of the mobile devices 107, 121 with one or more of the stethoscopes 101, 111, 115, 123. The first hardware device 101 can have associated therewith a first unique identifier, and the second hardware device 123 can have associated therewith a second unique identifier. The first mobile device 101 and the second mobile device 121 can be configured to transmit to the remote server 119 the first unique identifier and the second unique identifier, respectively. The APP can facilitate the establishment of links between the first hardware device 101 and the second hardware device 121 in a network according to the first unique identifier and the second unique identifier, respectively. According, data transfer can be provided via the network between the hardware devices 101, 111, 115 linked to the first mobile device 107 and the hardware device 123 linked to the second mobile device 121. Other forms of communication such as messaging (texting, emailing, etc.), voice, and video can also be enabled via the network. Thus, as discussed above, in a remote location, in real-time, the same immersive three-dimensional user experience of, for example, the first hardware device 101 and its paired headset 109 can be experienced via the fourth hardware device 123 and its paired headset 125.

In use, the first hardware device 101 can monitor at least one of heart sounds and lung sounds to generate raw data signals 103 that can include at least one of heart sound raw data signals and lung sound or other body sounds raw data signals. The sounds can be heard by first and second users via the first headset 109 and the second headset 113, respectively, and can be similarly output by sound, vibration, and/or light at the first hardware device 101 and the second hardware device 111 linked thereto. The second hardware device 111 can be remote from the first hardware device 101 since the pairing is electronic and can be remote via network connection. The first hardware device 101 can transmit at least one of the heart sound representative raw data signals and the lung sound representative raw data signals or other body sound signals via Bluetooth 105 to the first mobile device 107 linked to the first hardware device 101. The raw data signals can further include at least one of ECG signal, gyroscope signals, temperature signals, infrared signals and ultrasound signals and others as included. For example, accelerometer signals can provide patient positional information gained from the gyroscope signals.

As shown in FIG. 23, the first mobile device 107 can have a display device for generating an indicia of at least one of the representative raw data signals 105, an interpolation in a graphic form of the representative raw data signals 105 indicating characteristics determined from the representative raw data signals, and a diagnosis presented by the representative raw data 105 provided by subjecting the representative raw data 105 to a diagnosis model. Below are discussed various manners in which the representative data can be displayed on the first mobile device 107 (and on any other electronic device linked to a stethoscope providing representative data thereto). For example, below are shown an interpolation in a graphic form of representative raw data signals indicating characteristics determined from the representative raw data signals comprises color coded indicia of systole and a diastole events on a time line representative of timing of the systole and diastole events.

Figure 23B:
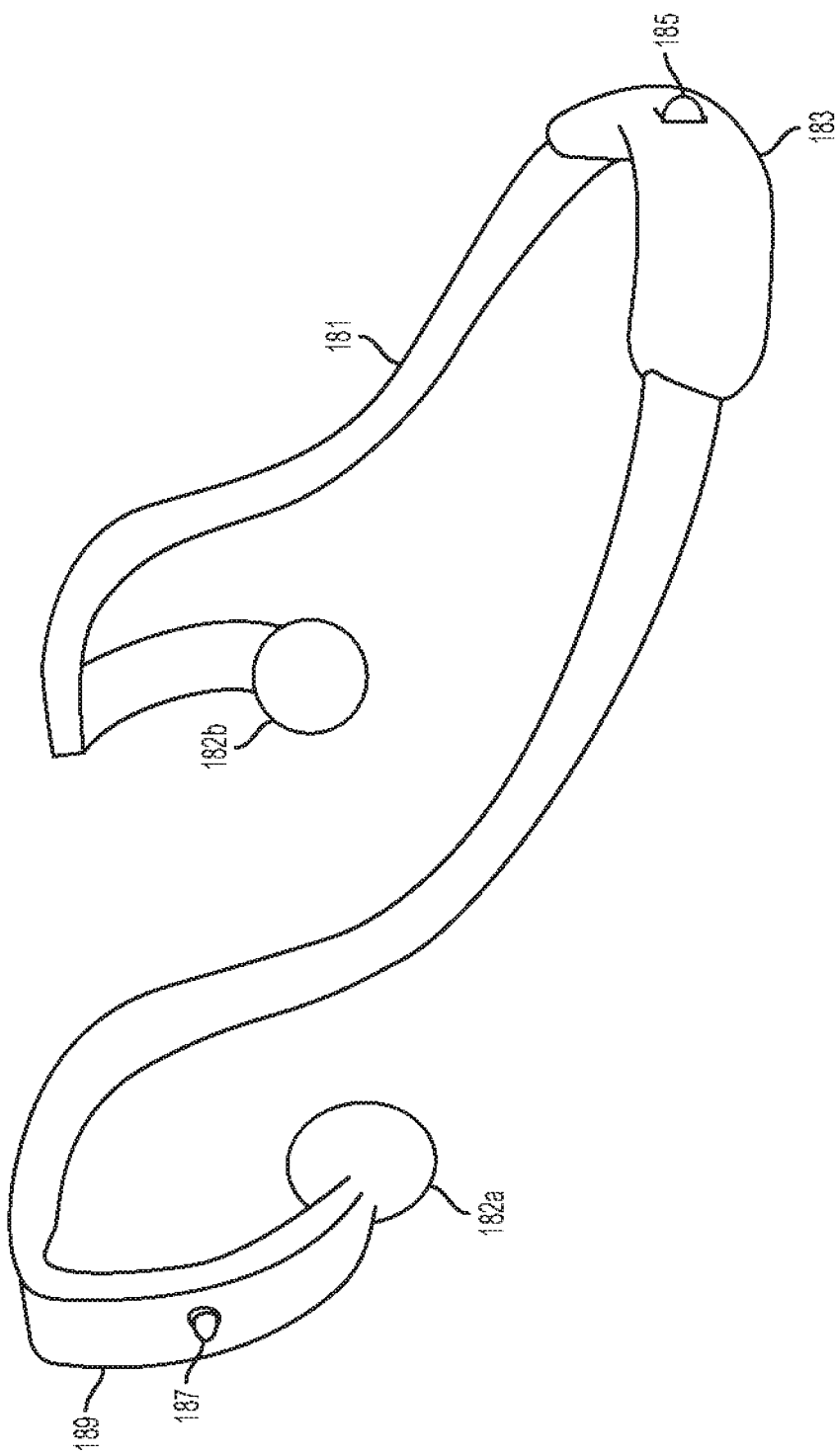
FIG. 23B is a perspective view of the headset of FIG. 23A.
Figure 23C:
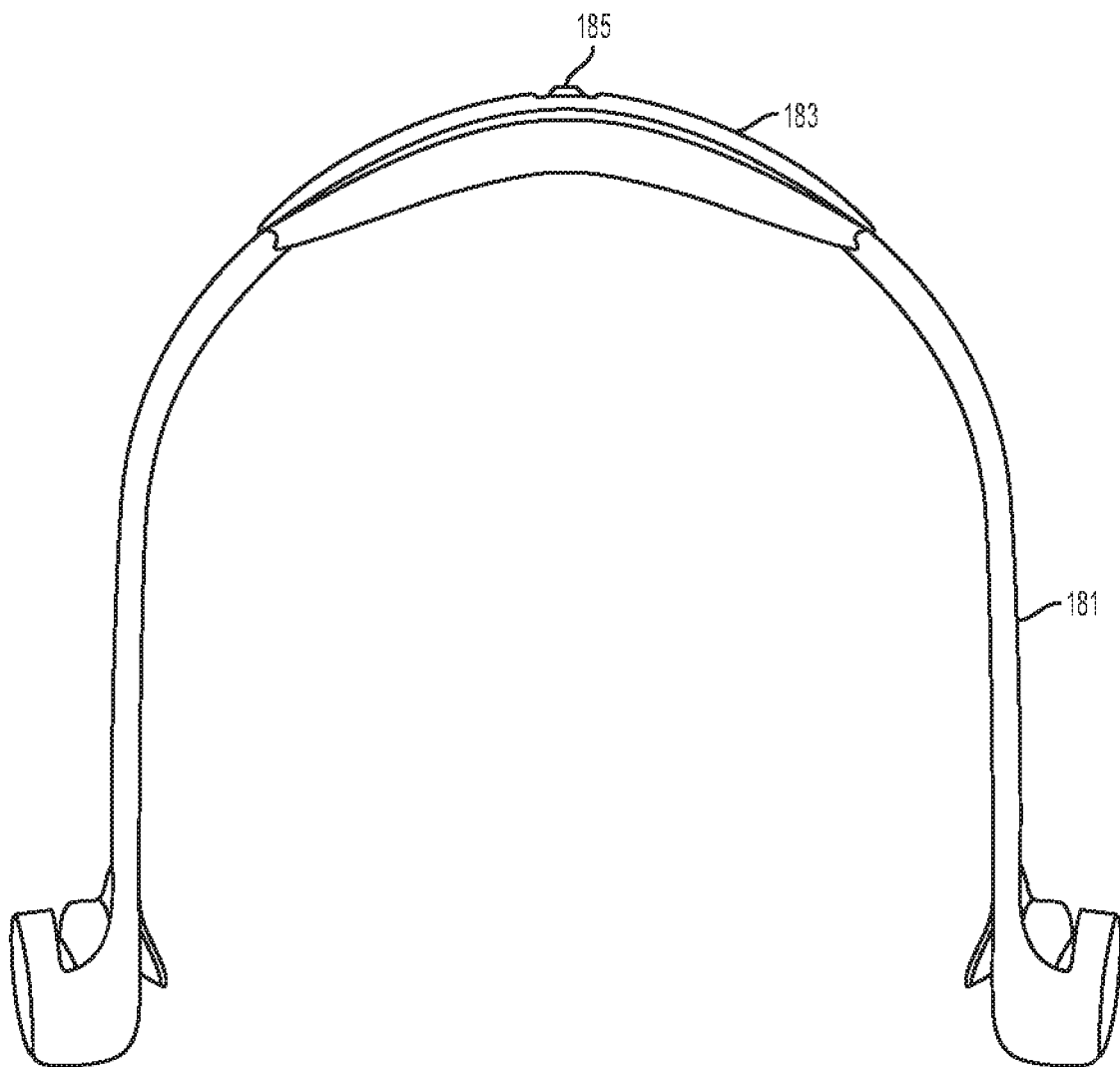
FIG. 23C is another end view of the headset of FIG. 23A.

The headsets 109, 113, 117, 125 of FIG. 23 can have a variety of configurations, as will be appreciated by a person skilled in the art. FIGS. 23A-23C illustrate one embodiment of a headset 181 that can be used as any one or more of the headsets 109, 113, 117, 125. The headset 181 of this illustrated embodiment is configured as a behind-the-neck headset 181 configured to receive data. The headset 181 can include a plurality of ear phones 182a, 182b, a behind-the-neck member 183 for supporting the ear phones 182a, 182b, and an outward facing LED 185 housed in the behind-the-neck member 183. When illuminated, the light of the LED 185 can be directed in an outward direction away from a user's neck when the headset 181 is worn by a user. The outward facing LED 185 can be in a low illumination mode when the headset 181 is not receiving data. The outward facing LED 185 can be in a high illumination mode when the headset 181 is receiving data. The headset 181 can include LEDs 187 housed on the ear phone's support housings 187a, 187b that can be in a low illumination mode when the headset 181 is not receiving data and that can be in a high illumination mode when the headset 181 is receiving data.

Figure 24:
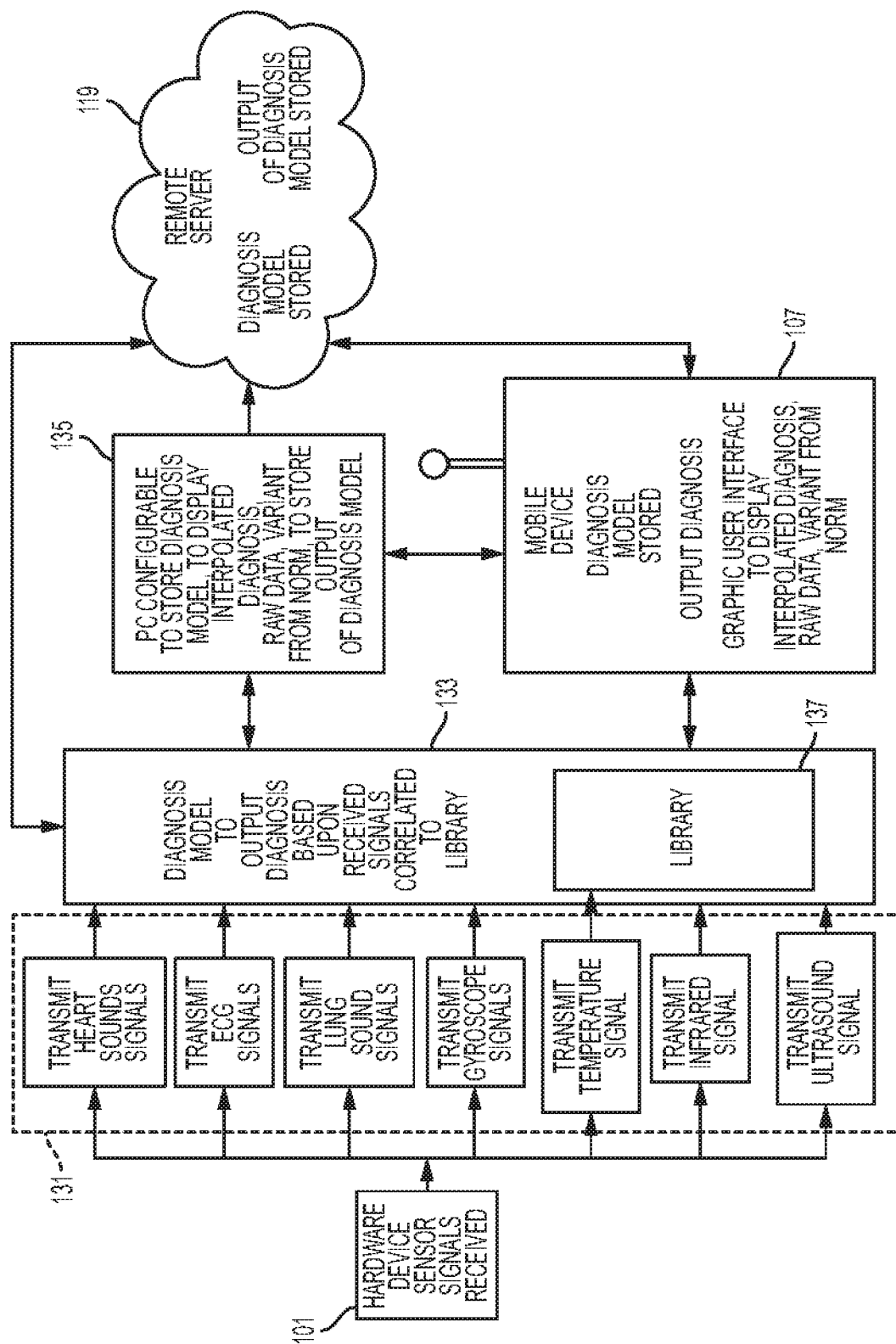
FIG. 24 is schematic view of one embodiment of a system including a stethoscope, a mobile device, and a remote server.

FIG. 24 illustrates an embodiment of processing data collected from a hardware device. Using the first hardware device 101 and the system of FIG. 23 by way of example, the hardware device 101 can be configured to sense body and other signals, collect raw data and transmit representative raw data signals 131 to a diagnosis model 133 stored in any number of possible locations. The raw data signals 131 can include any one or more of heart sound signals (e.g., sounds gathered by an audio sensor of the device 101), ECG signals (e.g., ECG data gathered by ECG sensors of the device 101), lung sound signals (e.g., sounds gathered by an audio sensor of the device 101), gyroscope signals (e.g., directional data indicative of a directional position of the device 101 gathered by an accelerometer or other directional sensor of the device 101), temperature signals (e.g., a temperature sensed by a temperature sensor of the device 101), infrared signals (e.g., infrared data gathered by an infrared sensor of the device 101), and ultrasound signals (e.g., ultrasound data gathered by an ultrasound sensor of the device 101). For example, the diagnosis model 133 can be store on the first mobile device 107, an electronic device in the form of a personal computer (PC) 135, or at the remote server 119. Where the diagnosis takes place can be dependent upon the resources available. The diagnosis model 133 can include access to a data library 137 where disease data indicative of symptoms of diseases can be stored. The diagnosis model 133 can be configured to correlate the representative raw data signals 131 of an anomaly with the disease data.

The diagnosis model 131 can include known algorithms, and can include algorithms developed specifically for the purpose of processing the collected information from the first hardware device 101. As data is collected with respect to, for example, location which may be determined based on GPS signals routinely available in a mobile device such as the first mobile device 107, models for study of effects of, for example, location can be established. Comparative modeling can be performed by the diagnosis model 131 based on data of ambient conditions such as humidity, temperature, and barometric pressure. Altitude may be recorded. Any type of data collection can be performed to assist in understanding heart conditions and/or respiratory conditions. New discoveries on types and causes of heart and other conditions are therefore possible based upon the types of data that can be collected and the analytics used to process the data. Furthermore, other attributes such as age, race, weight, height, gender, and the like, as well as any changes to that data, may provide further opportunity to model output based on the collected data by the first hardware device 101 that may be supplemented with additional data collected at the same time, or at a different time.

For example, an algorithm of the diagnosis model 133 can be configured to use wavelet transformations as a method of pattern detection, which is a very efficient method in medical signal processing. Such has also been applied to speech signal and performed reasonably well in speech and speaker recognition. For gathered heart-related data, the incoming heart beat can be stripped down to basic waveforms, and each waveform can be given a unique identifier. The timing and amplitude as well as the spatial position in the context of the entire sample can be included in the information relating to the unique waveform identifier. Each subject's heart beat can be given a code (e.g., a string of numbers, etc.) composed of a collection of SI S2 markers and an additional S3 S4 or S5 sounds. Other anomalies can be given S6 S7 S8 S9 and so on. Amplitude can be given a reference range A1-A10. Timing can be given a reference T in + and −. In an at least some embodiments, three axes of timing can be provided. Clock Sync information in relation to the vibration force can be included.

The library 137 can contain, heart, lung, abdominal, and other body sounds having had the same algorithm of the diagnosis model 133 applied to the sample sounds. All major and minor heart sounds relating to medical conditions as well as lung and abdominal sounds can be assigned this S and A code along with minimum and maximum timing between intervals. The identifiers can then best matched up with the incoming audio signal (gathered by the first hardware device 101) and the patterns in the library 137 to produce a match based on the subject's profile (e.g., age, eight, height, sex, previous medical history, medication and family history of disease) to help provide clinically accurate diagnostic advice. As mentioned above, a display device of, for example, the first mobile device 107 or the PC 135, can be configured to provide an interpolation in a graphic form of the representative raw data signals indicating characteristics determined from the representative raw data signals including, for heart-related data, color coded indicia of systole and a diastole events and an anomaly event on a time line representative of timing of the systole, diastole, and anomaly events as a result of the output of the diagnostic model 133.

Figure 25:
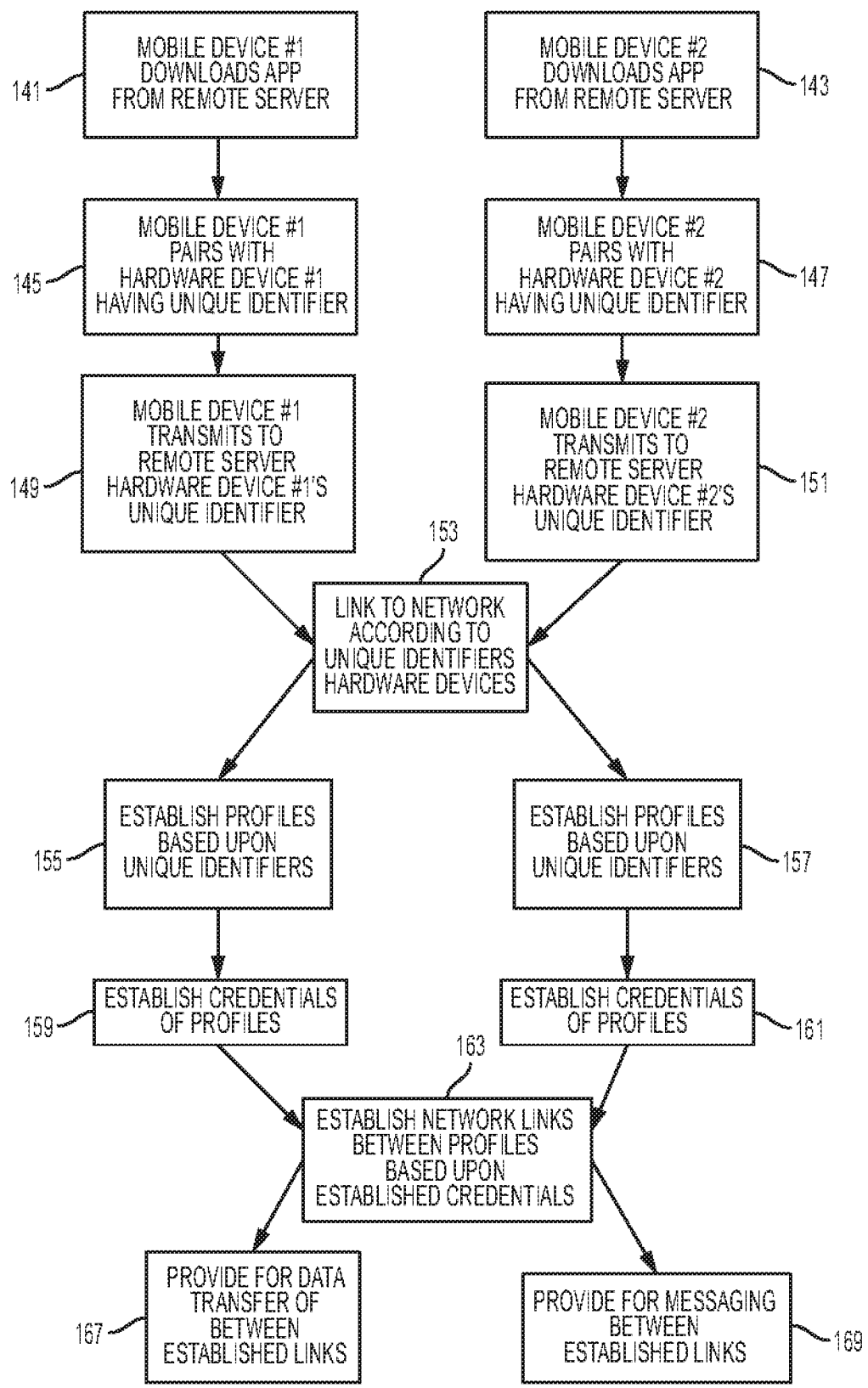
FIG. 25 is a flowchart of one embodiment of a method of linking at least two stethoscopes.
Figure 26:
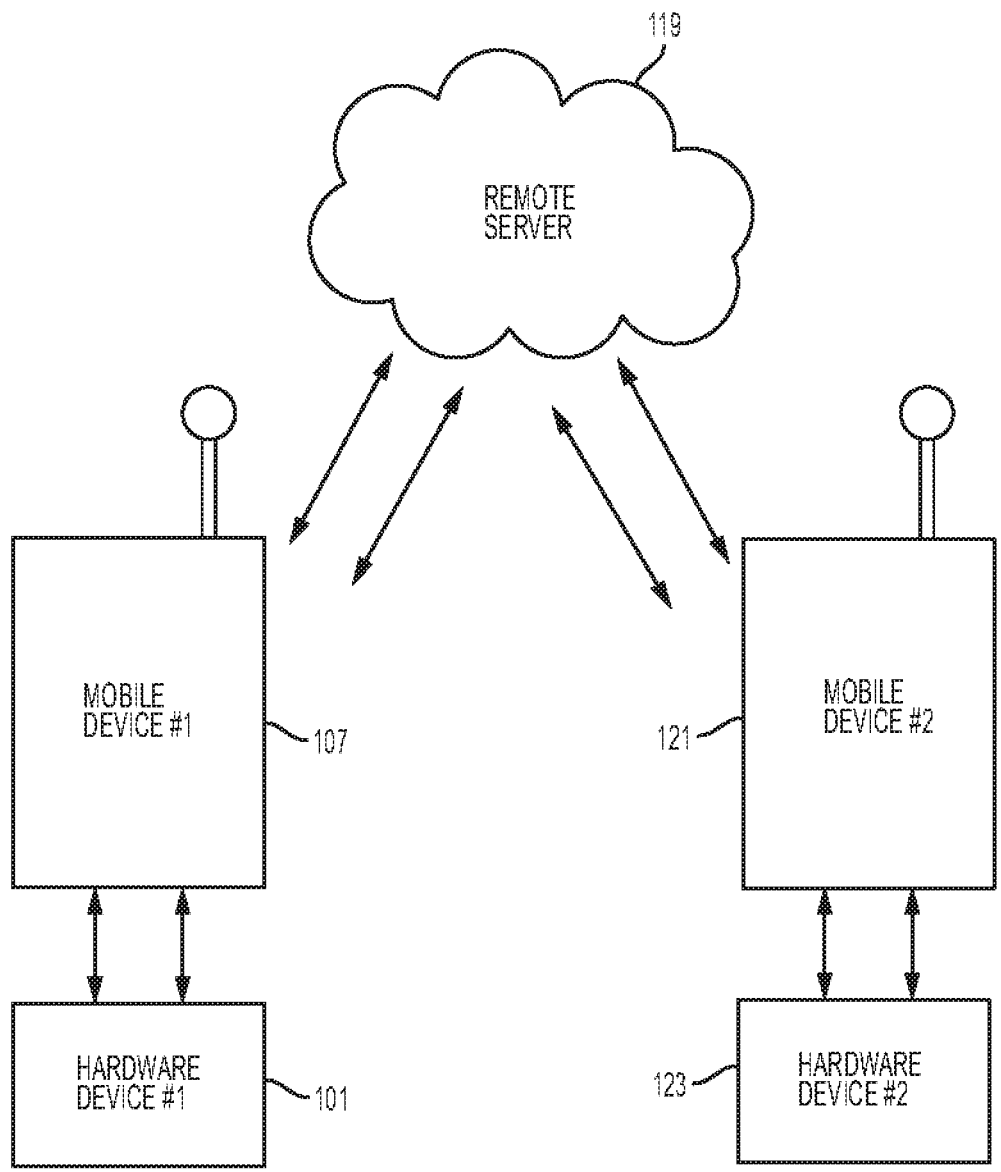
FIG. 26 is an excerpt of the system of FIG. 23.

FIG. 25 illustrates an embodiment of a method of an establishment of at least two hardware devices forming a network in which data and communication can be provided therebetween. The method of FIG. 25 is described with reference to elements of FIG. 23, an excerpt of which is shown in FIG. 26 for clarity of discussion, but any of the stethoscopes and electronic devices discussed herein can similarly function. The first mobile device 107 can download 141 an APP from the remote server 119 (e.g., in response to first user instruction), and the second mobile device 121 can download 143 the APP from the remote server 119 (e.g., in response to second user instruction). The first hardware device 101 can provide an opportunity to establish a network with the first hardware device 101 linked to the first mobile device 107 that is in communication with the remote server 119. Similarly, the fourth hardware device 123 can provide an opportunity to establish the network with the fourth hardware device 123 linked to the second mobile device 121 that is in communication with the remote server 119.

The first and fourth mobile devices 101, 123 can, via the APP downloaded thereto and installed thereon, pair 145, 147 with the first and fourth hardware devices 105, 123, respectively, which can each have a unique identifier transmitted 149, 151 to the remote server 119. The first fourth second hardware devices 101, 123 can each be linked 153 to the network according to their respective unique identifiers. Users of the hardware devices 101, 123 can establish 155, 157 profiles on their associated one of the devices 101, 123, and the users' credentials can be determined 159, 161. Credentials cab help establish which users are health care professionals so that a network can be established 163 between health care professionals. Depending upon the links established between users, data can be transferred 167 and other forms of communication such as messaging can occur 169.

Figure 27:
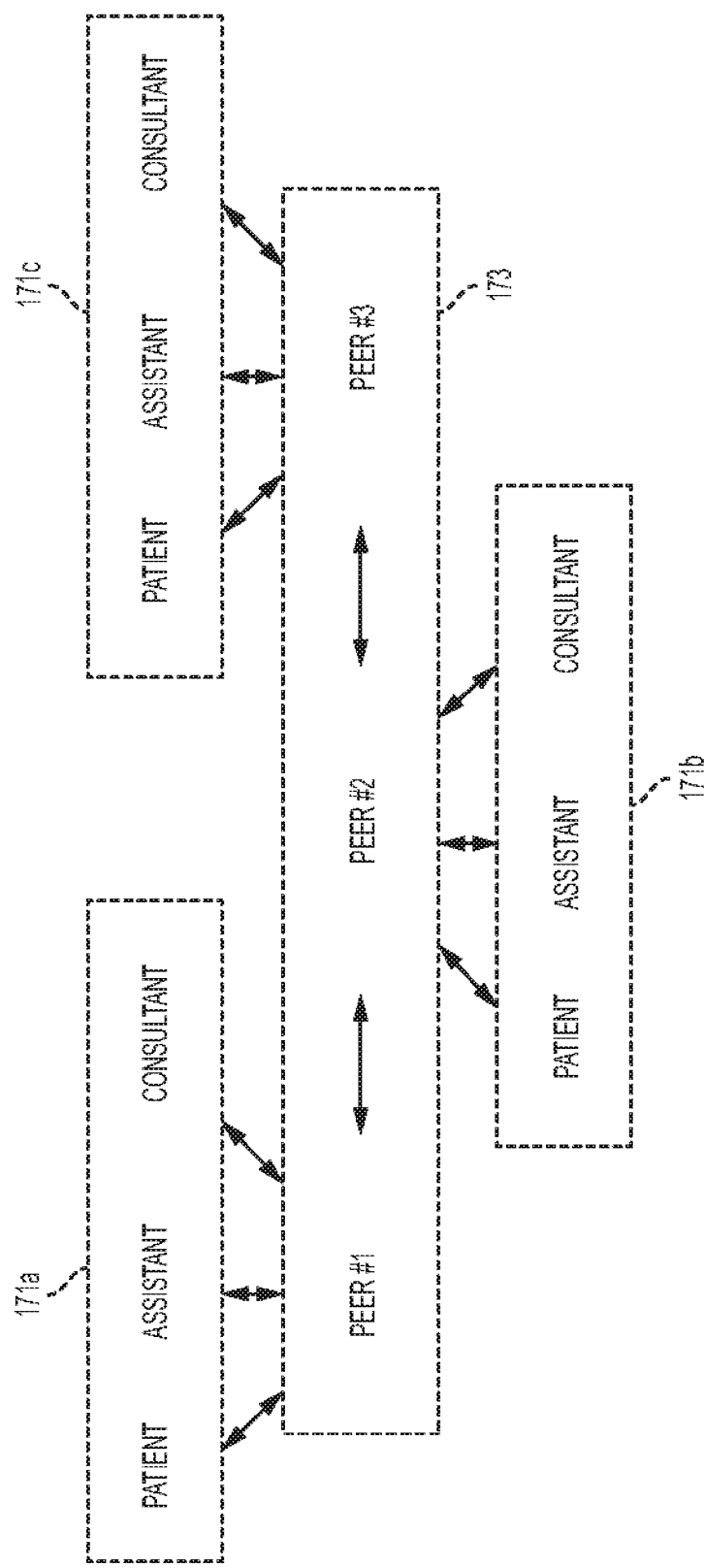
FIG. 27 is a schematic view of types of types of communication links that can be established between users of stethoscopes.

FIG. 27 shows types of communication links that can be established between users of the stethoscopes described herein once the stethoscopes are established in a network. As mentioned above, credentials as part of a profile can be determined. In this illustrated example, users such as patients, assistants, and consultants 171*a*, 171*b*, 171*c* may not be provided direct access to one another, as in this illustrated embodiment. However, peers (Peer #1, Peer #2 and Peer #3) 173 can be configured to provide access to the network. The peers 173 can, for example, be doctors. Doctors may further be administered by the clinics or hospitals for which they work. The network can be configured to provide data transfer and communication via, for example, messaging, voice, and video between peers 173 at one level, and between other users 171*a*, 171*b*, 171*c* at another level.

Figure 28:
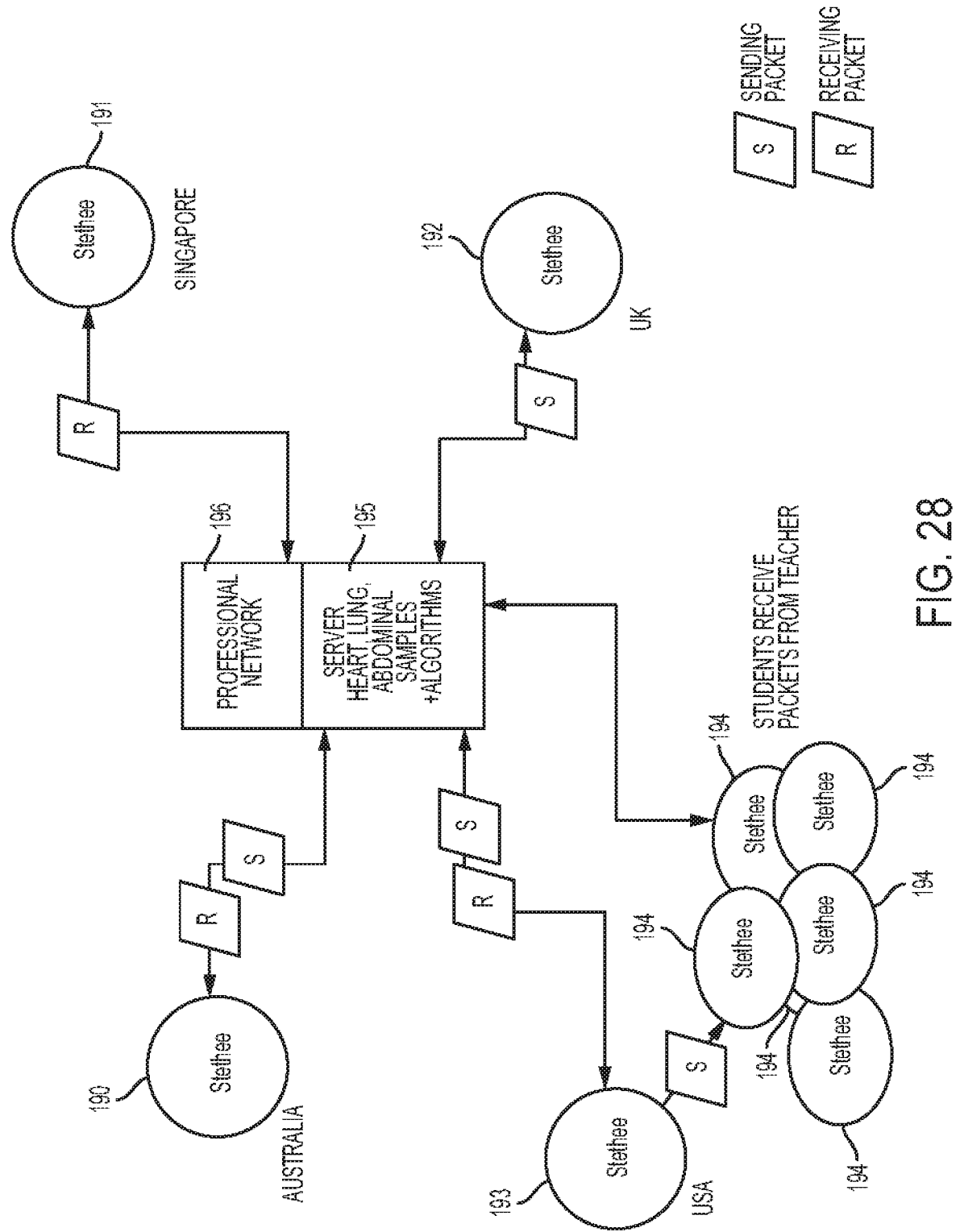
FIG. 28 is a schematic view of one embodiment of a system including a plurality of stethoscopes and a remote server.

FIG. 28 illustrates another embodiment of pairing (linking) arrangements and network configuration of a stethoscope (e.g., any of the stethoscopes described herein) and an electronic device external to the stethoscope. Stethoscopes are referred to "Stethee" 190, 191, 192, 193, 194 in FIG. 28. An external electronic device in FIG. 28 includes a remote server 195. As shown, the stethoscopes 190, 191, 192, 193, 194 can be located in multiple different countries and can be configured to share information with one another via the server 195. Thus, data (referred to as "packets" in FIG. 28) can be shared between remote locations, which may facilitate collaboration and community in a professional network 196, and/or may facilitate learning by allowing one of the stethoscopes 190, 191, 192, 193, 194 to be used on a subject while any one or more of the other stethoscopes 190, 191, 192, 193, 194 can output the same audio, vibration, and/or light as the stethoscope being used on the subject. The countries in FIG. 28 are examples only.

As mentioned above, data related to bodily characteristics can be displayed in a variety of ways. The data can be displayed via a GUI or screen on an electronic device. The screen can show a variety of different types of information, and the information can be displayed in any of a variety of ways.

FIGS. 29-80 and 82-84 illustrate embodiments of screens including data related to use of a stethoscope that can each be configured to be provided by a system. The information shown on these screens are examples only, and any of the screens can include more information or less information. The screens discussed below with respect to FIGS. 29-80 and 82-84 are touchscreens, but similar screens can be provided on other types of displays.

Figure 29:
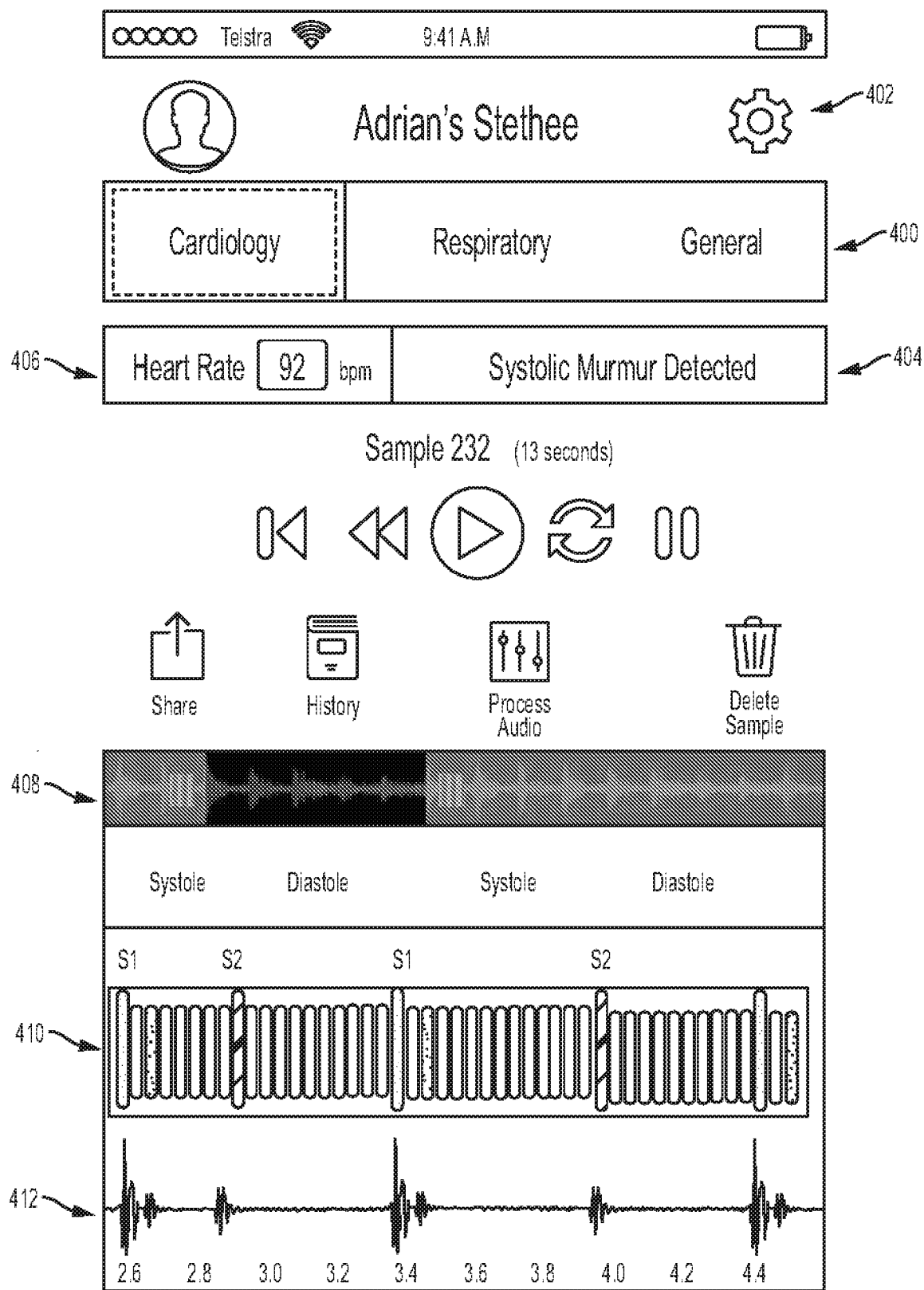
FIG. 29 is a diagram showing one embodiment of a cardiology information screen.
Figure 30:
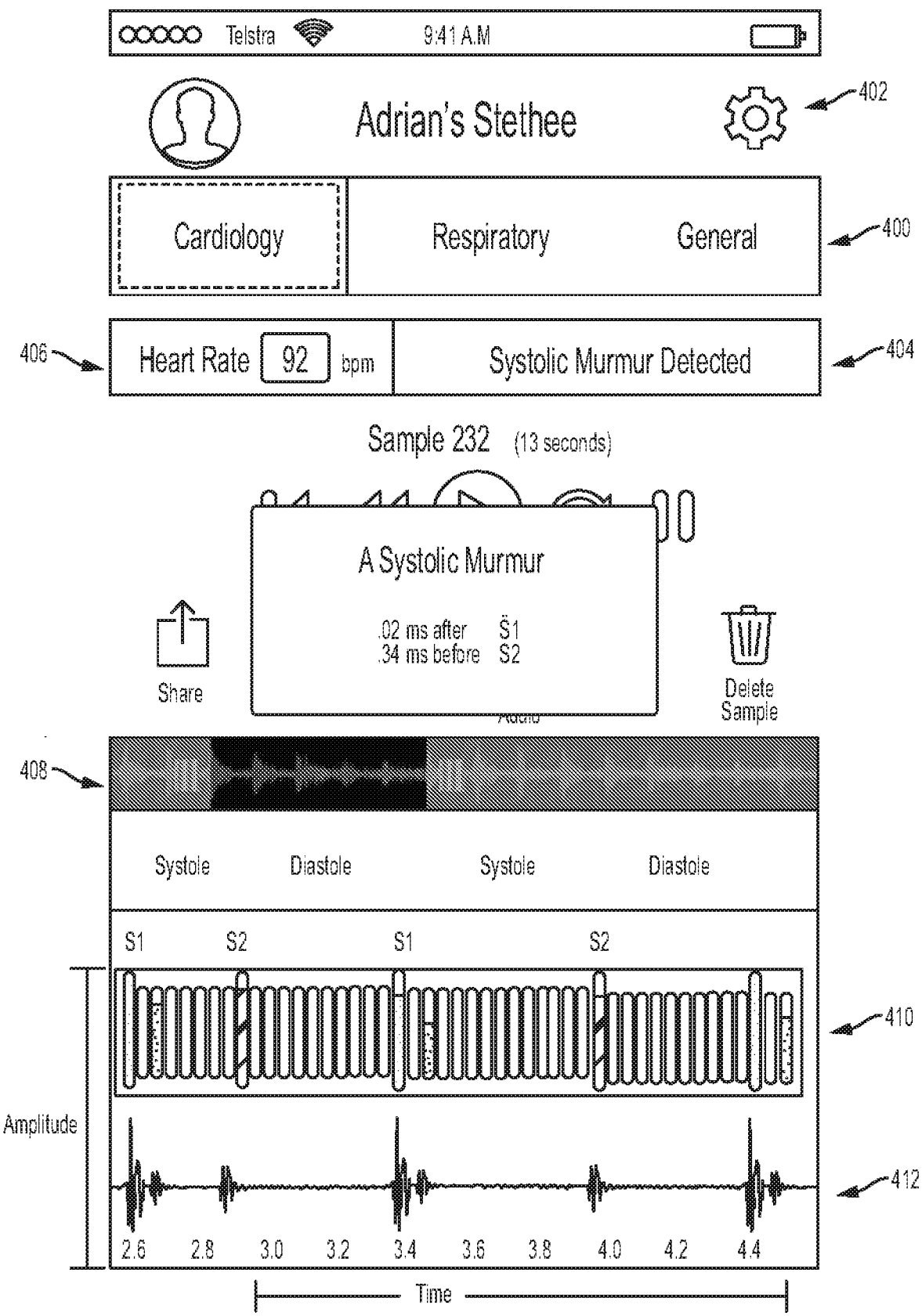
FIG. 30 is a diagram showing another embodiment of a cardiology information screen.
Figure 31:
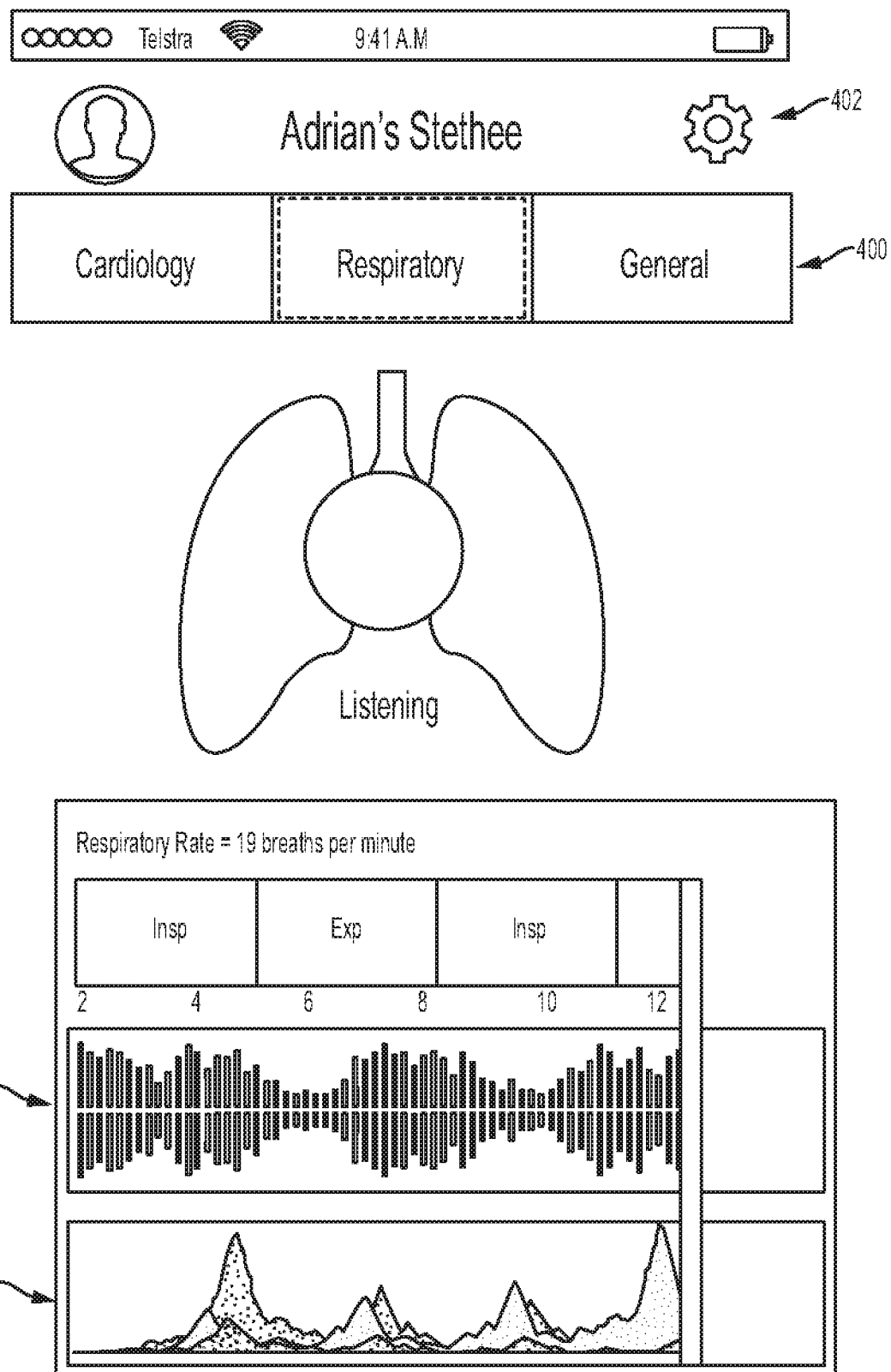
FIG. 31 is a diagram showing one embodiment of a respiratory information screen.

FIGS. 29-31 illustrate embodiments of screens displaying information related to data gathered by a stethoscope (identified as "Adrian's Stethee" in FIGS. 29-31). Raw data can be collected by the stethoscope, processed by the diagnostic model, and provided on the screen as a user friendly GUI to show representative raw data. The screens can each include a menu 400 that allows a user to select cardiology data (e.g., heart data), respiratory data (e.g., lung data), or general data (e.g., abdominal data that is specific to either the heart or the lung). The one of the menu items selected can determine which algorithms are used to analyze the gathered data to help ensure that accurate information is gathered, is displayed on the screen, and is properly vetted for possible anomalies.

The screens of FIGS. 29-31 can each include a configuration icon 402 that allows a user to view and/or adjust settings such as stethoscope settings information (e.g., colors, sounds, etc.) and information regarding the subject on which the stethoscope is being used.

FIGS. 29 and 30 have "cardiology" selected and display heart information. The screens can include an indication 404 of a detected possible anomaly, which includes a systolic murmur in this illustrated example. FIG. 30 also shows details regarding the detected possible anomaly, namely that it is occurring 0.02 ms after SI and 0.34 ms before S2. The screens can show a current heart rate 406. The screens can include a timeline 408 that allows the user to select an amount of sample data to analyze by shortening or lengthening the currently highlighted period of time in the timeline 408. Portions of the timeline 408 can be identified as "Systole" or "Diastole" to facilitate the user's quick identification of which phase of the heartbeat cycle any detected possible anomalies exist. In this illustrated embodiment, this identification is in a bar below the timeline 408 and above a grid 410.

The screens can include the grid 410 that identifies and represents SI and S2 heart sounds in different colors from one another (e.g., SI in blue and S2 in green) to facilitate easy identification of the heart sounds. The grid 410 can also identify and represent any possible anomalies such as extra or abnormal heart sounds. The possible anomalies can be on the grid 410 in a different color (e.g., red) than the SI and S2 heart sounds to facilitate their easy identification. The grid 410 in this illustrated embodiment is split into ten bars between S1 and S2, with each of the bars representing location of an "extra" sound in relation to SI and S2 sounds and an amplitude of each of the "extra" sound bars sound in relation to S1 and S2 sounds (with the Y axis being amplitude and the X axis being time in seconds and milliseconds, as shown in FIG. 30). The "extra" sound represents a detected possible anomaly. Selection of the "extra" bar can cause the details regarding the detected possible anomaly to appear. A number of bars between SI and S2 in the grid 410 can be determined by the algorithm of the diagnosis model and sample data for normal heart sounds at the current heart rate. Bar sensitivity can be adjusted up to, e.g., one hundred bars between SI and S2 and between S2 and SI. In general, the grid 410 can allow the user to quickly determine and classify heart sound anomalies and diagnosis based on pattern recognition and colors of the bars.

The screens can include a waveform 412 representative of the audio incoming from the stethoscope. The timeline 408, the grid 410, and the waveform 412 can all be on the same time scale and aligned with one another to facilitate clear, consistent display and interpretation of data.

The screens can include a selectable "Share" icon that allows the user to send the gathered data to another person, such as the subject's general practitioner, to one or more of the user's medical colleagues, etc. The screens can include a selectable "History" icon that allows the user to view historical data for the subject on which the stethoscope is being used. The screens can include a selectable "Process Audio" icon that allows the user to analyze the most recently gathered sounds. The screens can include a selectable "Delete Sample" icon that allows the user to delete the most recently gathered sounds, such as if the user believes that the data was not accurately collected due to any one or more factors such as improper or irregular placement of the stethoscope on the subject's chest.

FIG. 31 has "respiratory" selected and displays breathing information. The screen can show a current respiratory rate, which in this illustrated embodiment is nineteen breaths per minute. The screen can include a grid 414 that can generally be configured similar to the grid 410 for heart sounds, and can include a waveform 416 that can generally be configured similar to the waveform 412 for heart sounds. Inspiration ("Insp") and expiration ("Exp") can be identified on the screen along the time (X) axis similar to the "Systole" or "Diastole" labels on the heart information screens.

Figure 32:
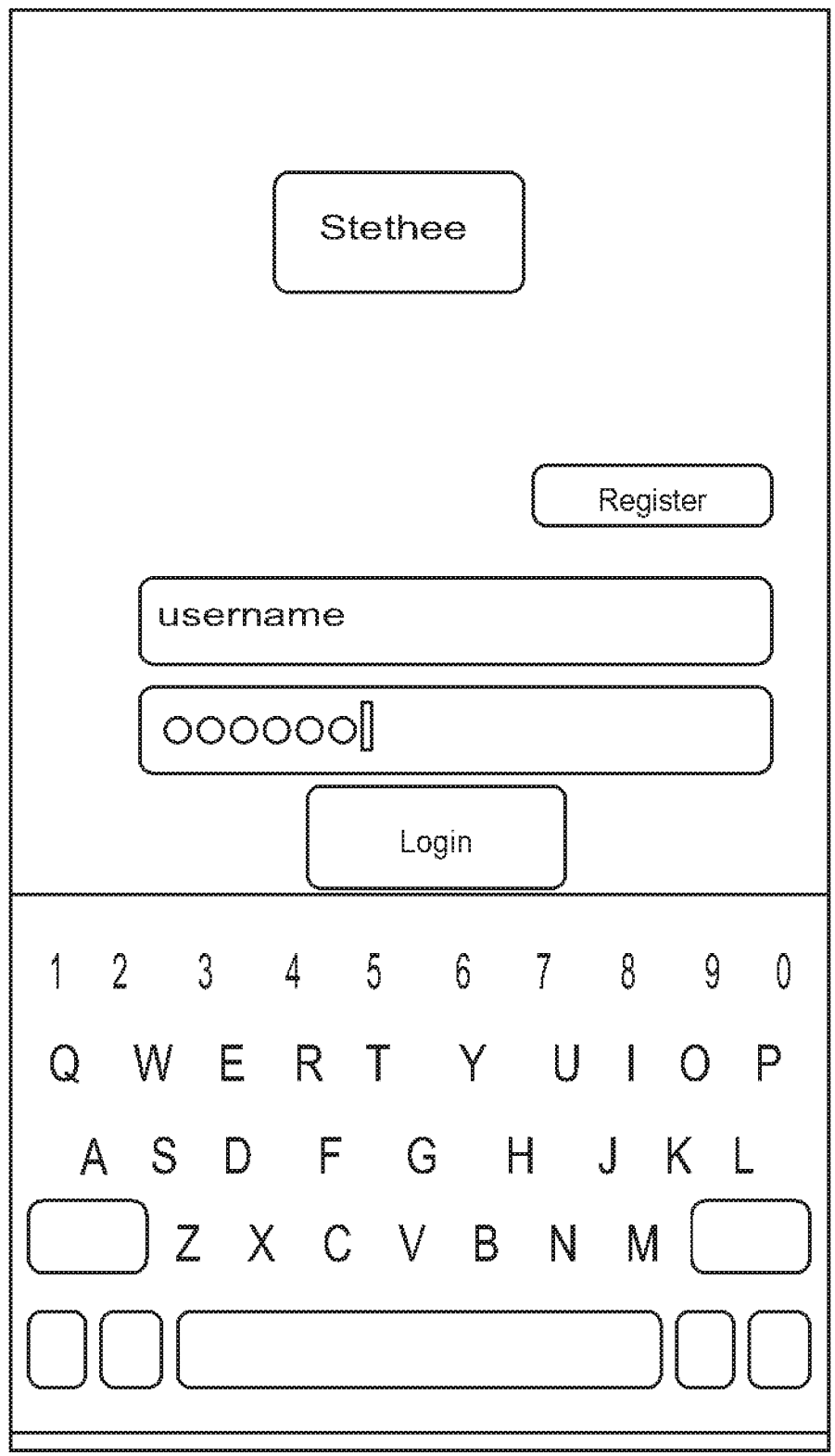
FIG. 32 is a diagram showing one embodiment of a login screen.
Figure 33:
FIG. 33 is a diagram showing one embodiment of a team screen.
Figure 34:
FIG. 34 is a diagram showing one embodiment of a team add screen.
Figure 35:
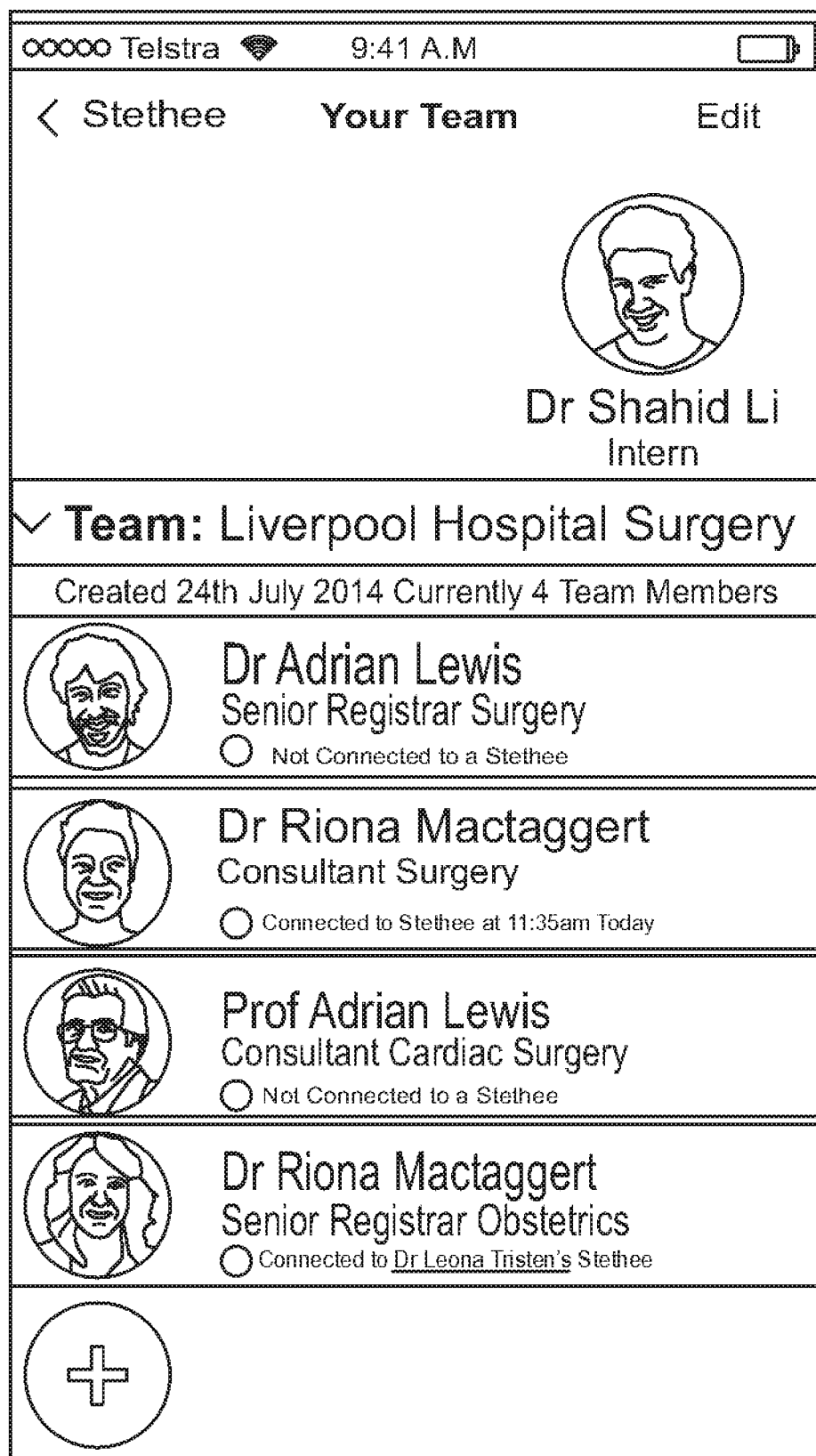
FIG. 35 is a diagram showing the team screen of FIG. 33 with team members added.

FIGS. 32-35 illustrate embodiments of screens that may facilitate team building with respect to information related to data gathered by a stethoscope. Members of a team can automatically have the information shared therebetween, which may facilitate community, accurate patient diagnoses, and/or learning. FIG. 32 shows a login screen for a user. FIG. 33 shows a team screen for the logged-in user that includes the user's identity, the team's name, and an ability to add additional team members. FIG. 34 shows a team add screen that allows team members to be added to the team and for other settings related to the team to be edited, such as team moto, team flag or logo, and team name. FIG. 35 shows the team page of FIG. 33 after team members have been added to the team via the add screen of FIG. 34.

Figure 36:
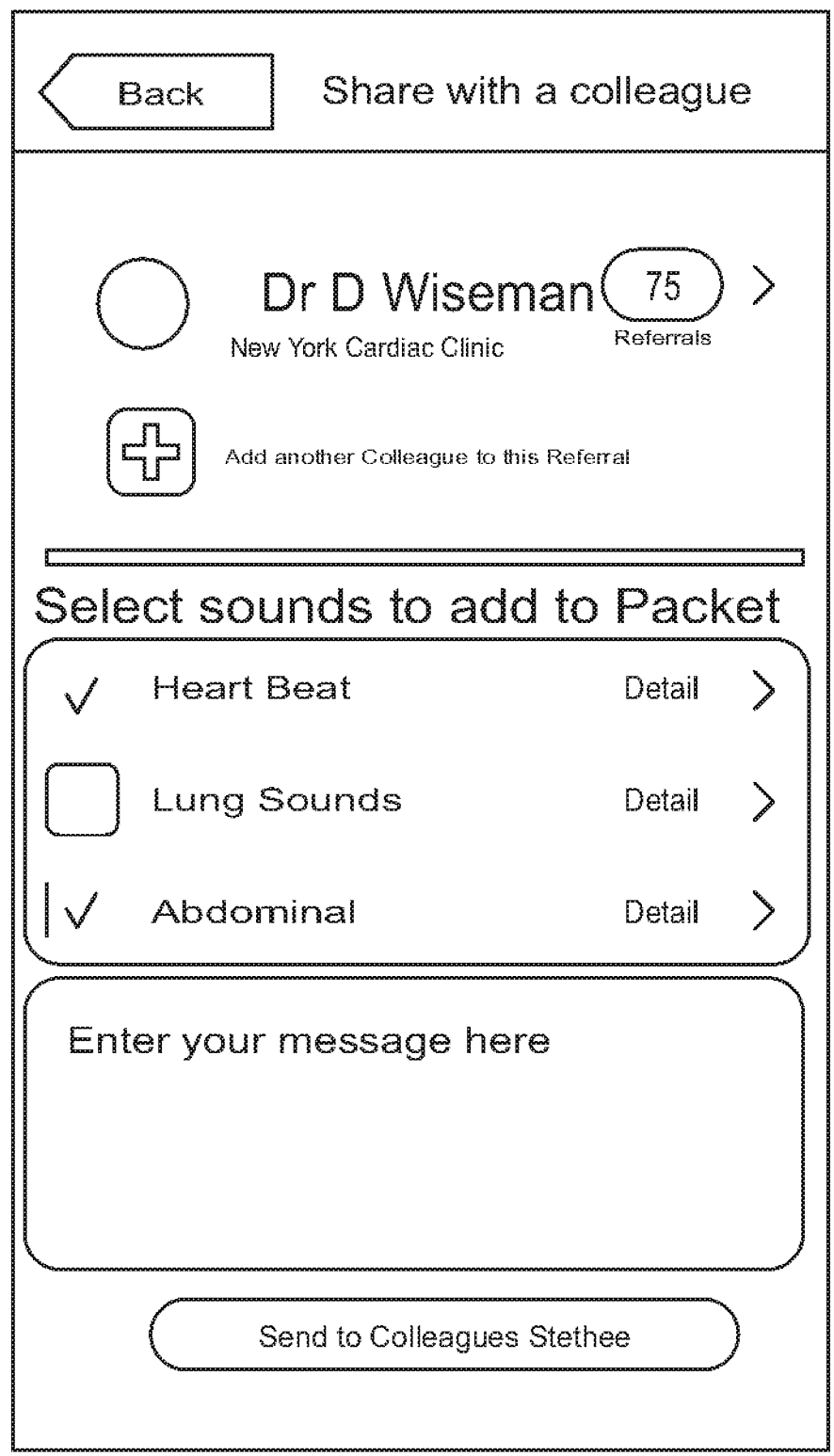
FIG. 36 is a diagram showing one embodiment of a share selection screen.
Figure 37:
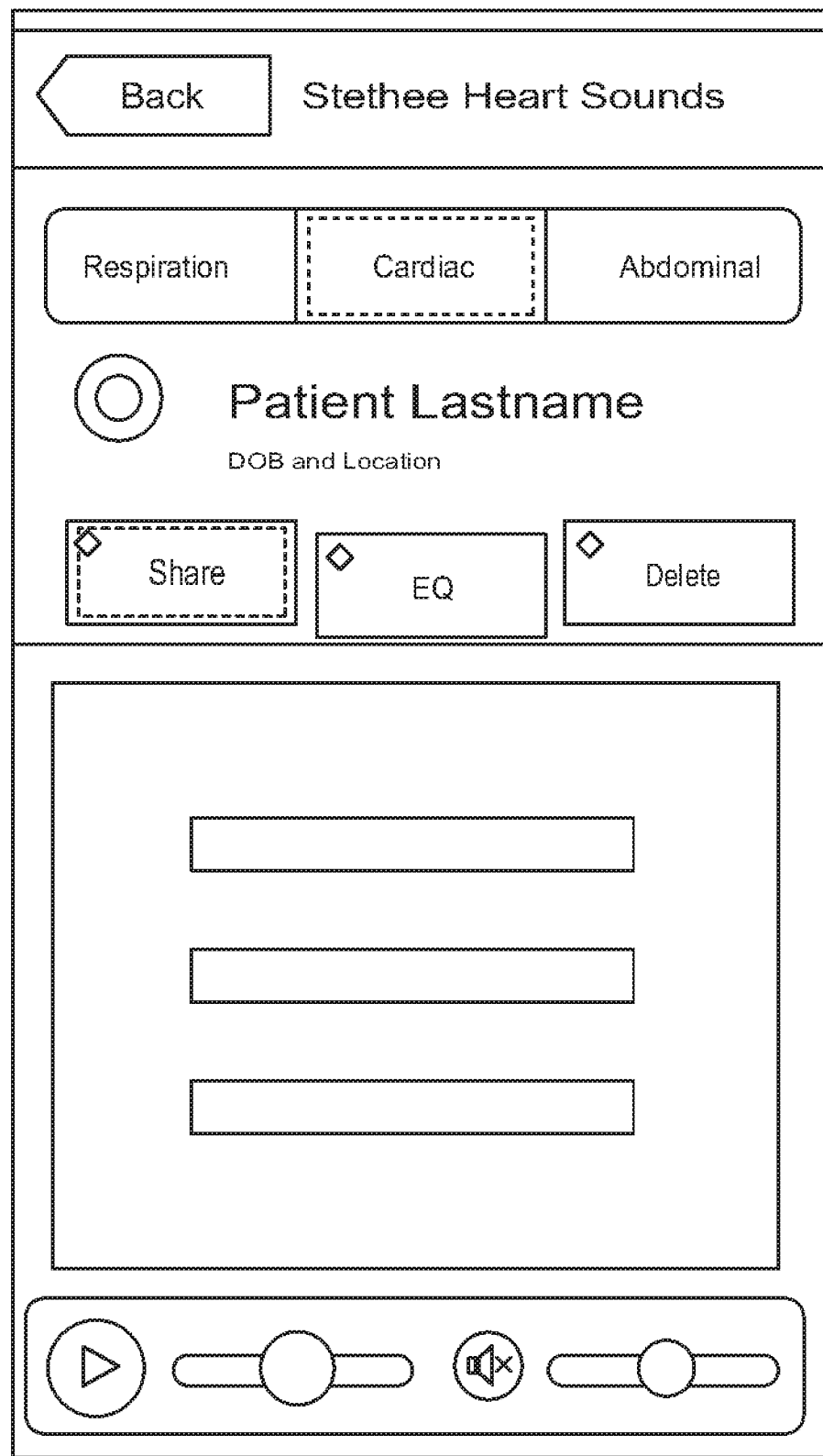
FIG. 37 is a diagram showing one embodiment of a cardiac share screen.
Figure 38:
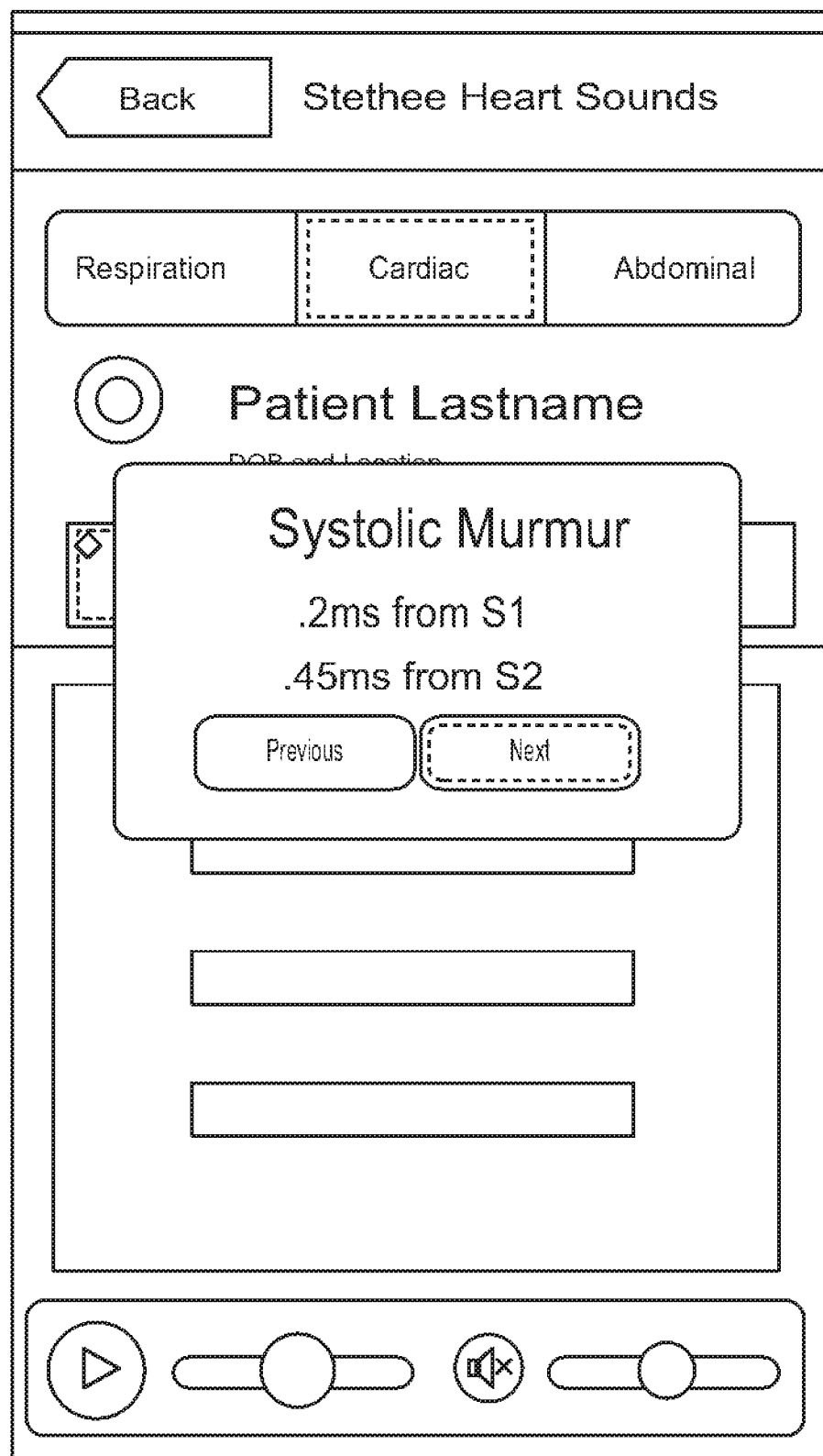
FIG. 38 is a diagram showing another embodiment of a cardiac share screen.
Figure 39:
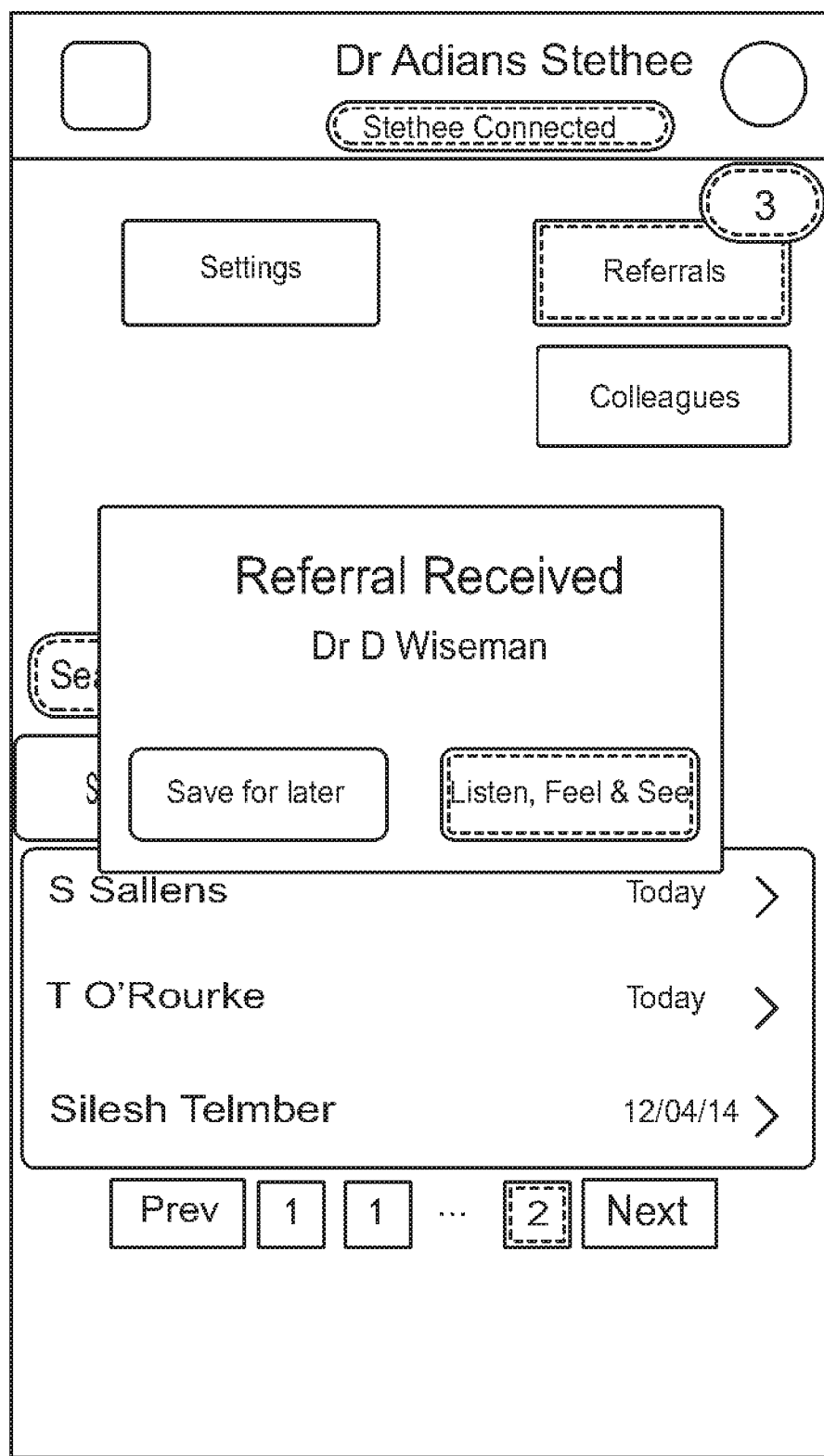
FIG. 39 is a diagram showing one embodiment of a referral received screen.
Figure 40:
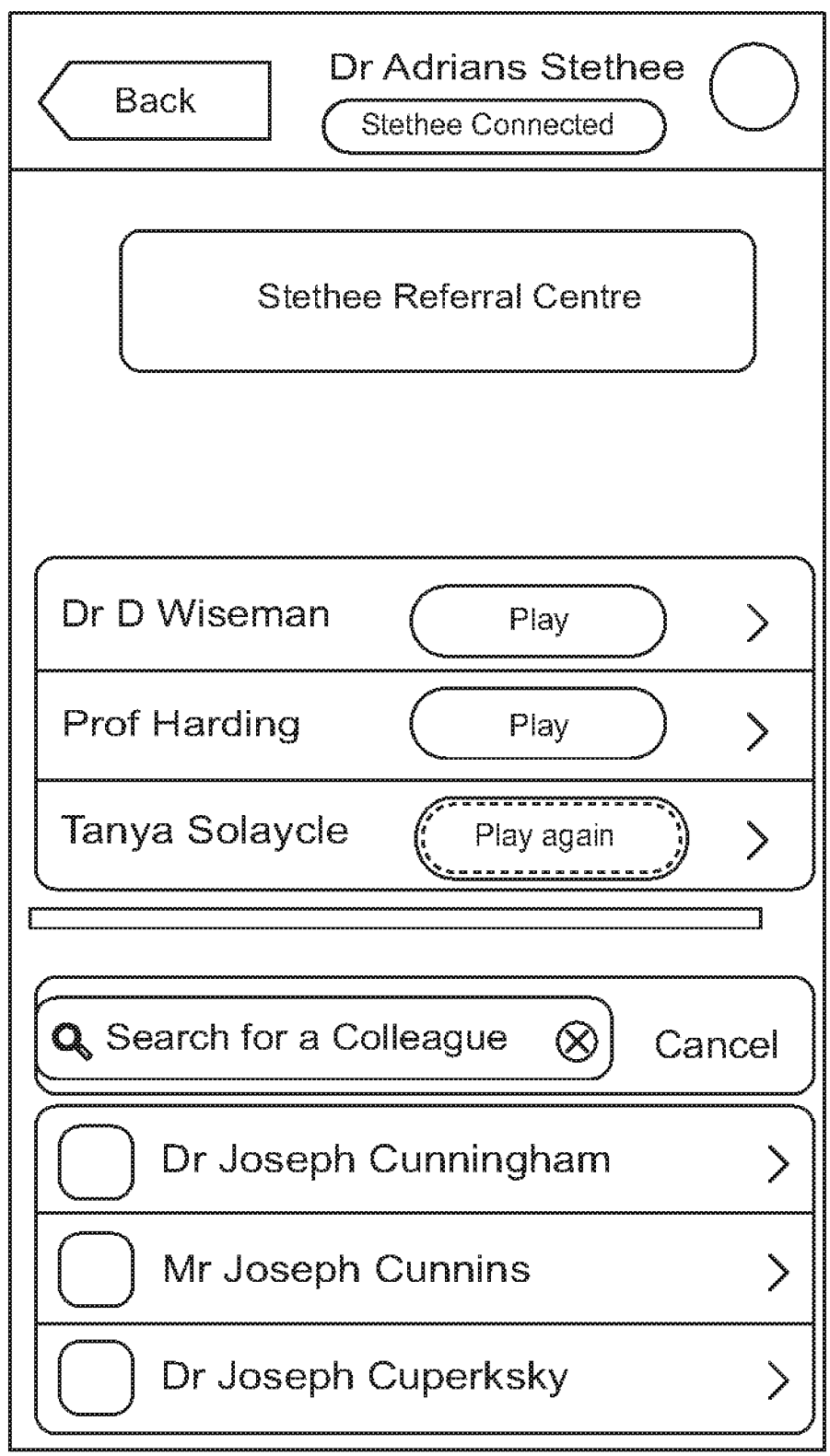
FIG. 40 is a diagram showing one embodiment of a referral centre screen.
Figure 41:
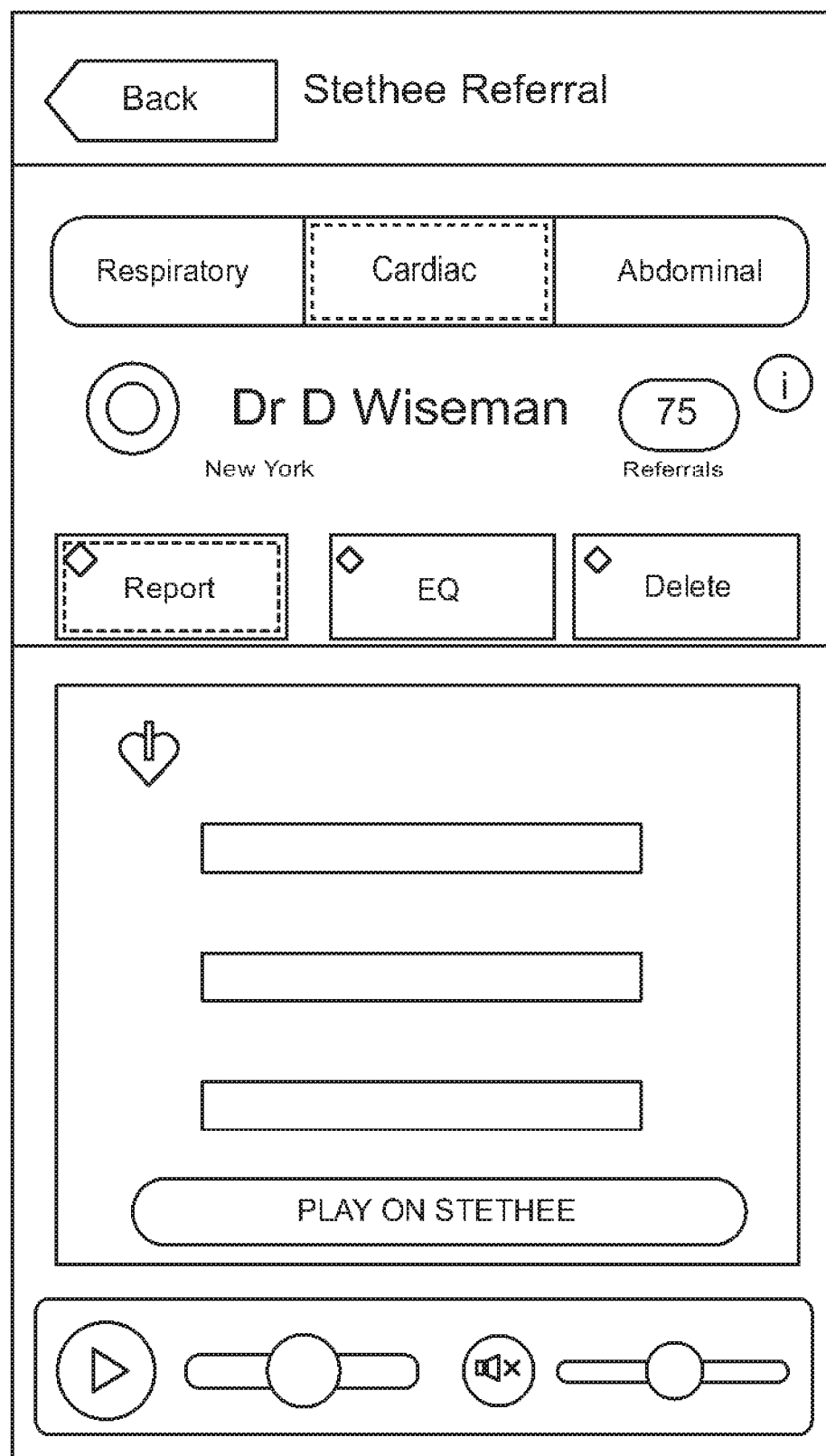
FIG. 41 is a diagram showing one embodiment of a referral information screen.
Figure 42:
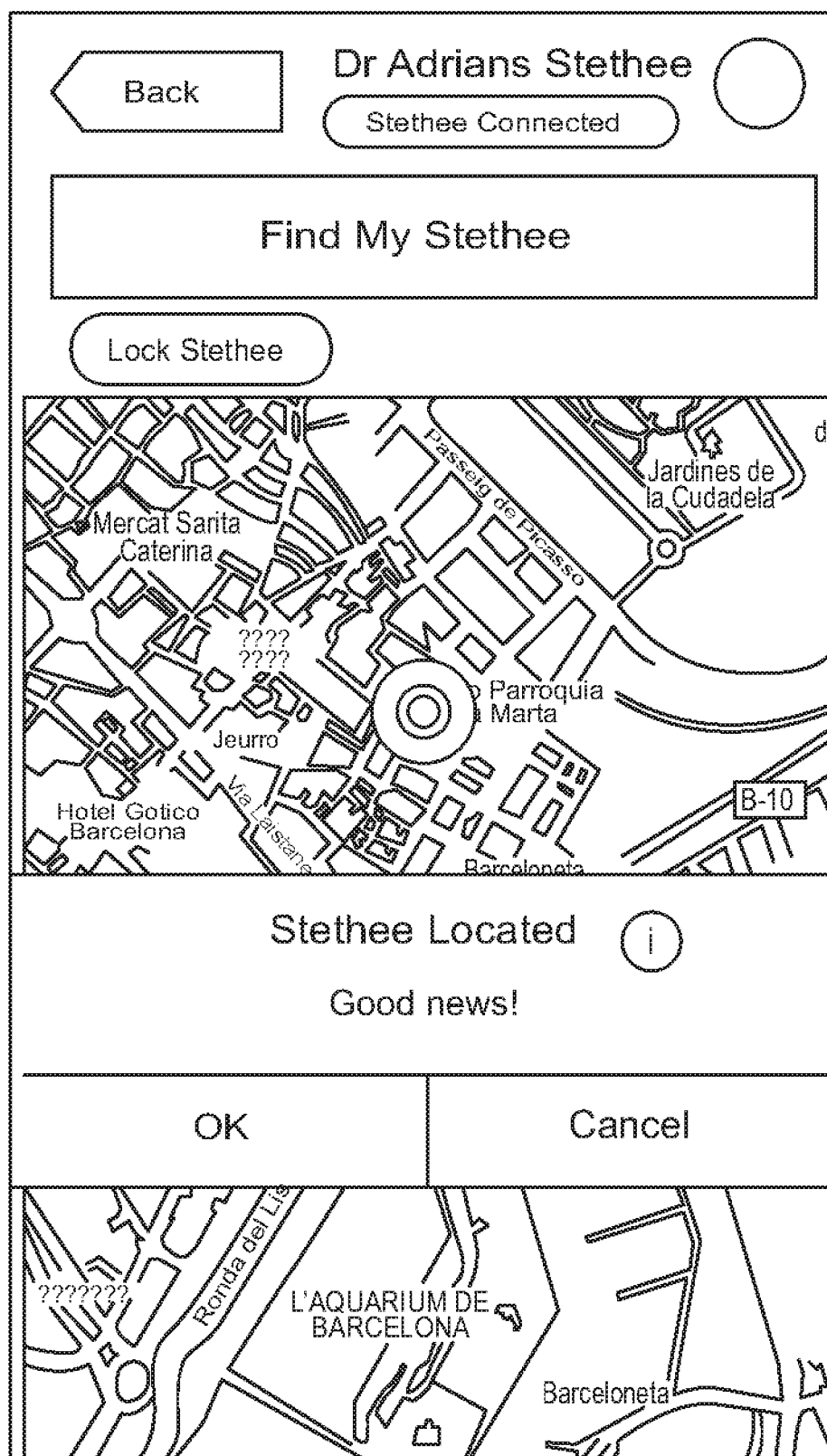
FIG. 42 is a diagram showing one embodiment of a map screen.
Figure 43:
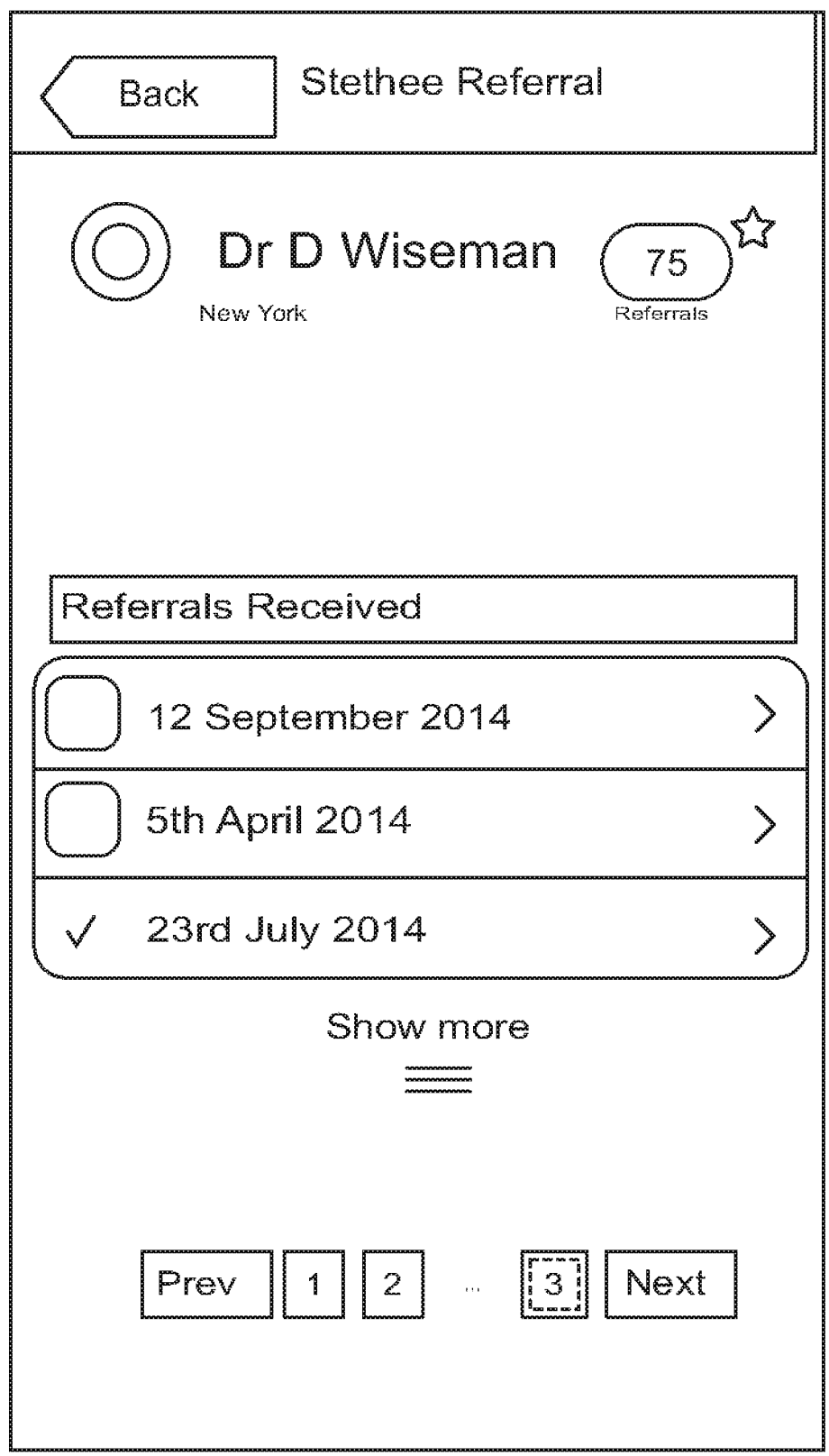
FIG. 43 is a diagram showing one embodiment of a referrals list screen.
Figure 44:
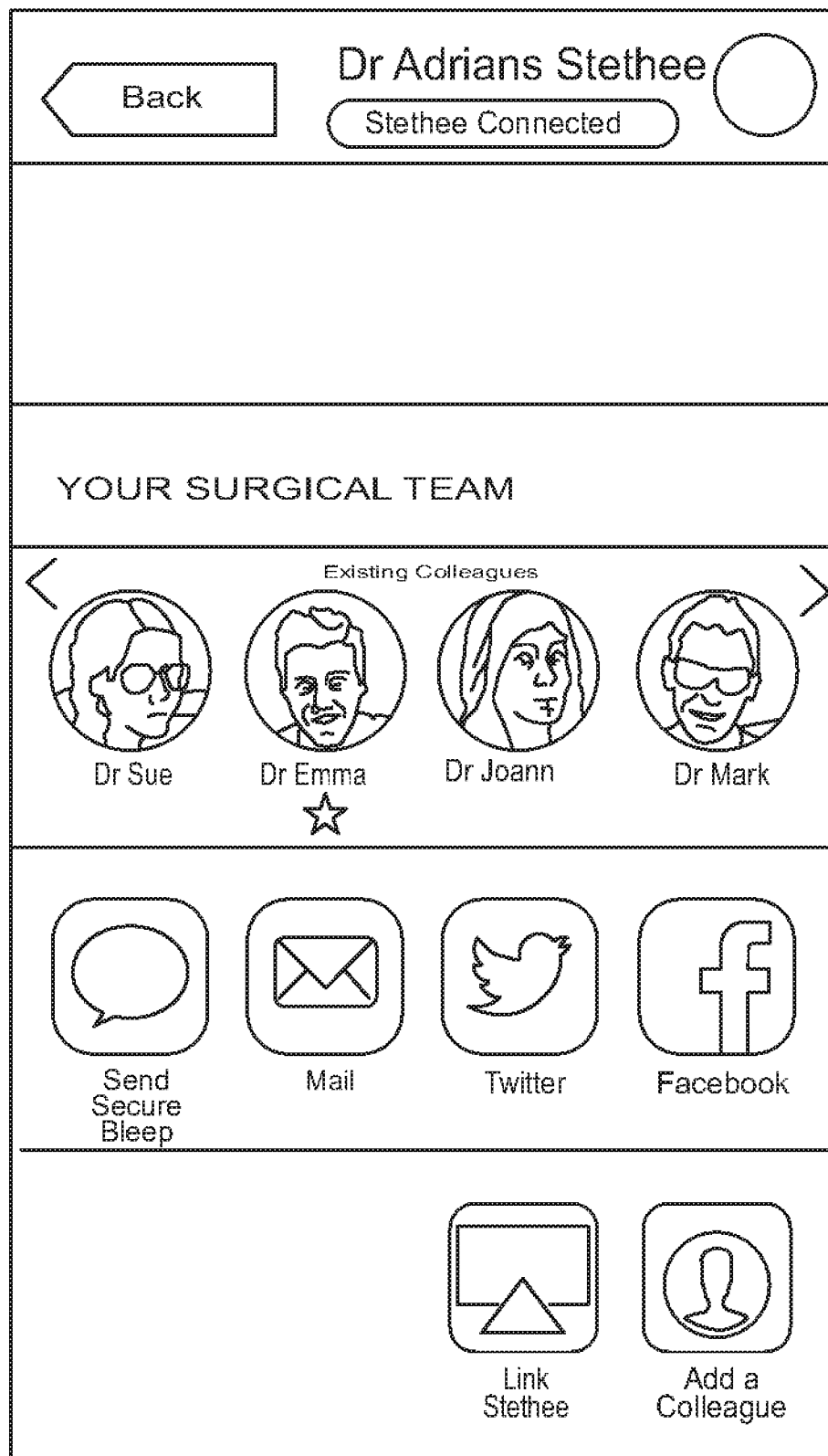
FIG. 44 is a diagram showing another embodiment of a team screen.
Figure 45:
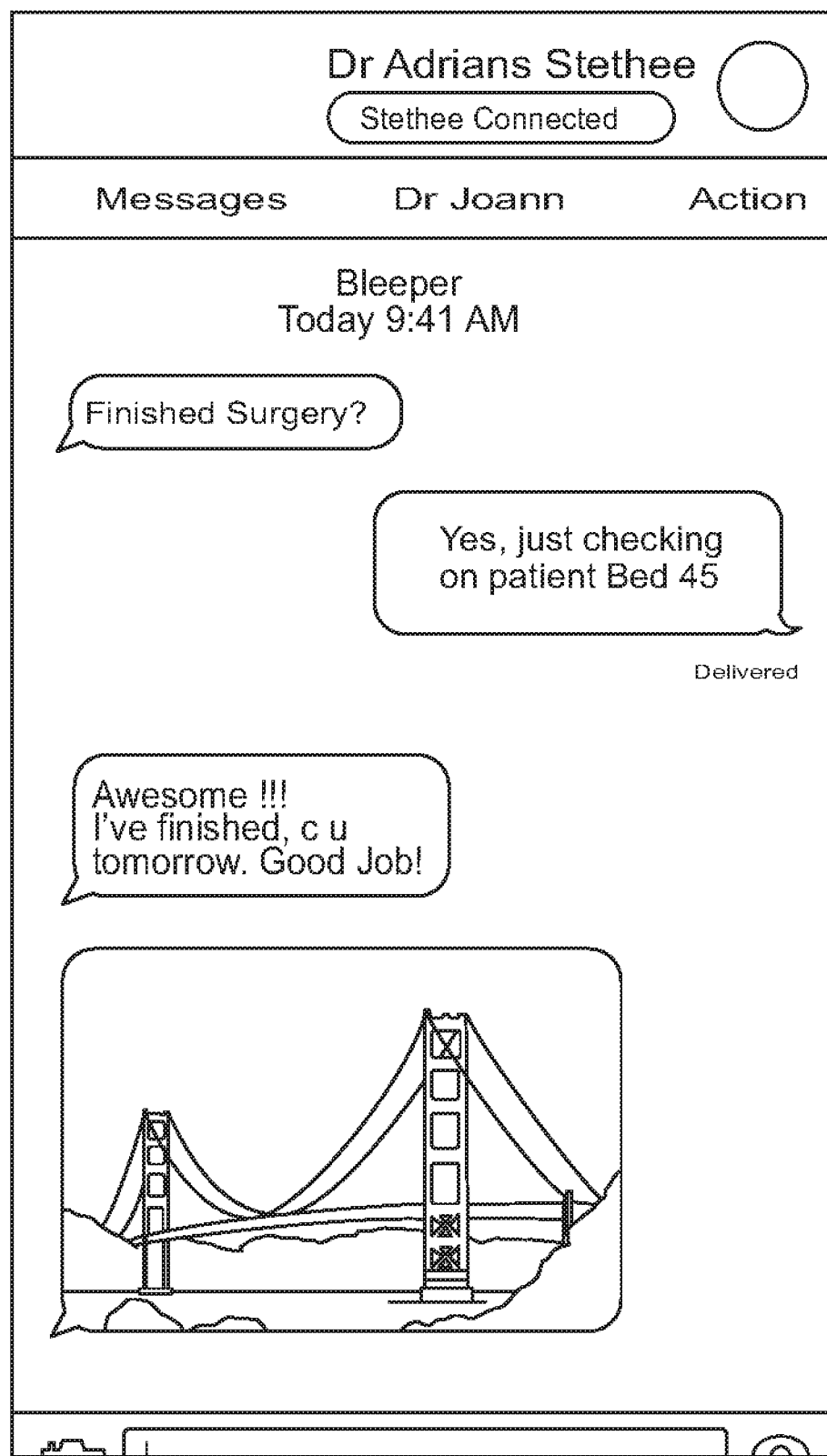
FIG. 45 is a diagram showing one embodiment of a communication screen.

FIGS. 36-45 illustrate embodiments of screens to facilitate the sharing of information related to data gathered by a stethoscope with one or more peers (e.g., among team members, with the subject on whom the stethoscope was used, with a doctor of the subject on whom the stethoscope was used, with students, etc.). FIG. 36 shows a share selection screen that allows a user of a stethoscope to share gathered data with a peer, "Dr. D. Wiseman" in this illustrated embodiment. The user can select a type of information to share (e.g., heartbeat, lung sounds, or abdominal) and can add a message to be delivered to the peer with the shared information. FIGS. 37 and 38 show cardiac share screens that allow the user to select which gathered cardiac data to share with a selected peer (or peers). FIG. 39 show a referral received screen that indicates receipt of a referral (from Dr. D. Wiseman to Dr. Adrians in this illustrated embodiment), which includes information selected to be transmitted to the selected peer, which is Dr. Adrians in this illustrated embodiment. FIG. 40 shows a referral center screen that shows received referrals and allows the user to share information with other peers. FIG. 41 shows a referred information screen that shows the information received, which in this illustrated embodiment is information that Dr. Adrians received from Dr. D. Wiseman. FIG. 42 shows a map screen that indicates a location of the user's stethoscope, which can be determined based on, for example, GPS information for the stethoscope. FIG. 43 shows a referrals list screen that indicates all referrals received from a specific peer, Dr. D. Wiseman in this illustrated embodiment. FIG. 44 shows a team screen that identifies the user's (Dr. Adrians's) team members and communication options for communication with any one or more of the team members. FIG. 45 shows a communication screen between the user and one of the team members.

Figure 46:
FIG. 46 is a diagram showing another embodiment of a login screen.

FIG. 46 illustrates another embodiment of a login screen.

Figure 47:
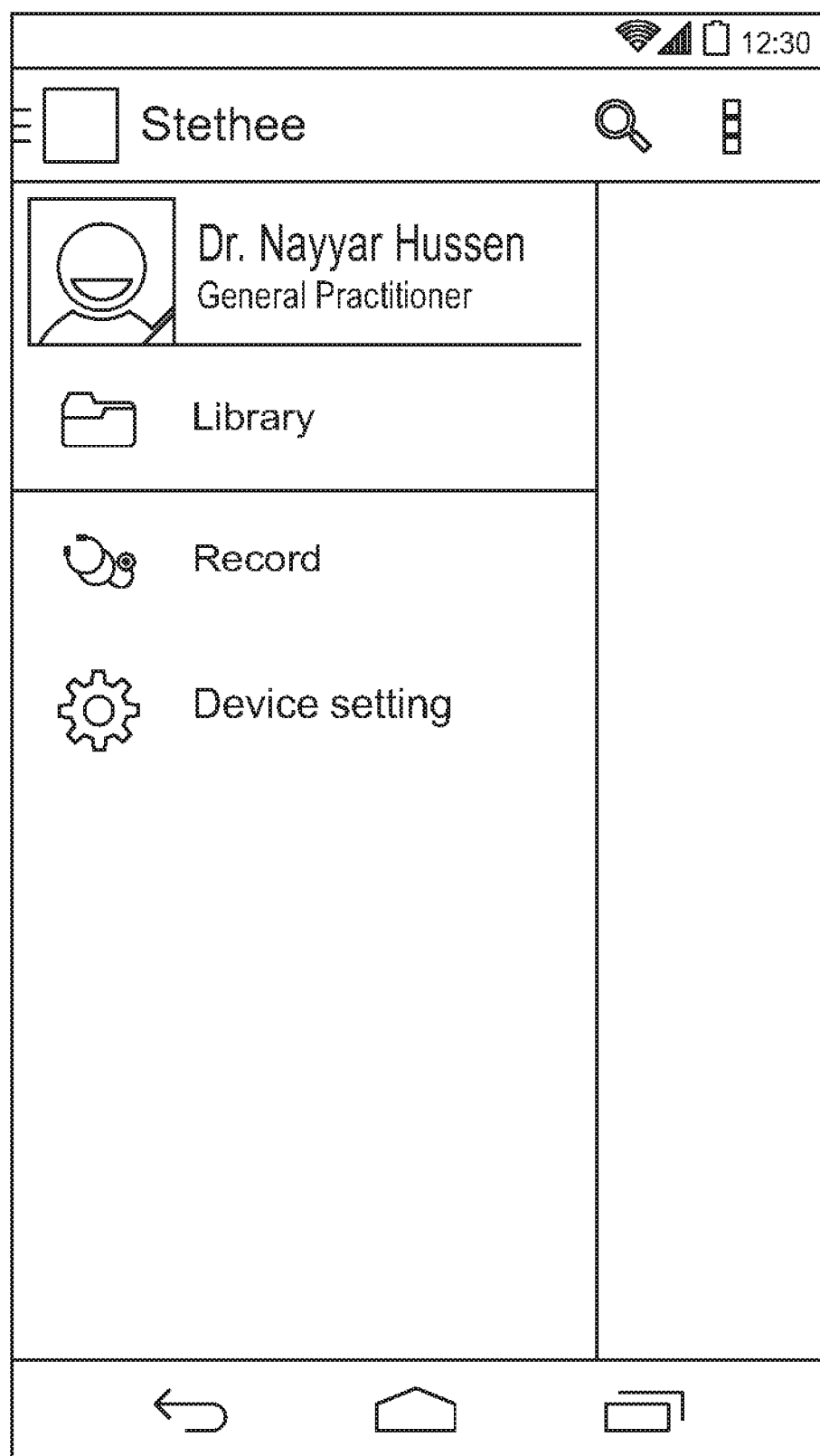
FIG. 47 is a diagram showing one embodiment of a library screen.

FIG. 47 illustrates an embodiment of a library screen that indicates a mode of library selected in the GUI. The library can be stored data of particular persons or generic data that may be used by the diagnostic model.

Figure 48:
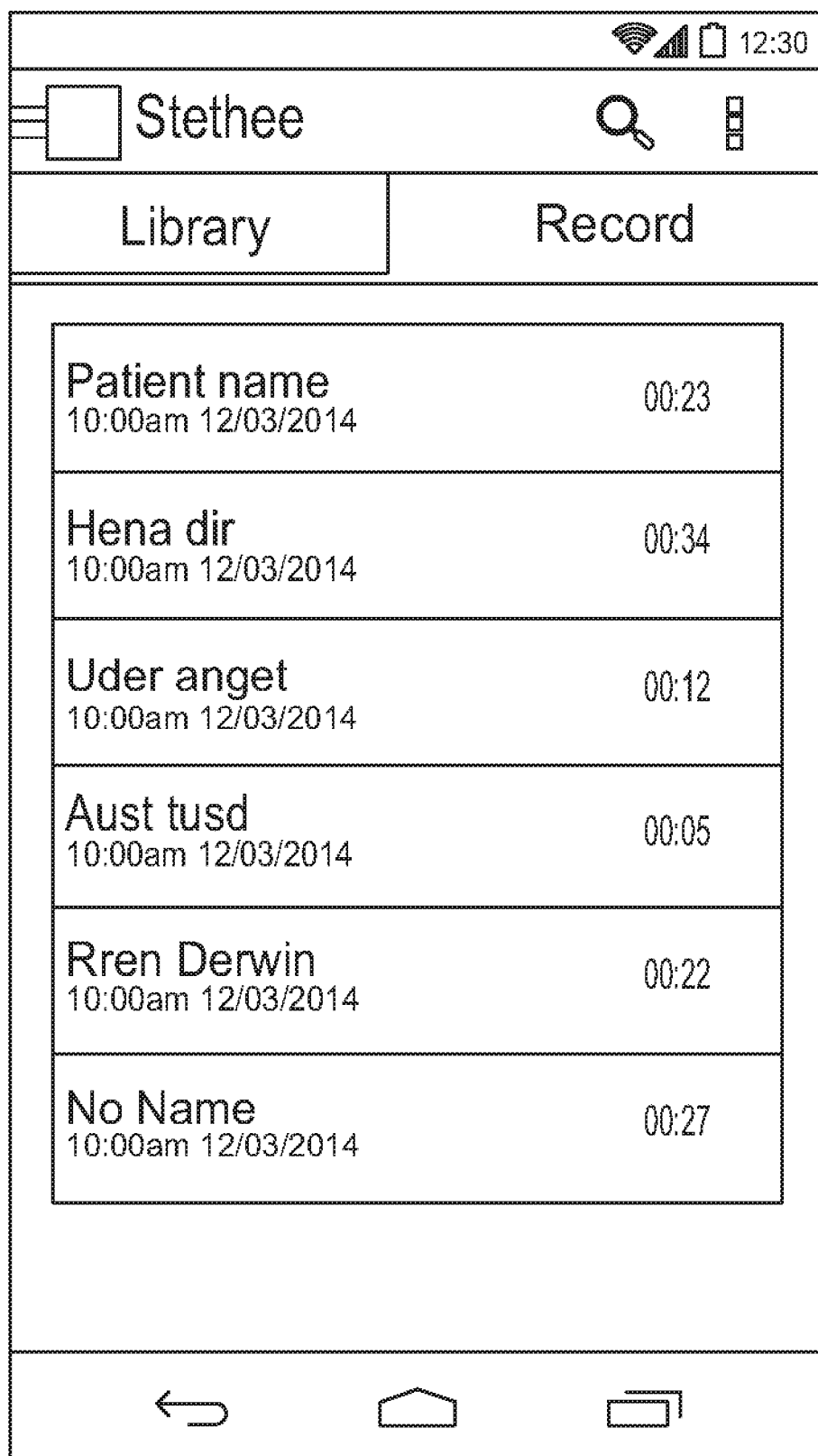
FIG. 48 is a diagram showing another embodiment of a library screen.
Figure 49:
FIG. 49 is a diagram showing one embodiment of a library detail screen.
Figure 50:
FIG. 50 is a diagram showing one embodiment of a recording confirmation screen.
Figure 51:
FIG. 51 is a diagram showing one embodiment of a subject detail screen.
Figure 52:
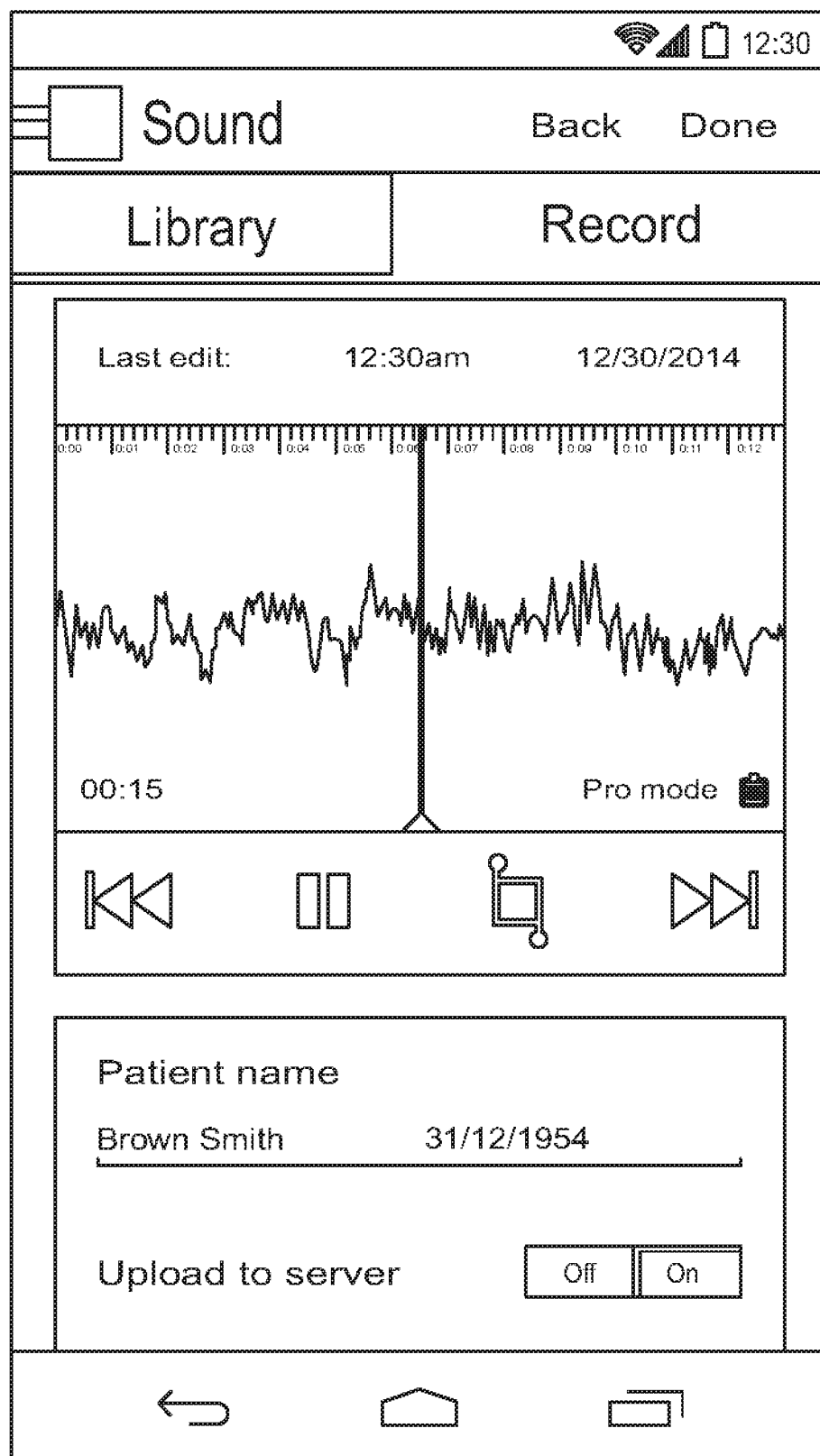
FIG. 52 is a diagram showing one embodiment of a recording detail screen.
Figure 53:
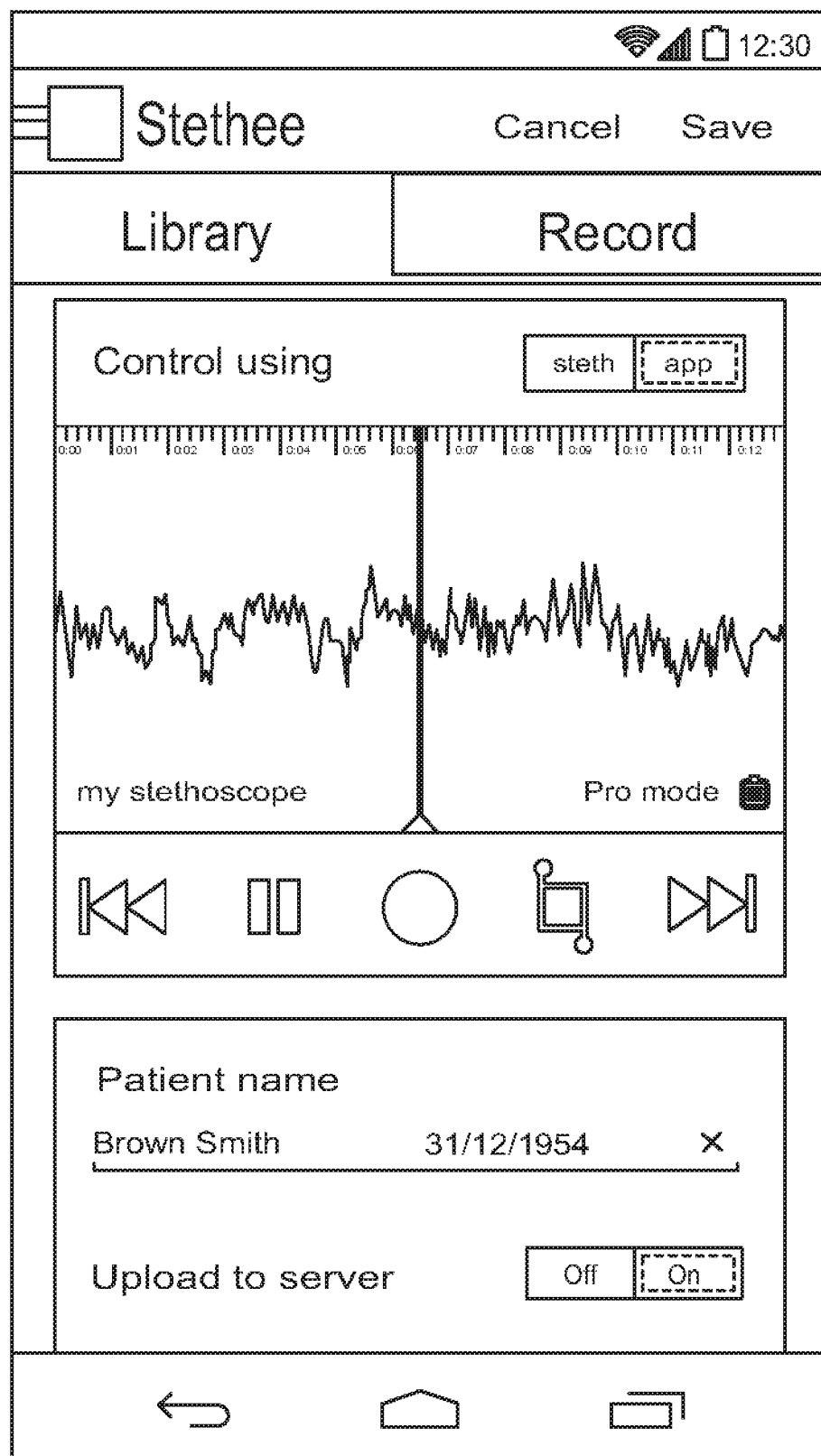
FIG. 53 is a diagram showing one embodiment of a recording control screen.
Figure 54:
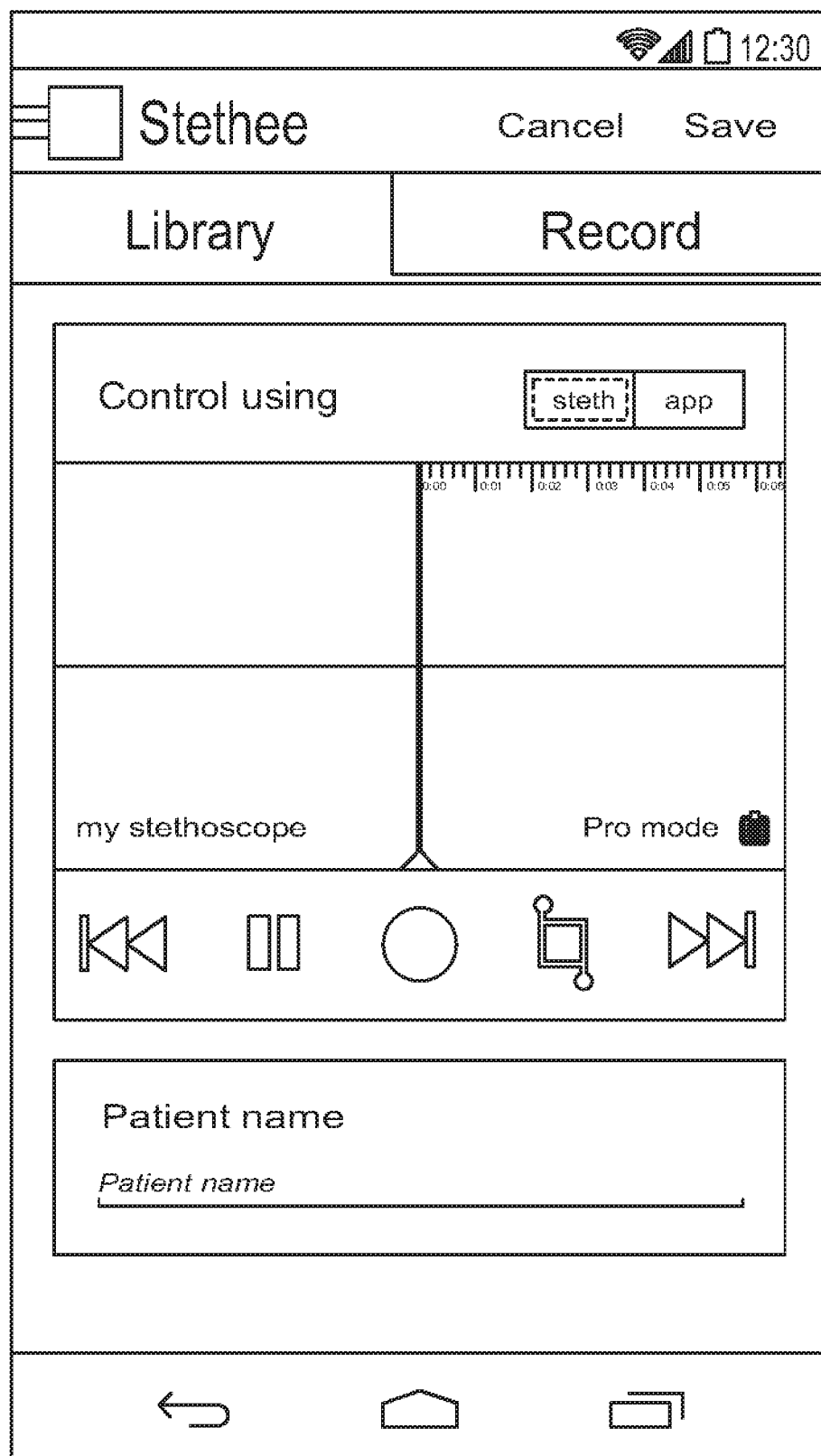
FIG. 54 is a diagram showing one embodiment of a local control screen.
Figure 55:
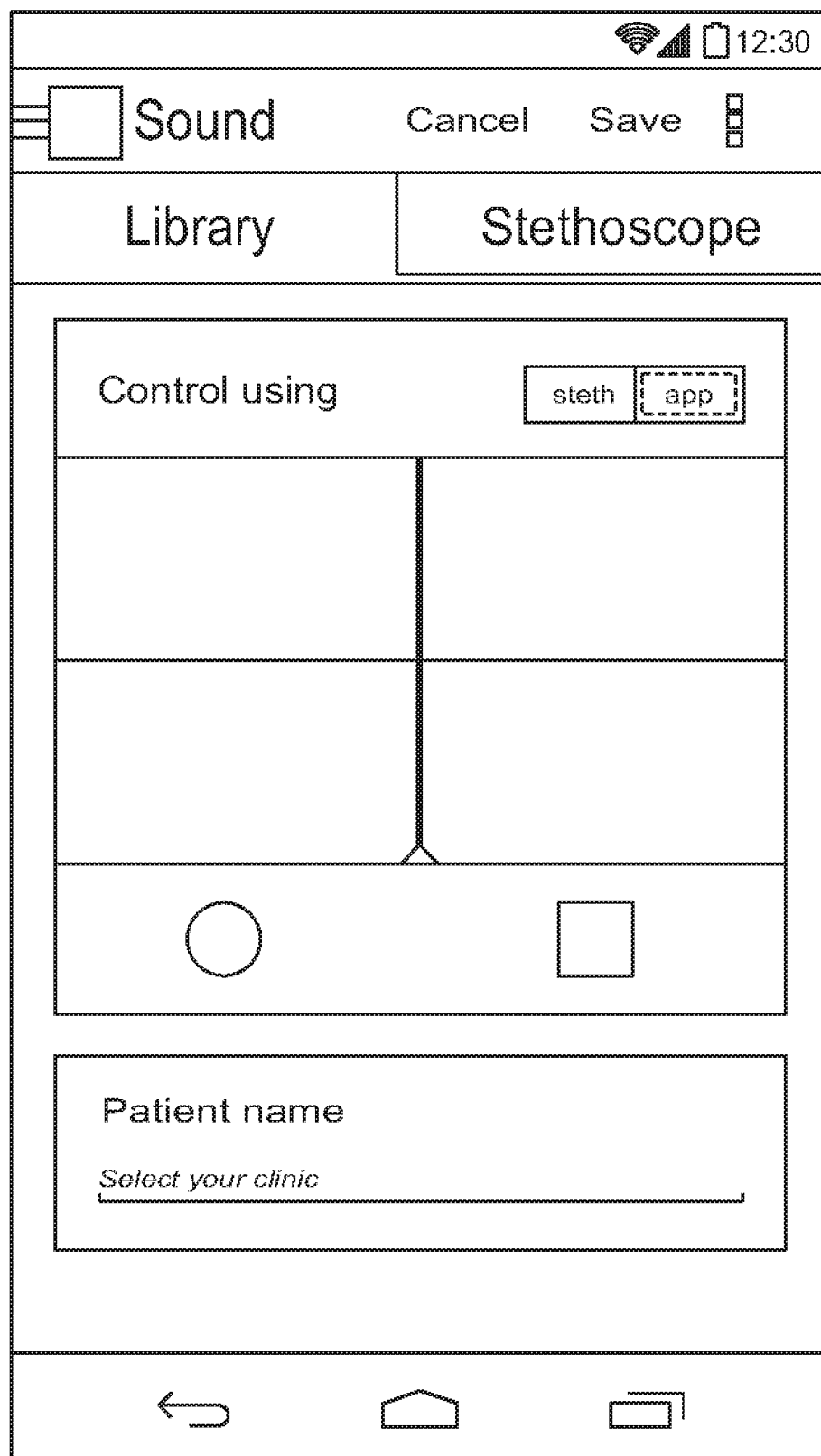
FIG. 55 is a diagram showing one embodiment of a remote control screen.
Figure 56:
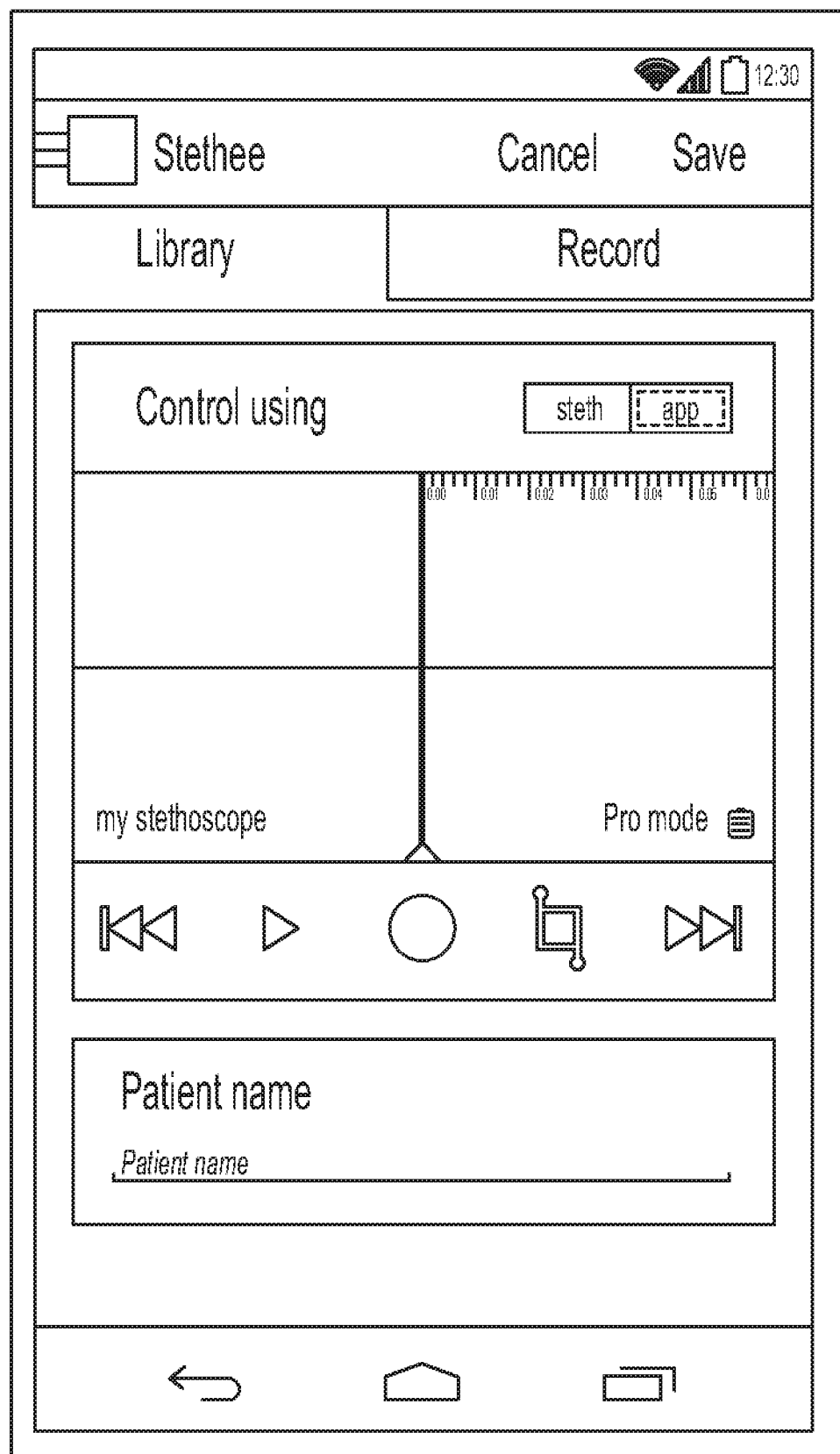
FIG. 56 is a diagram showing one embodiment of a start screen.
Figure 57:
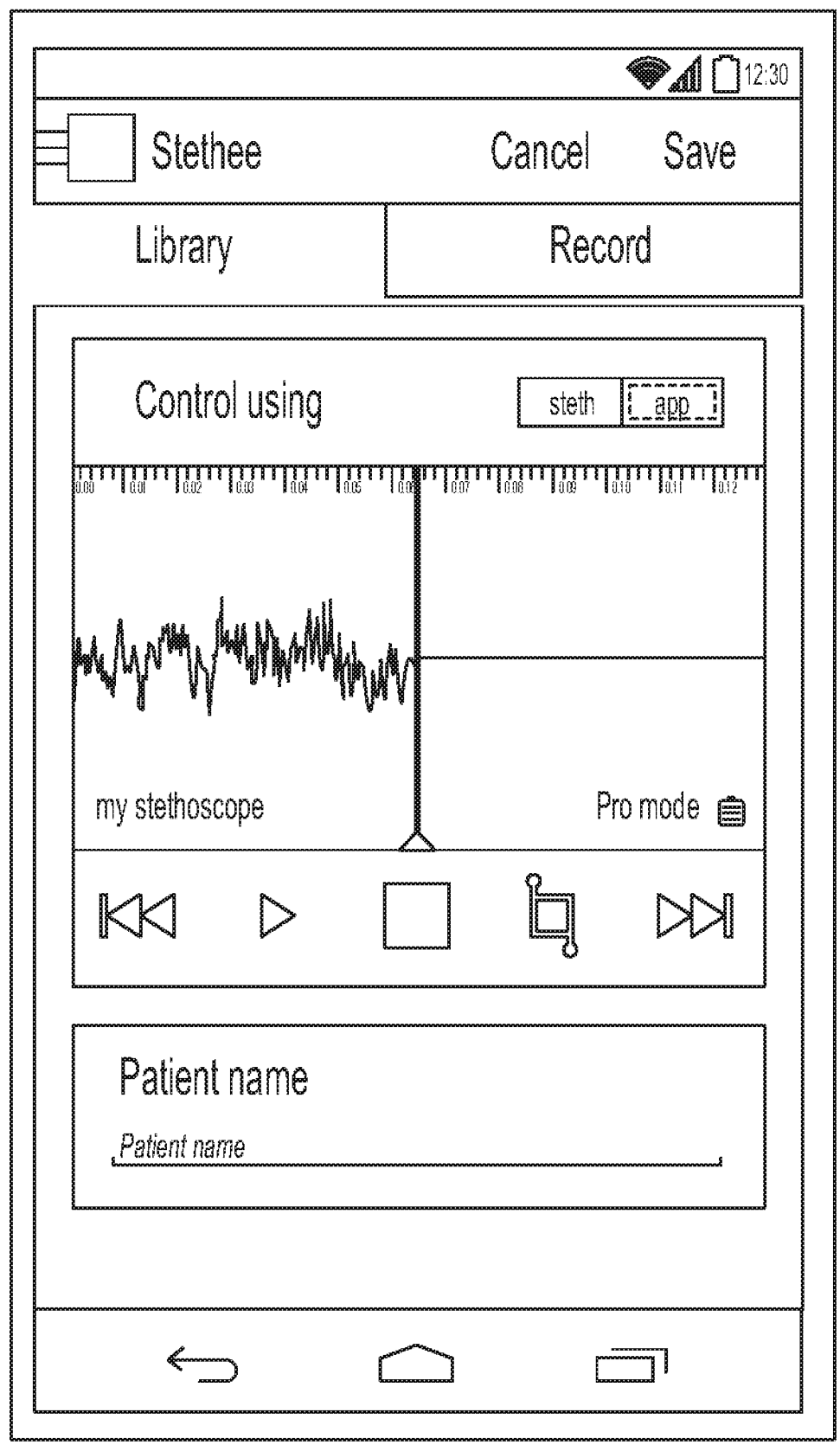
FIG. 57 is a diagram showing one embodiment of a recording progress screen.
Figure 58:
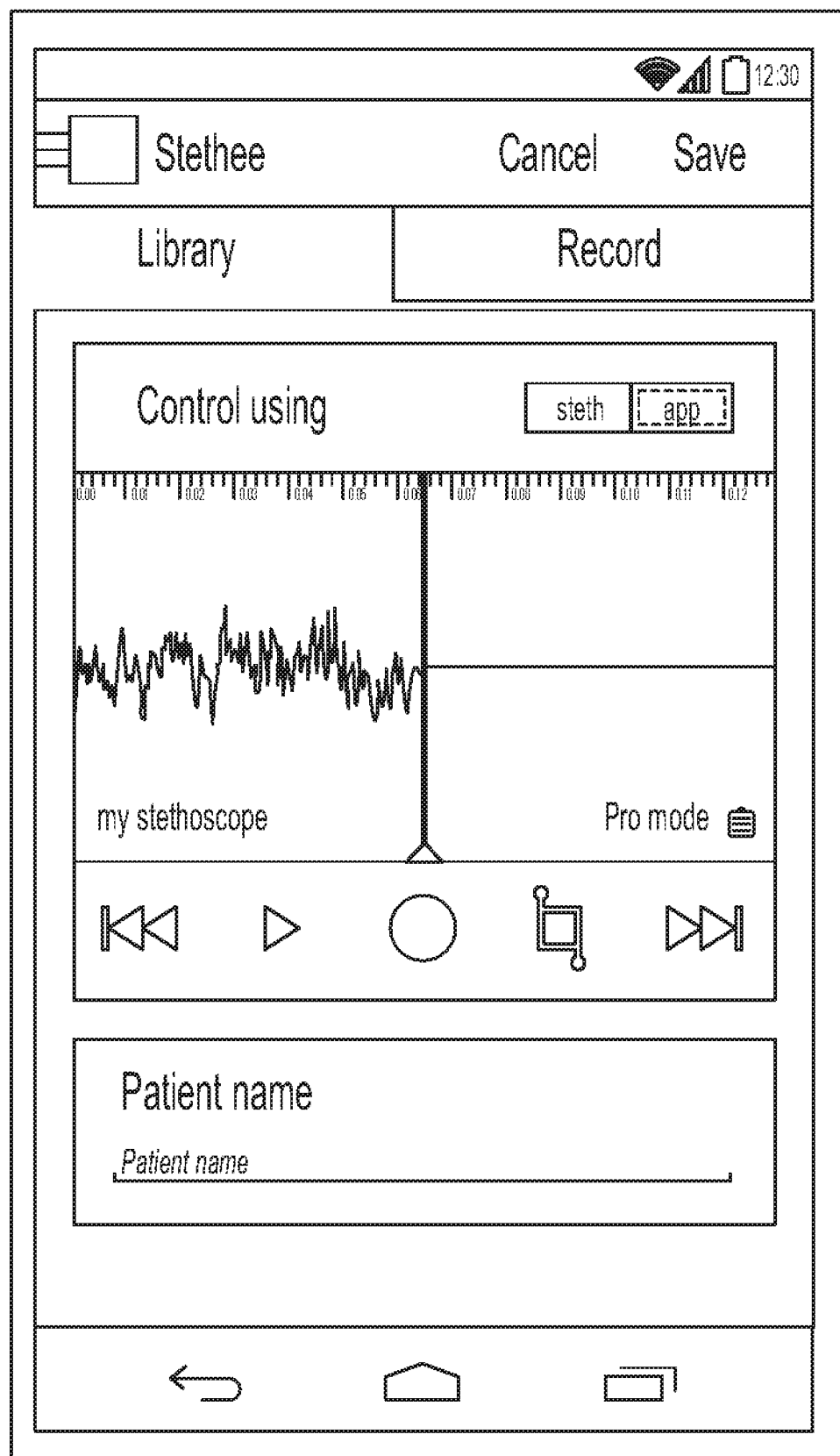
FIG. 58 is a diagram showing one embodiment of a stop screen.
Figure 59:
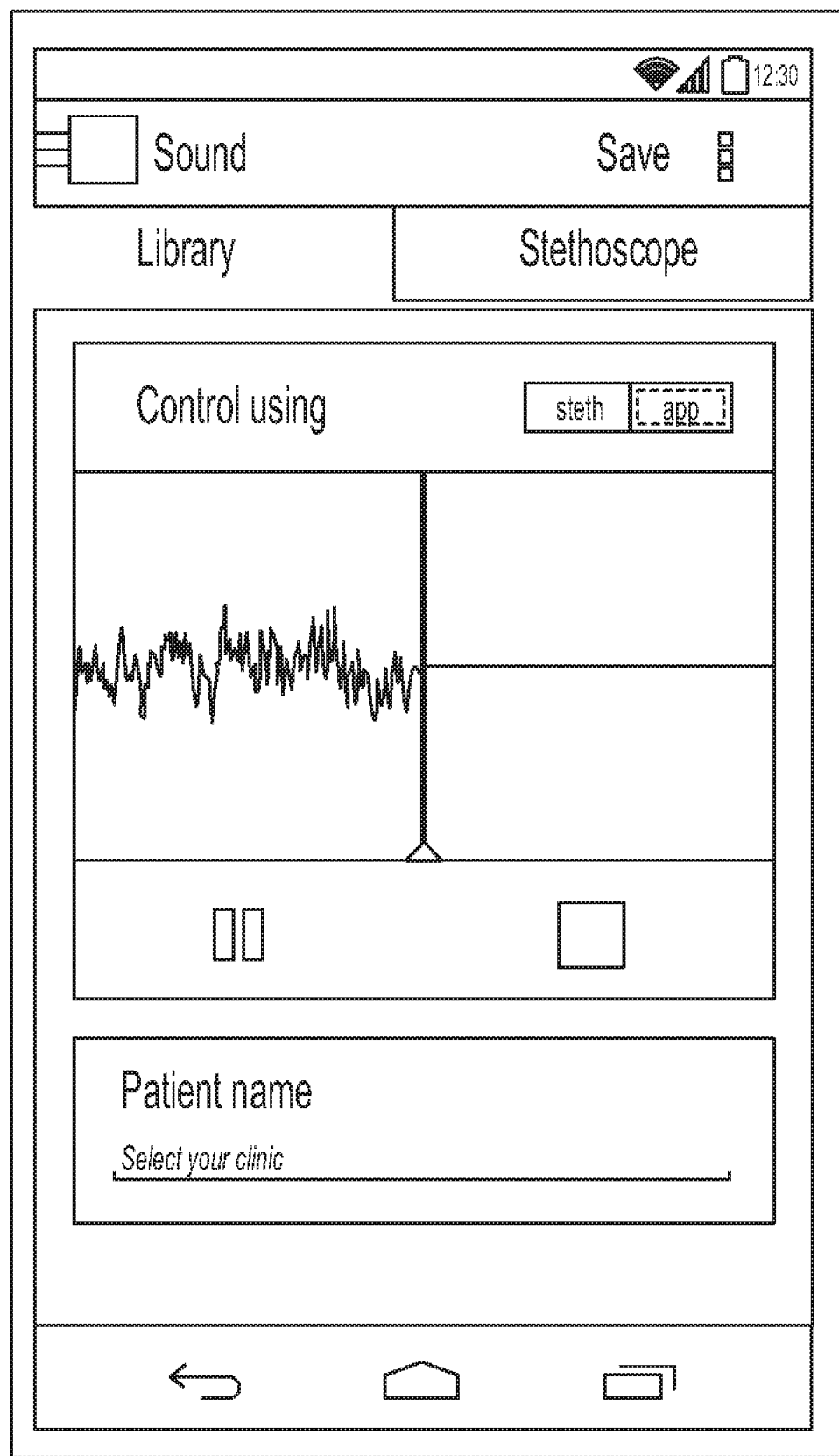
FIG. 59 is a diagram showing one embodiment of a playback screen.
Figure 60:
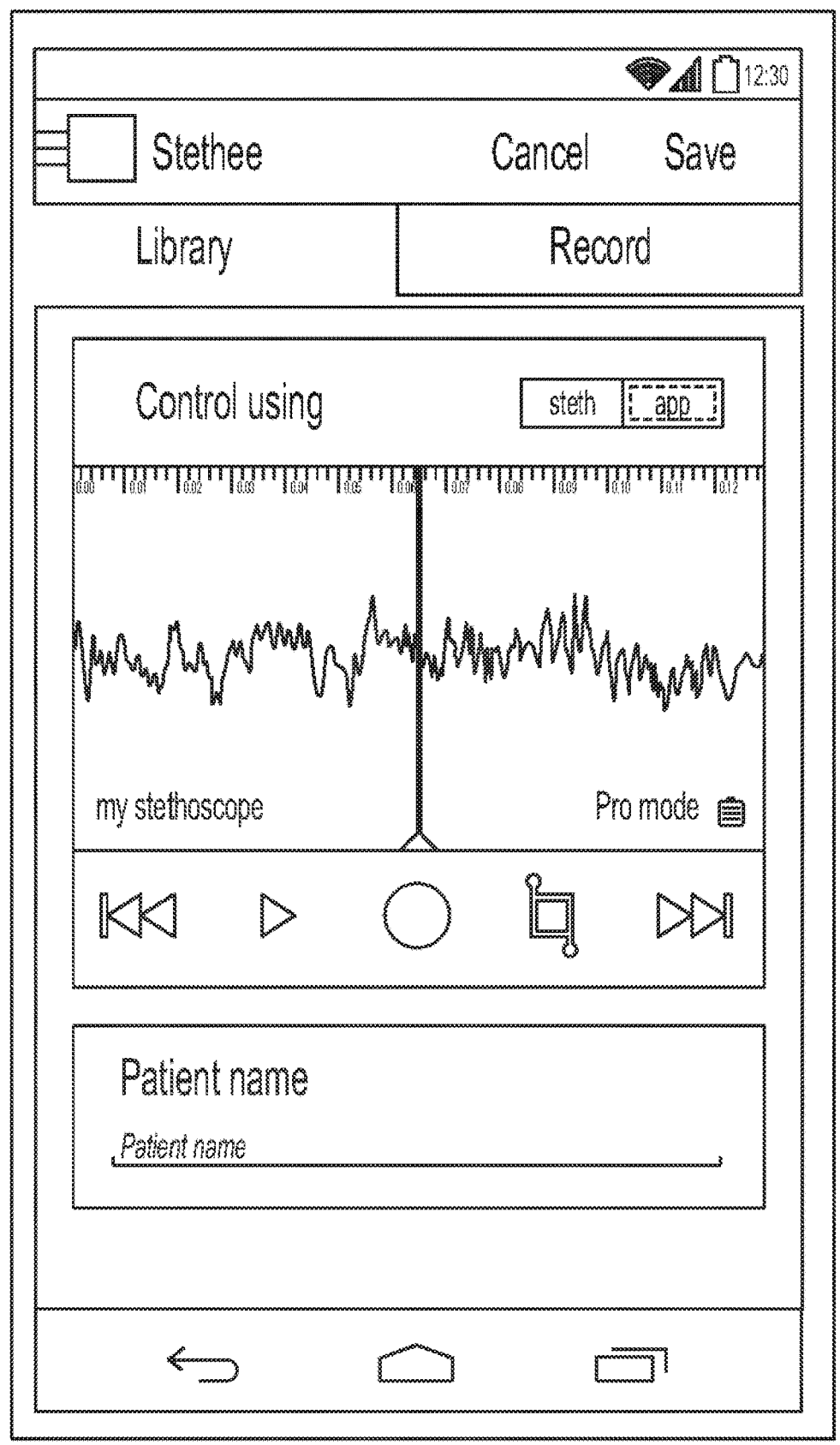
FIG. 60 is a diagram showing one embodiment of an expanded playback screen.
Figure 61:
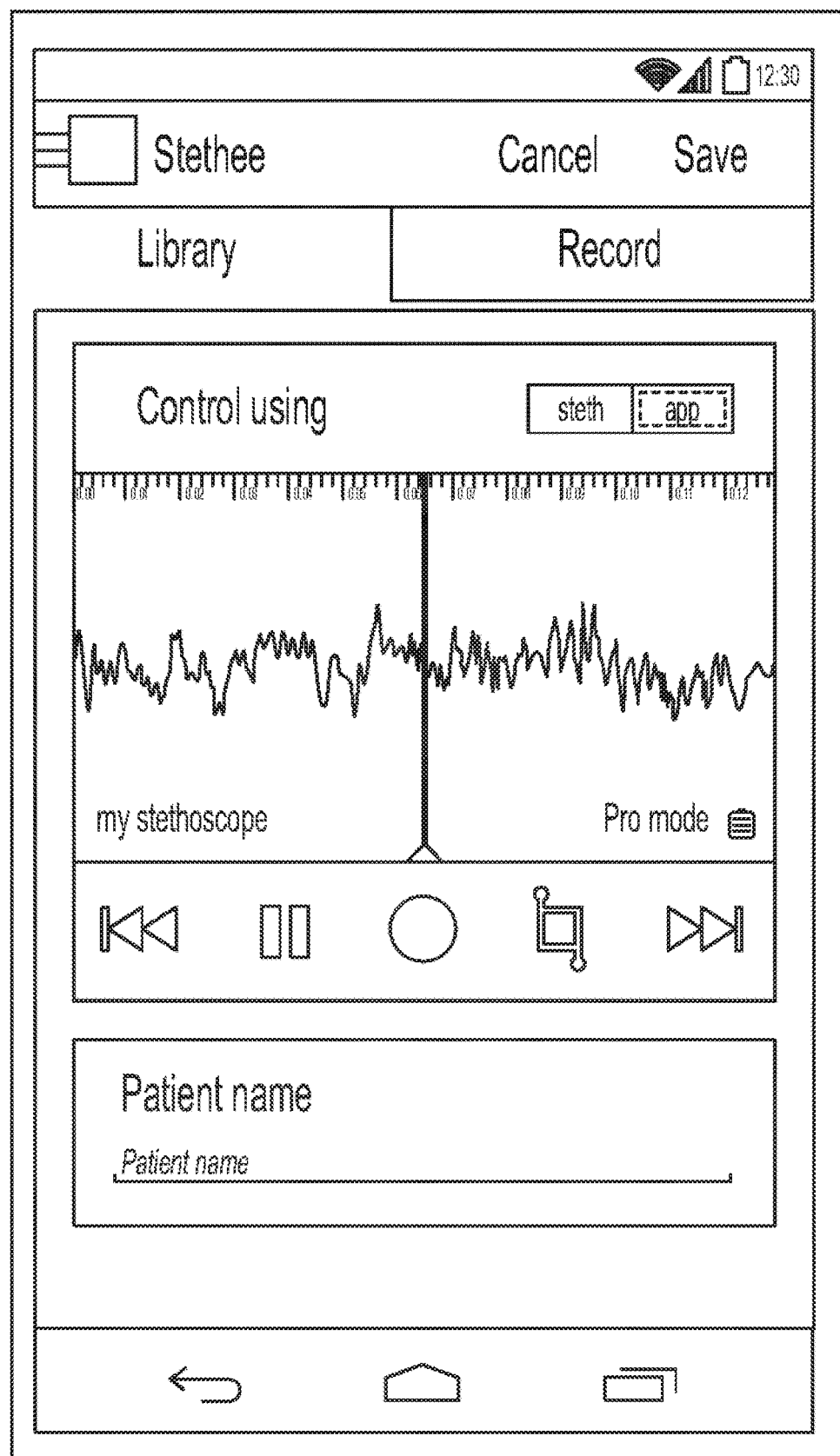
FIG. 61 is a diagram showing another embodiment of a playback screen.
Figure 62:
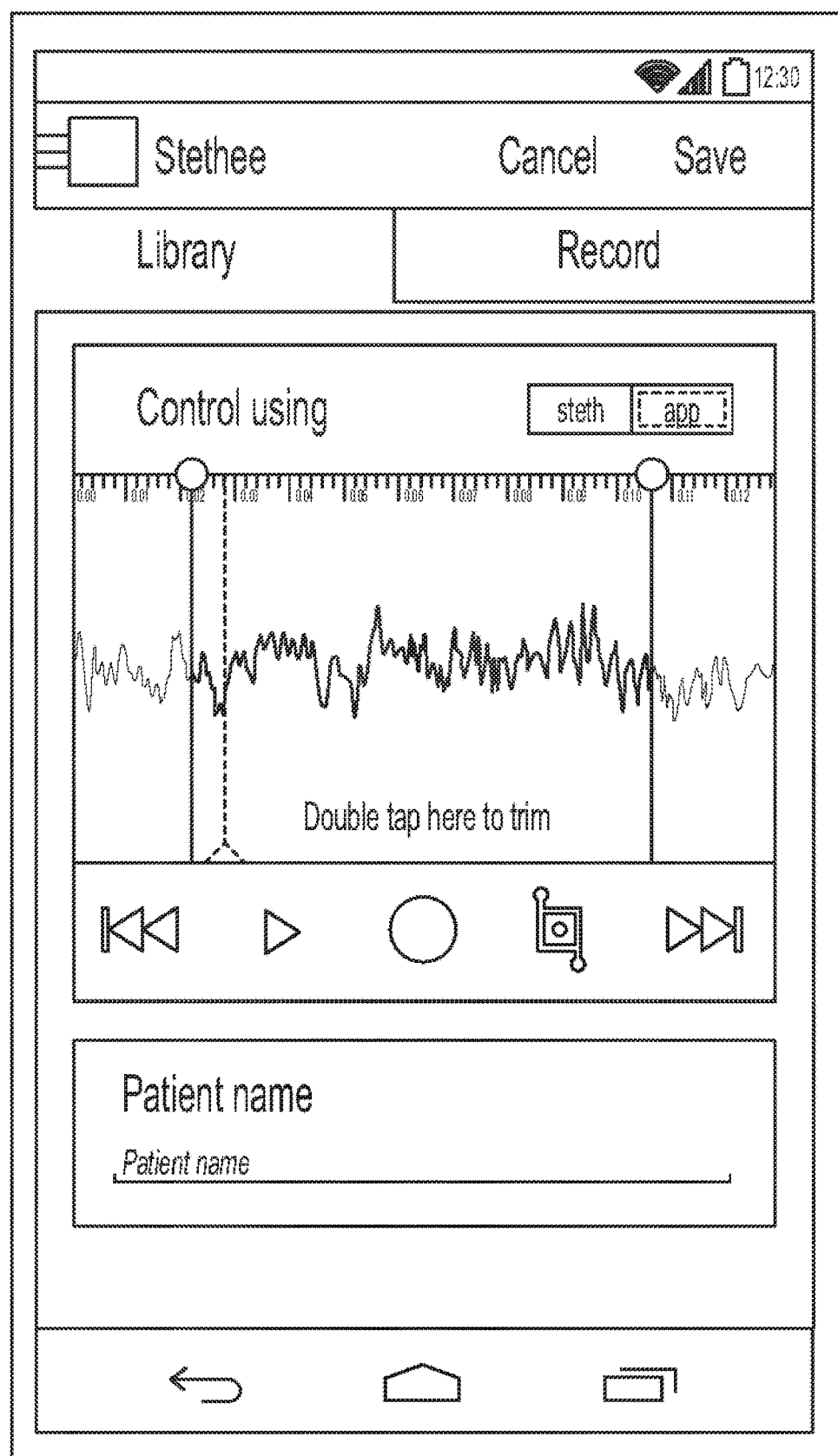
FIG. 62 is a diagram showing one embodiment of an editing screen.
Figure 63:
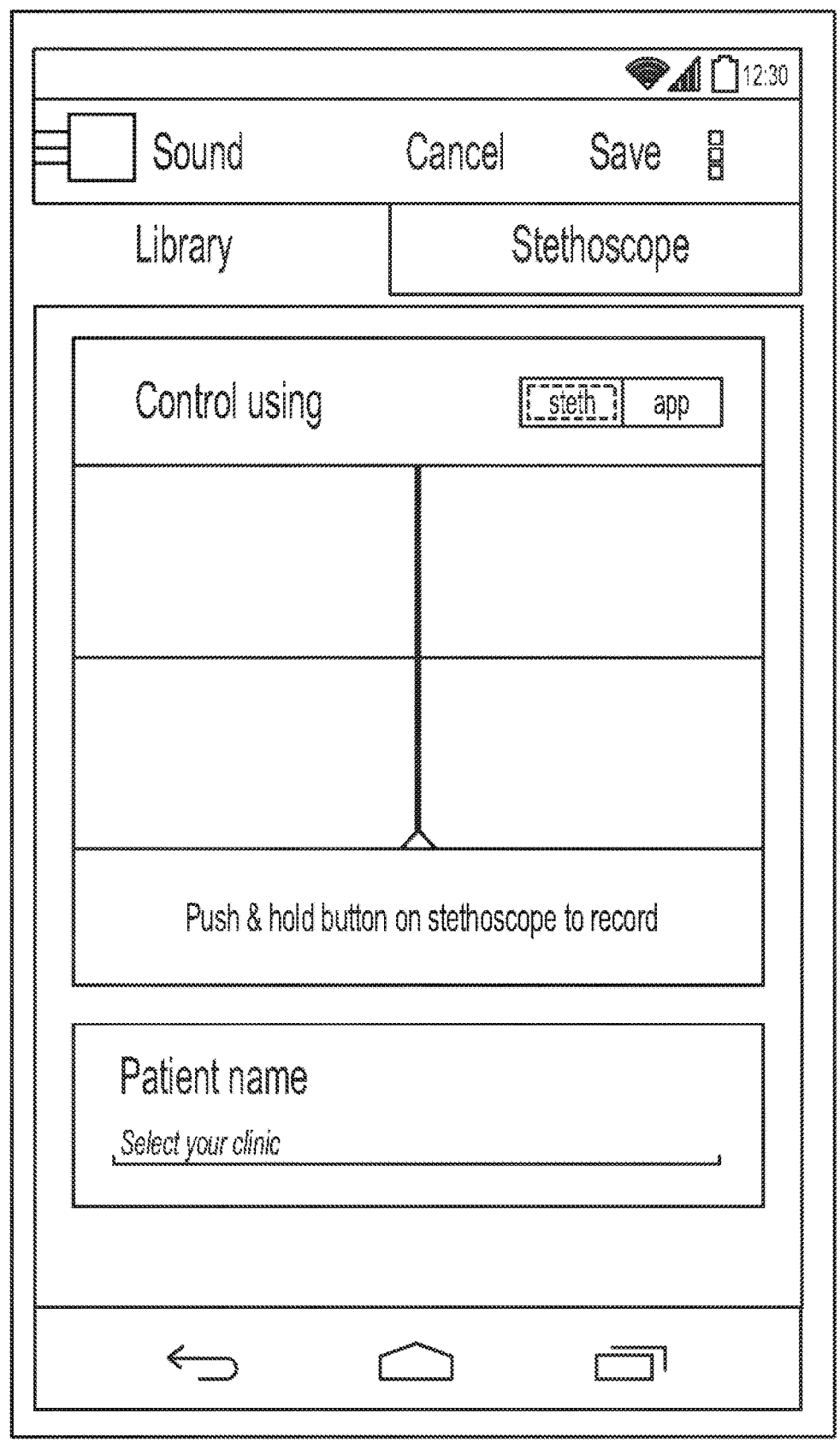
FIG. 63 is a diagram showing another embodiment of a start screen.
Figure 64:
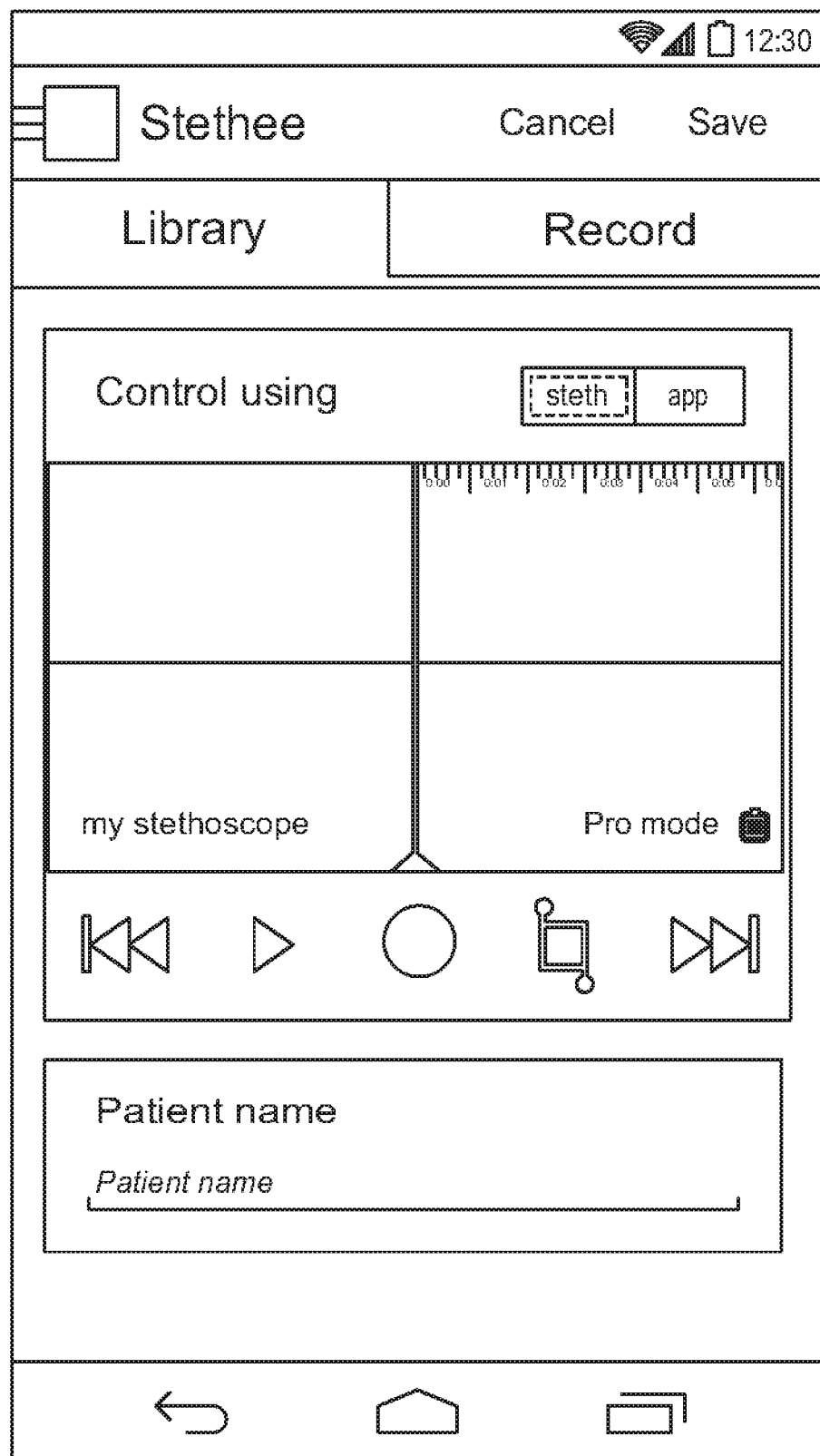
FIG. 64 is a diagram showing another embodiment of a recording progress screen.

FIGS. 48-64 illustrate embodiments of screens showing various features of the stethoscopes described herein that can be viewable in conjunction with the systems and methods of the stethoscope as they are configurable and usable via a paired electronic device's GUI. FIG. 48 shows a library screen identifying previously recorded sounds, including subject name, date and time the sound data was gathered, and a length of the recorded sound. FIG. 49 shows a library detail screen that is similar to the library screen but also includes an option to play each of the recorded sounds. FIG. 50 shows a recording confirmation screen indicating that a recording session has ended (e.g., the stethoscope's microphone(s) have been turned off) and that the recorded data has been saved locally at the stethoscope and remotely at a server. FIG. 51 shows a subject detail screen listing all recordings for a selected subject, which may be accessed by selecting the subject's name from the library screen or the library detail screen. FIG. 52 shows a recording detail screen providing a recording of a session, including a playback feature and a remote upload on/off feature. FIG. 53 shows a recording control screen that allows the user to select whether the recording is controlled locally by the stethoscope or remotely via electronic device APP. The recording control screen also includes the playback feature and the remote upload on/off feature. FIG. 54 shows a local control screen. FIG. 55 shows a remote control screen. FIG. 56 shows a start screen that allows a recording to be started. FIG. 57 shows a recording progress screen after the recording has been started via the start screen of FIG. 56. FIG. 58 shows a stop screen that shows the recording after it has been stopped via the recording progress screen of FIG. 57. FIG. 59 shows a playback screen that allows the playing of the recording stopped via the stop screen of FIG. 58. FIG. 60 shows an expanded playback screen that shows the recording of FIG. 58 on a larger timescale than the recording is shown in FIG. 59 to help make the displayed waveform easier to interpret. The playback screen that allows the playing of the expanded recording of FIG. 60, which is paused in FIG. 60. FIG. 61 shows another playback screen that allows the pausing of the expanded recording of FIG. 60, which is playing in FIG. 61. FIG. 62 shows an editing screen that allows the recording to be trimmed to a subset of the recorded time. FIG. 63 shows another start screen. FIG. 64 shows a recording progress screen after the recording has been started via the start screen of FIG. 63.

Figure 65:
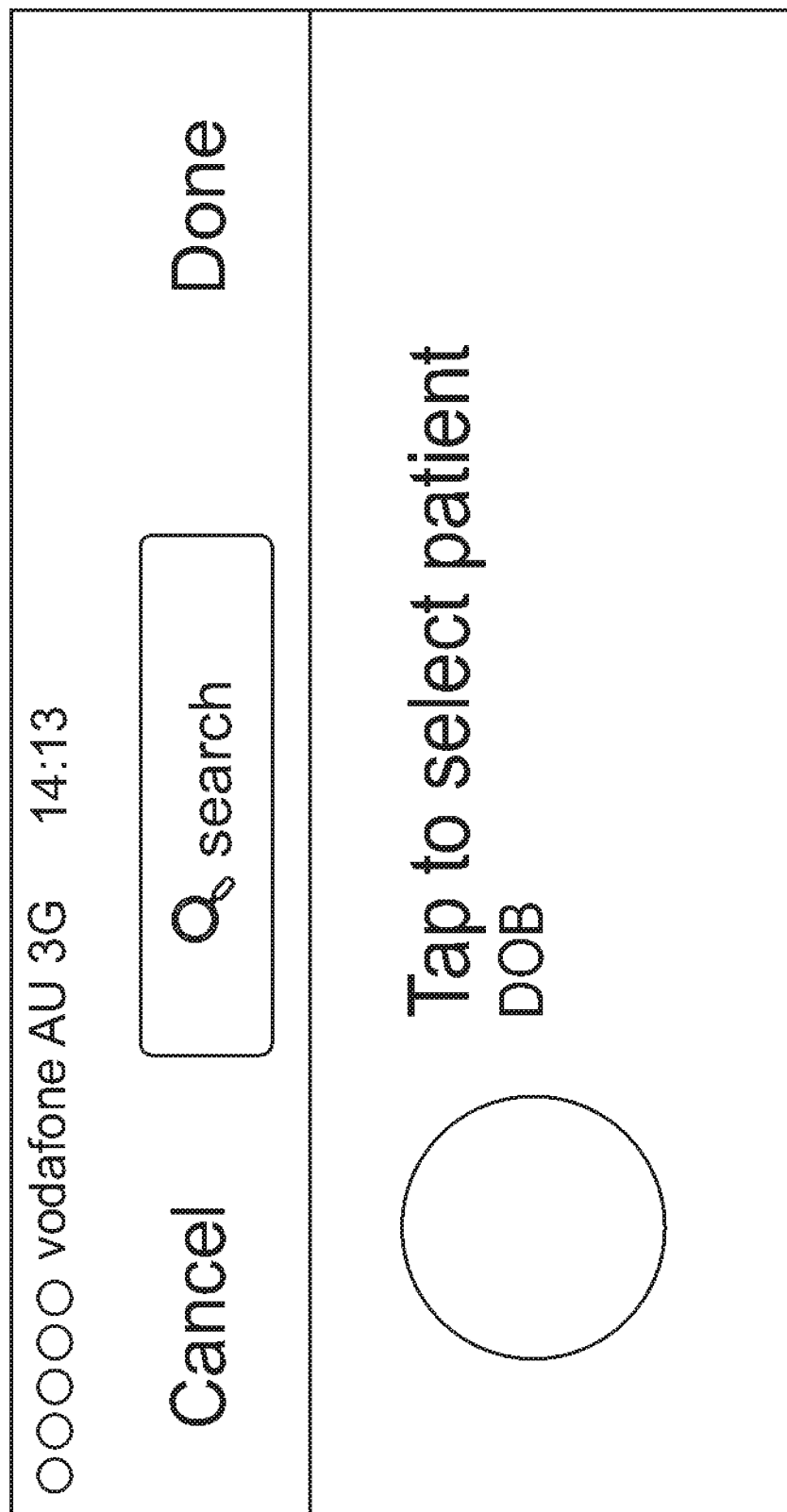
FIG. 65 is a diagram showing one embodiment of a subject select screen.
Figure 66:
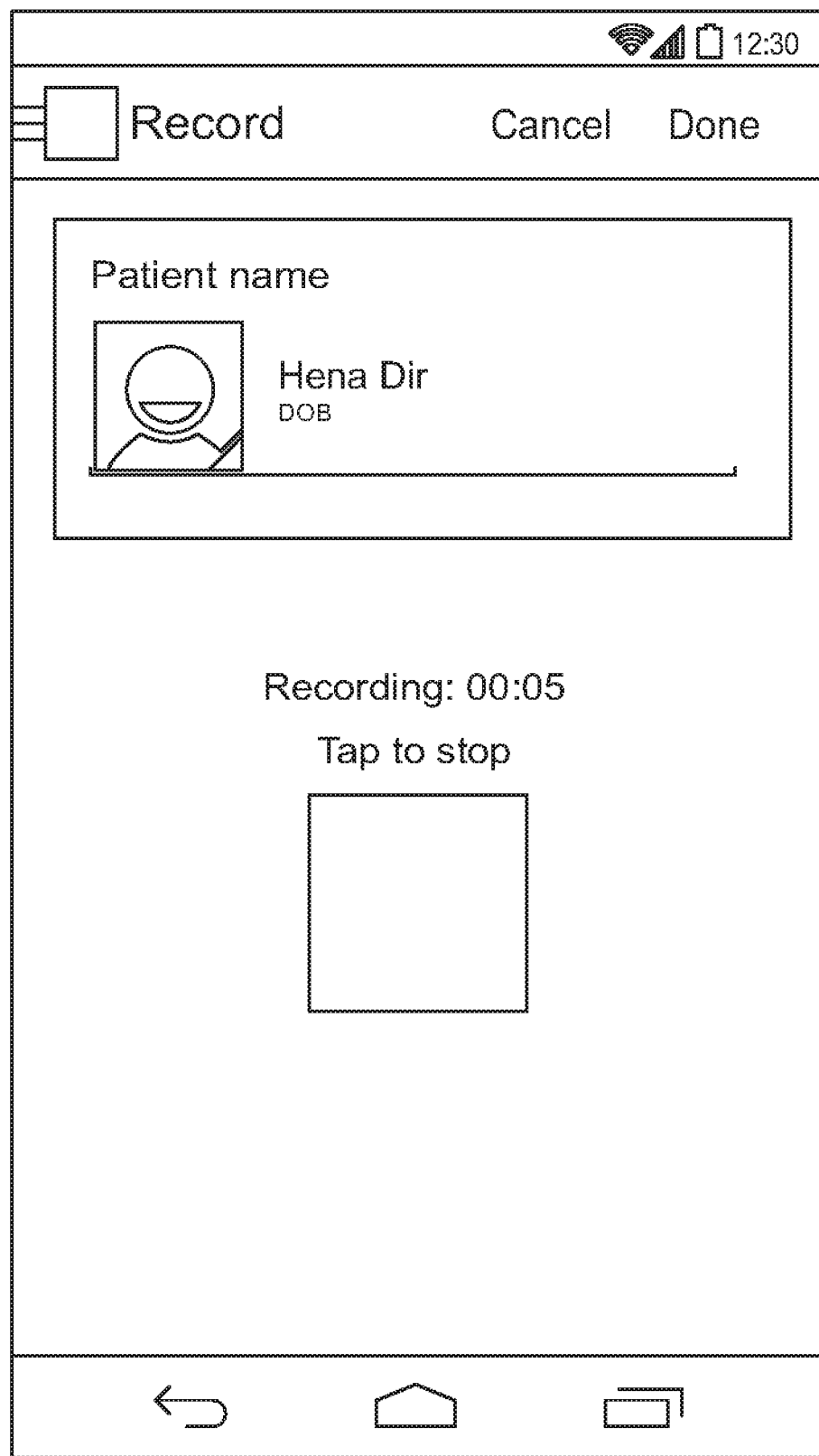
FIG. 66 is a diagram showing another embodiment of a recording progress screen.

FIG. 65 illustrates an embodiment of a subject (patient) select screen that allows a subject to be chosen for use with the stethoscope. FIG. 66 illustrates an embodiment of a recording progress screen for the patient selected via the subject select screen of FIG. 65.

Figure 67:
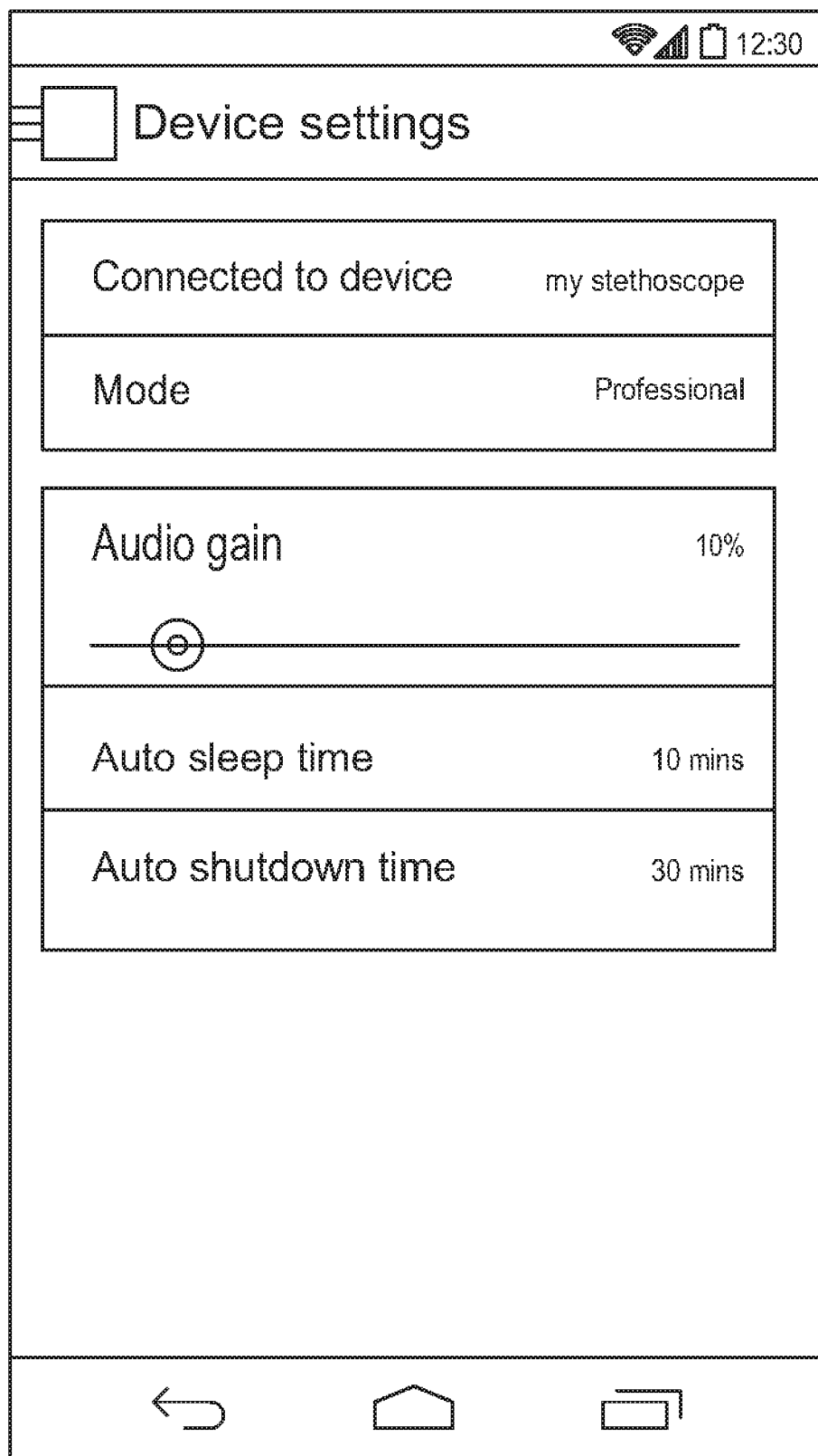
FIG. 67 is a diagram showing one embodiment of a device settings screen for a professional mode of operation.
Figure 68:
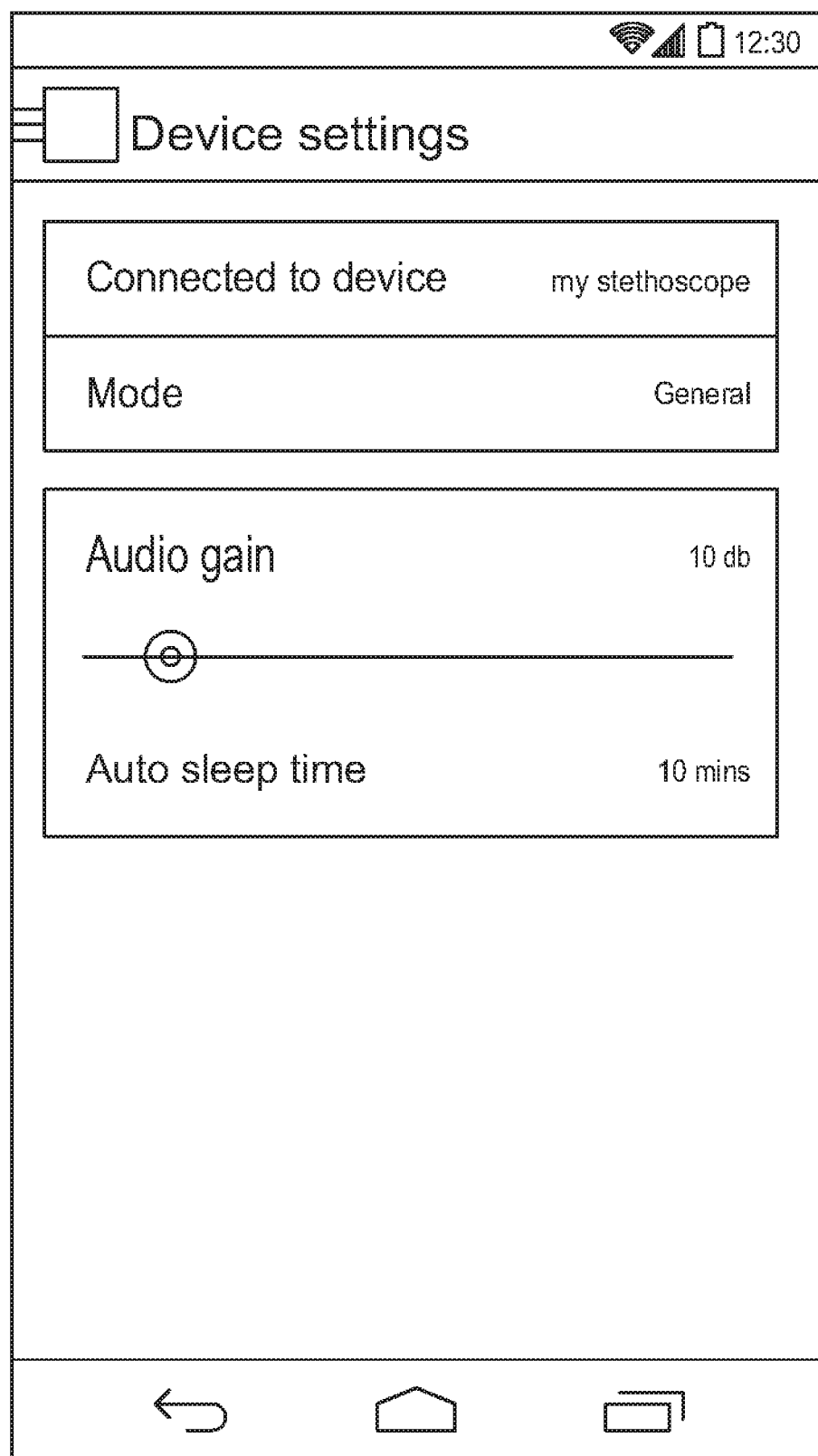
FIG. 68 is a diagram showing one embodiment of a device settings screen for a general mode of operation.
Figure 69:
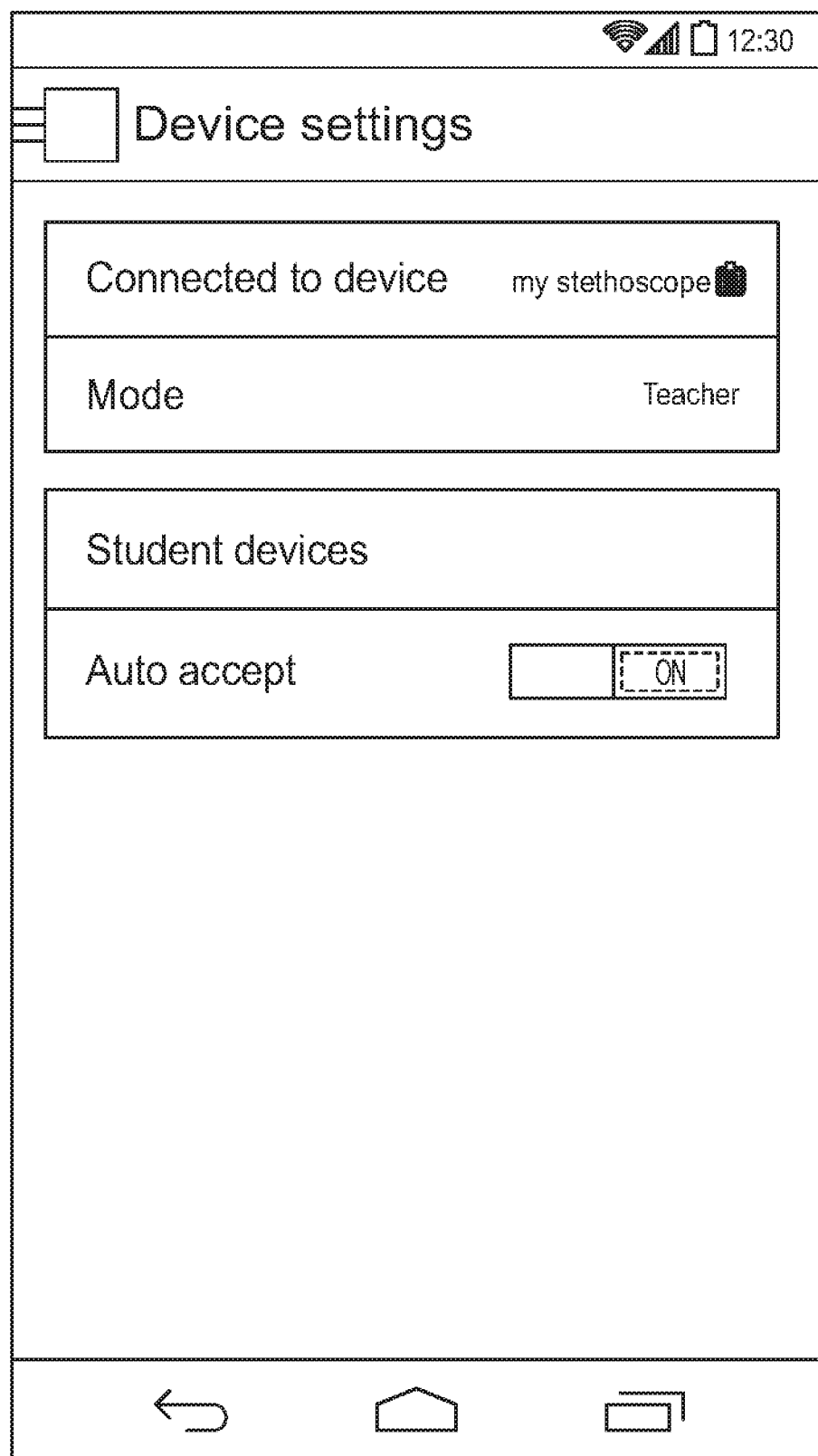
FIG. 69 is a diagram showing one embodiment of a device settings screen for a teacher mode of operation.
Figure 70:
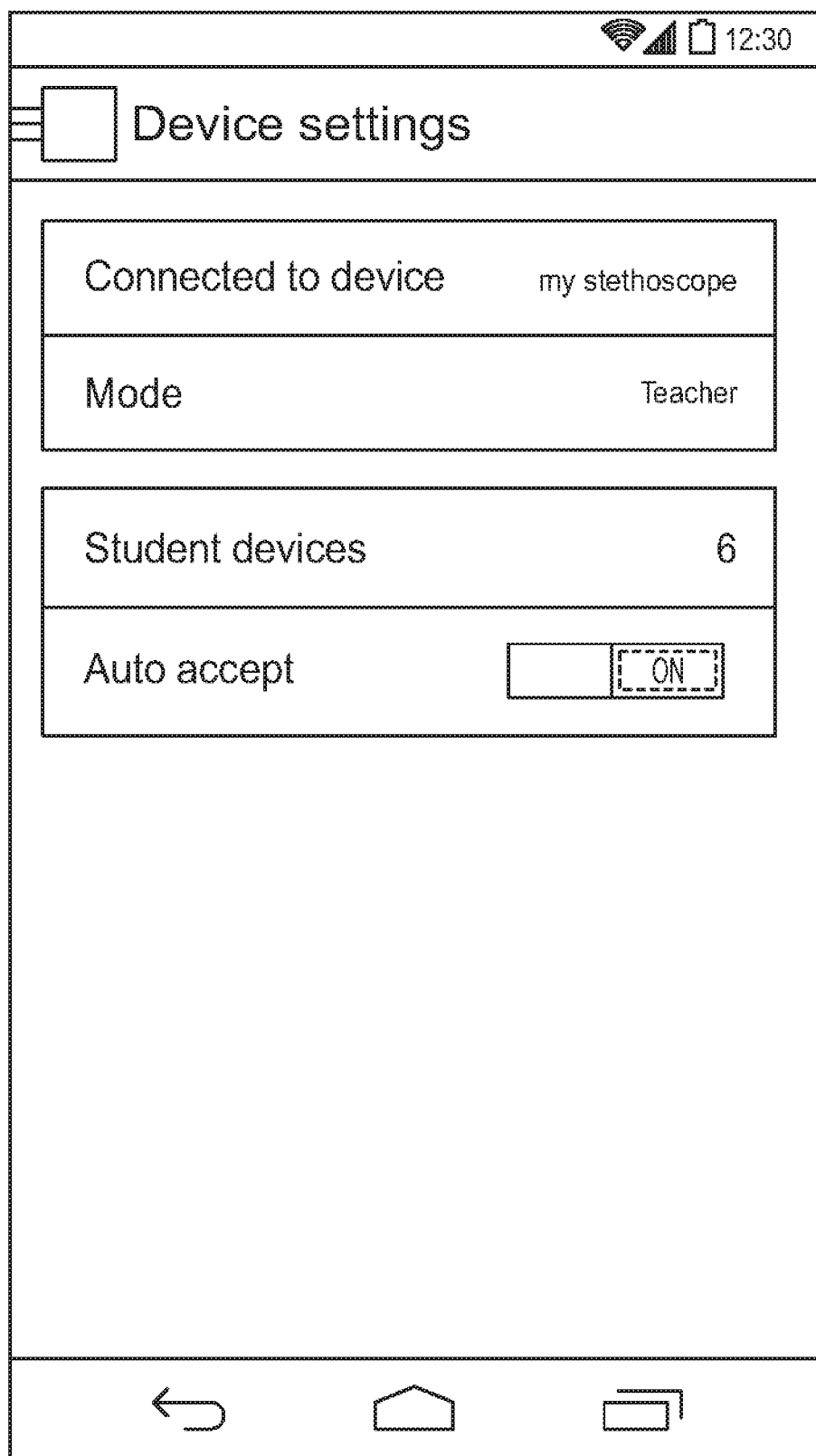
FIG. 70 is a diagram showing the device settings screen of FIG. 69 after linking of student stethoscopes.
Figure 71:
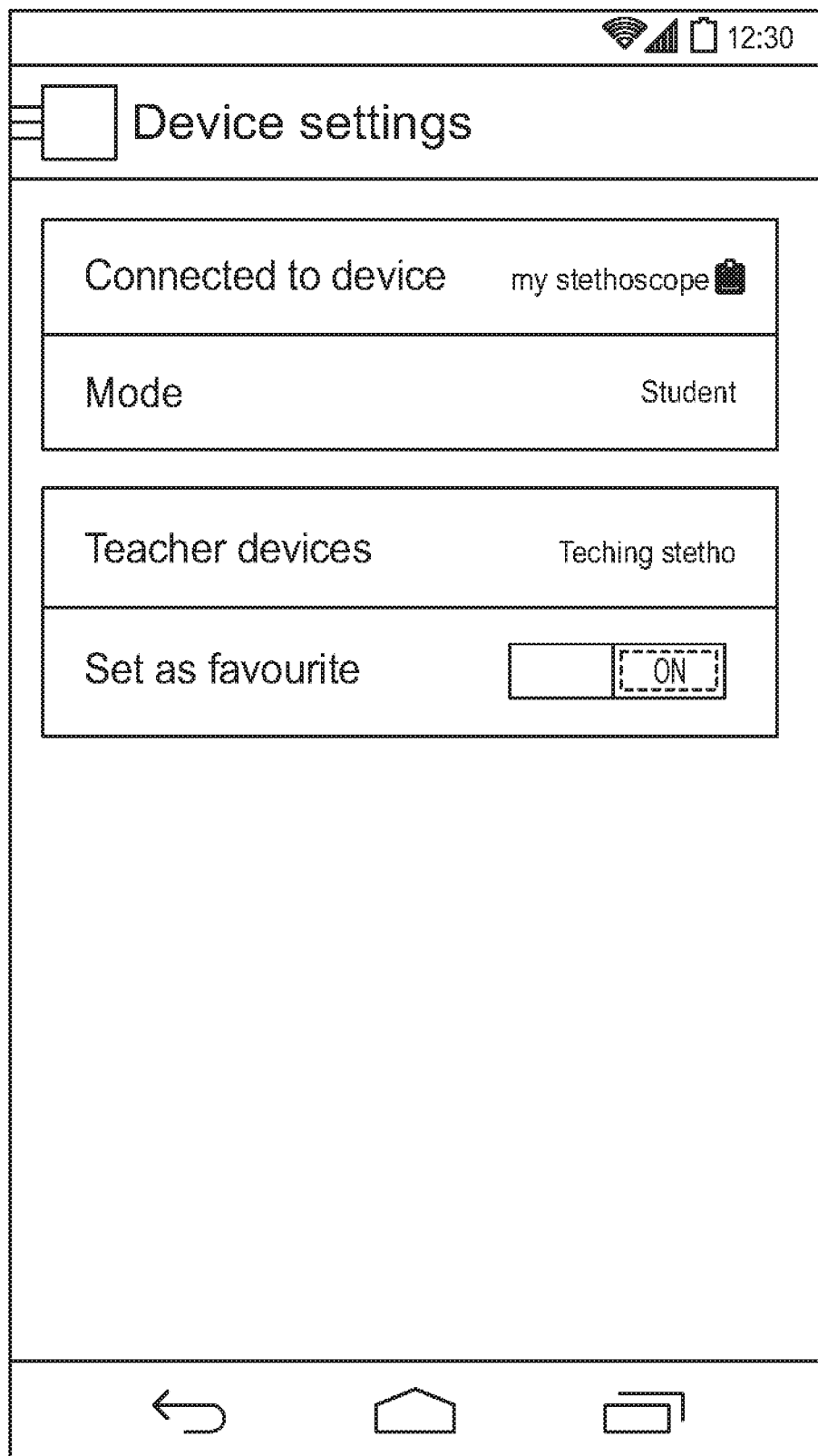
FIG. 71 is a diagram showing one embodiment of a device settings screen for a student mode of operation.
Figure 72:
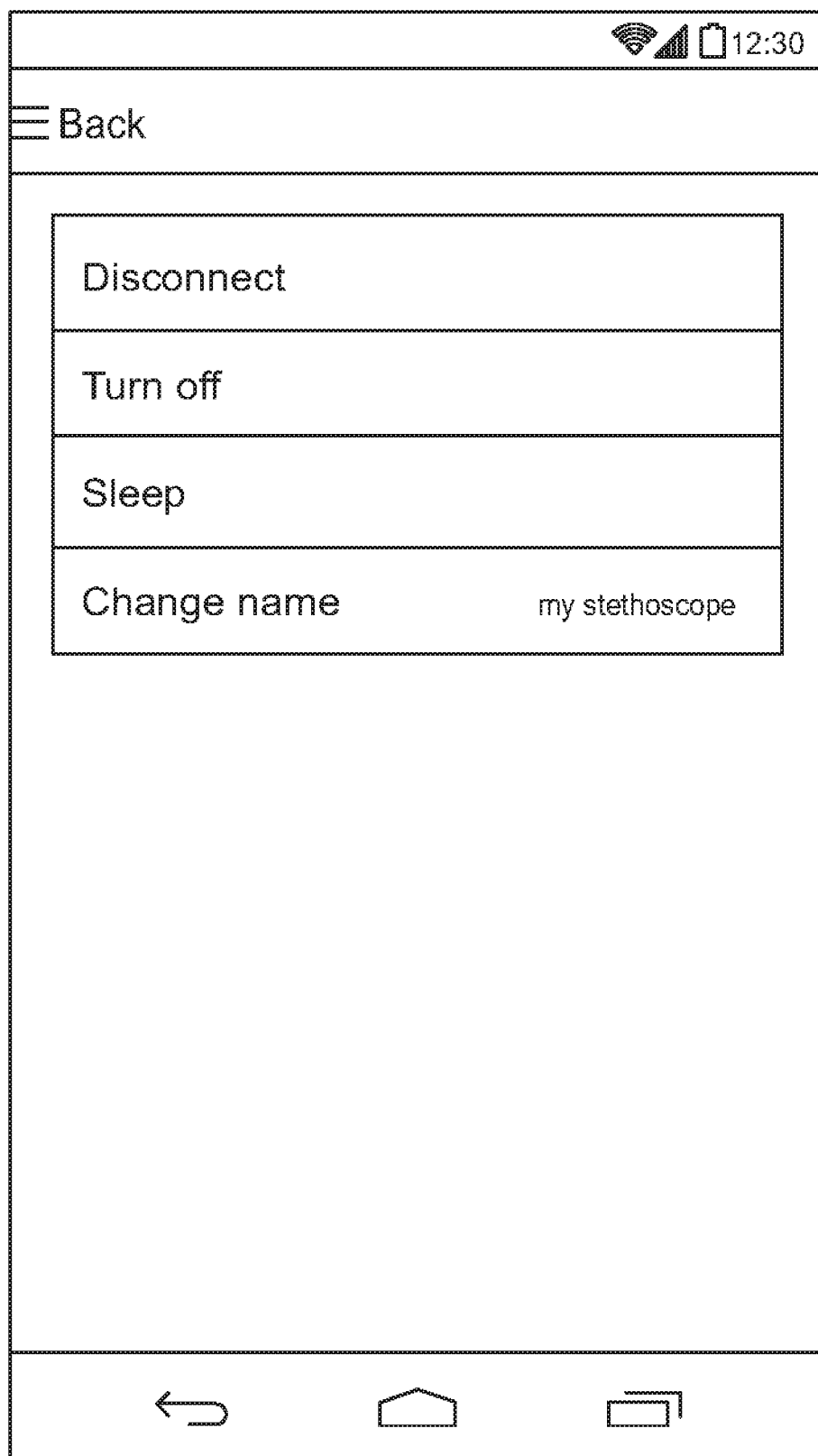
FIG. 72 is a diagram showing one embodiment of a stethoscope settings screen.
Figure 73:
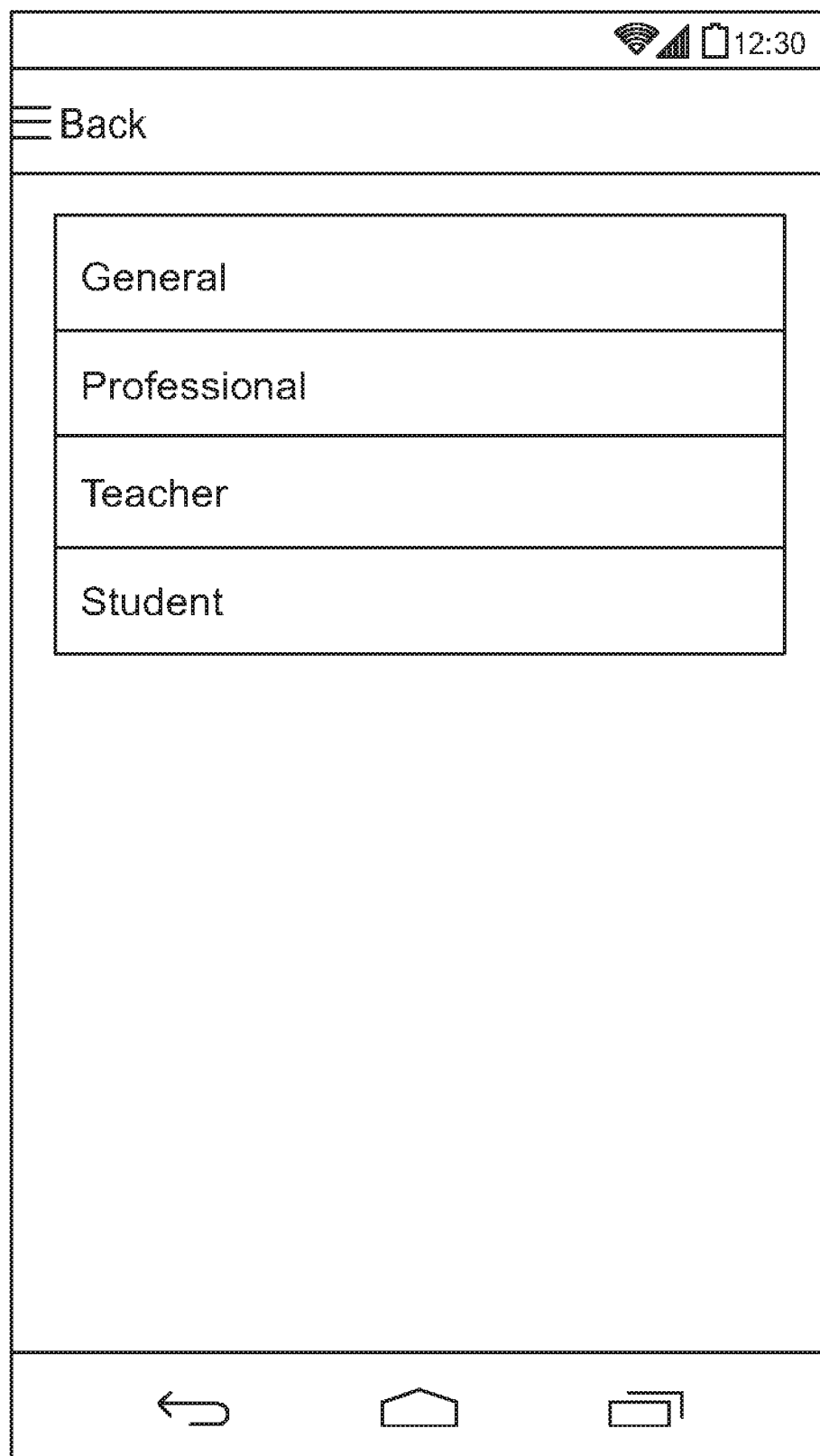
FIG. 73 is a diagram showing one embodiment of a mode selection screen.
Figure 74:
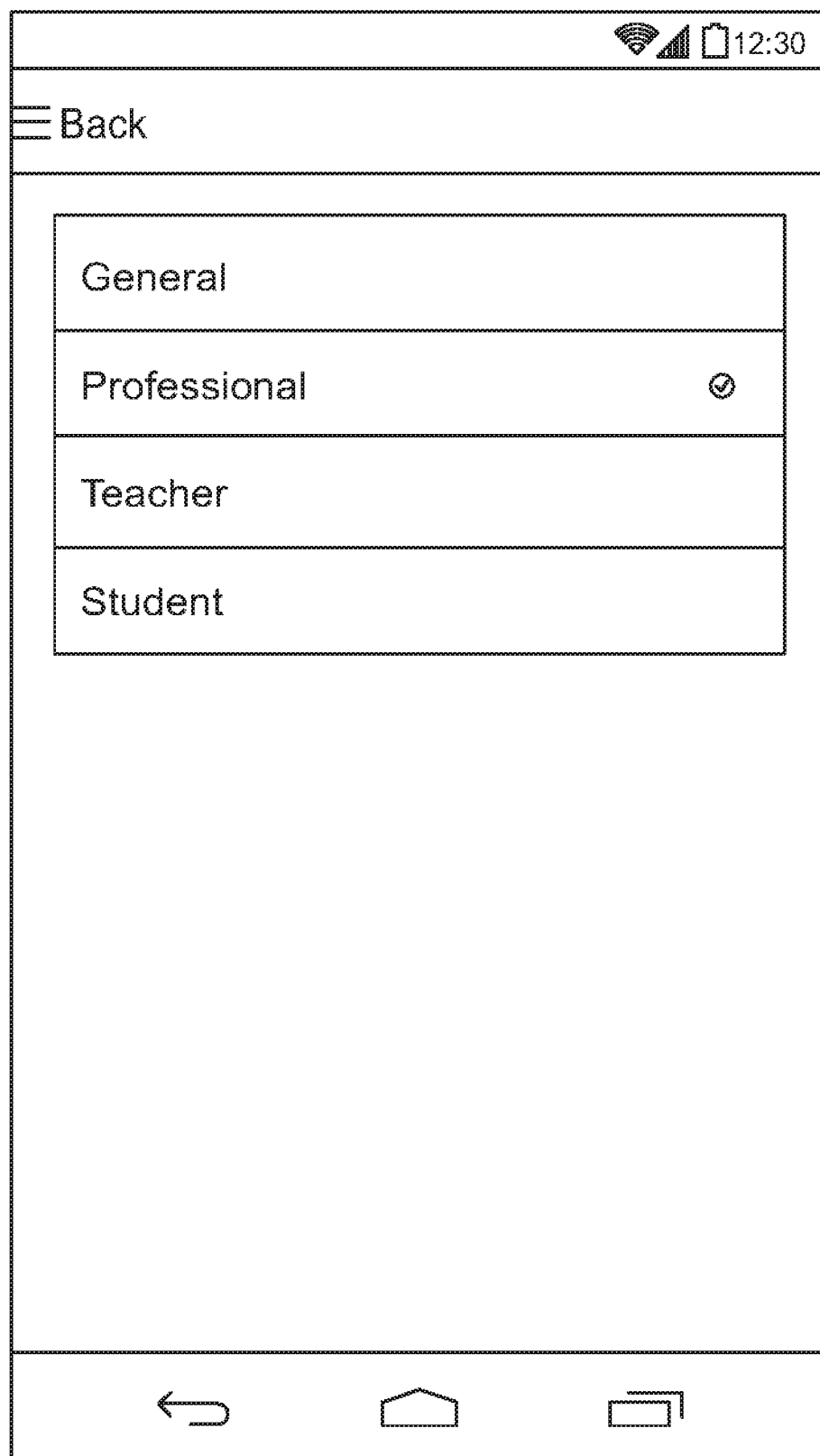
FIG. 74 is a diagram showing the mode selection screen of FIG. 73 with a mode selected.
Figure 75:
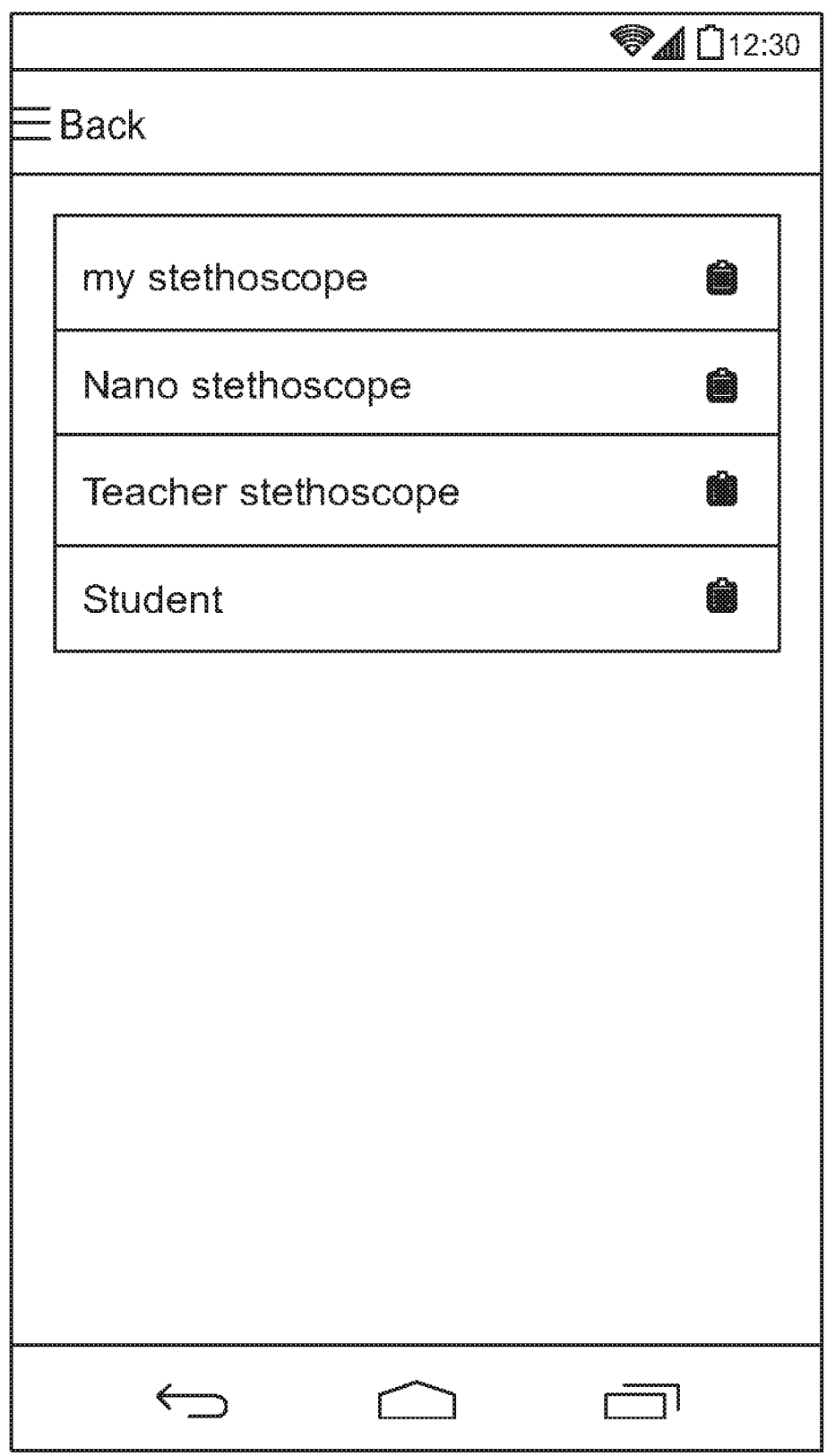
FIG. 75 is a diagram showing one embodiment of a linked devices screen.
Figure 76:
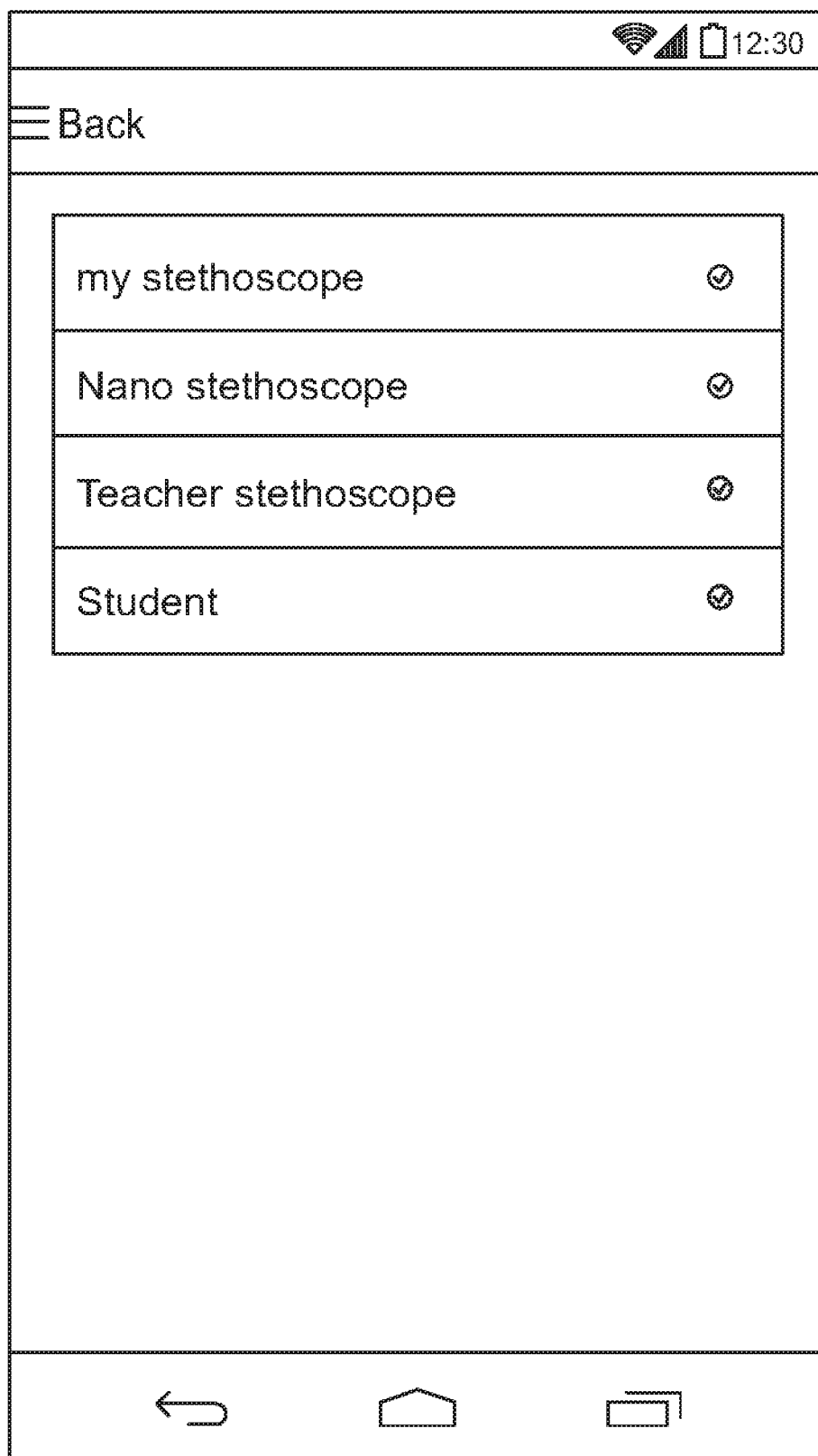
FIG. 76 is a diagram showing the linked devices screen of FIG. 75 indicating linked devices.
Figure 77:
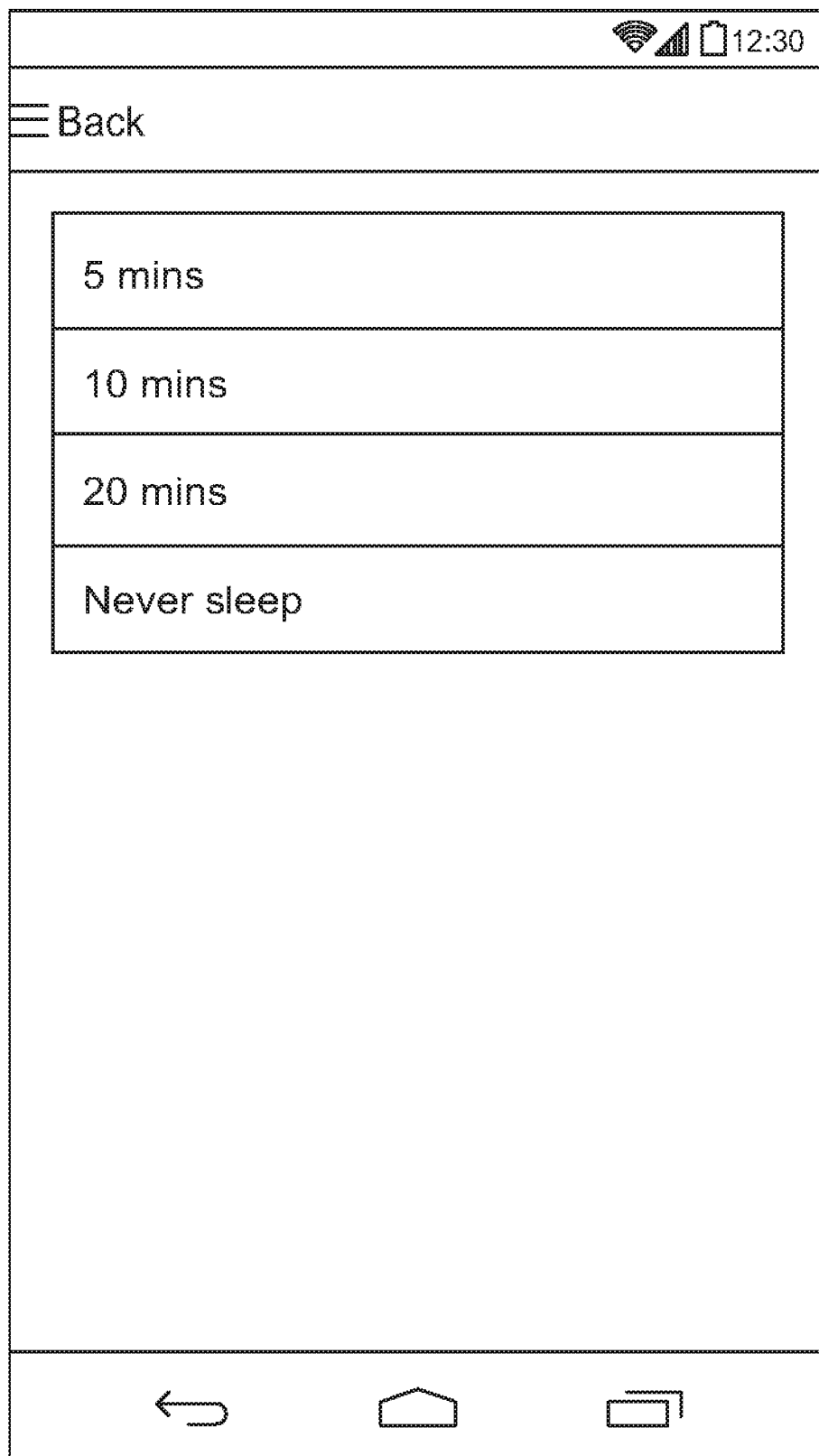
FIG. 77 is a diagram showing one embodiment of a sleep selection screen.
Figure 78:
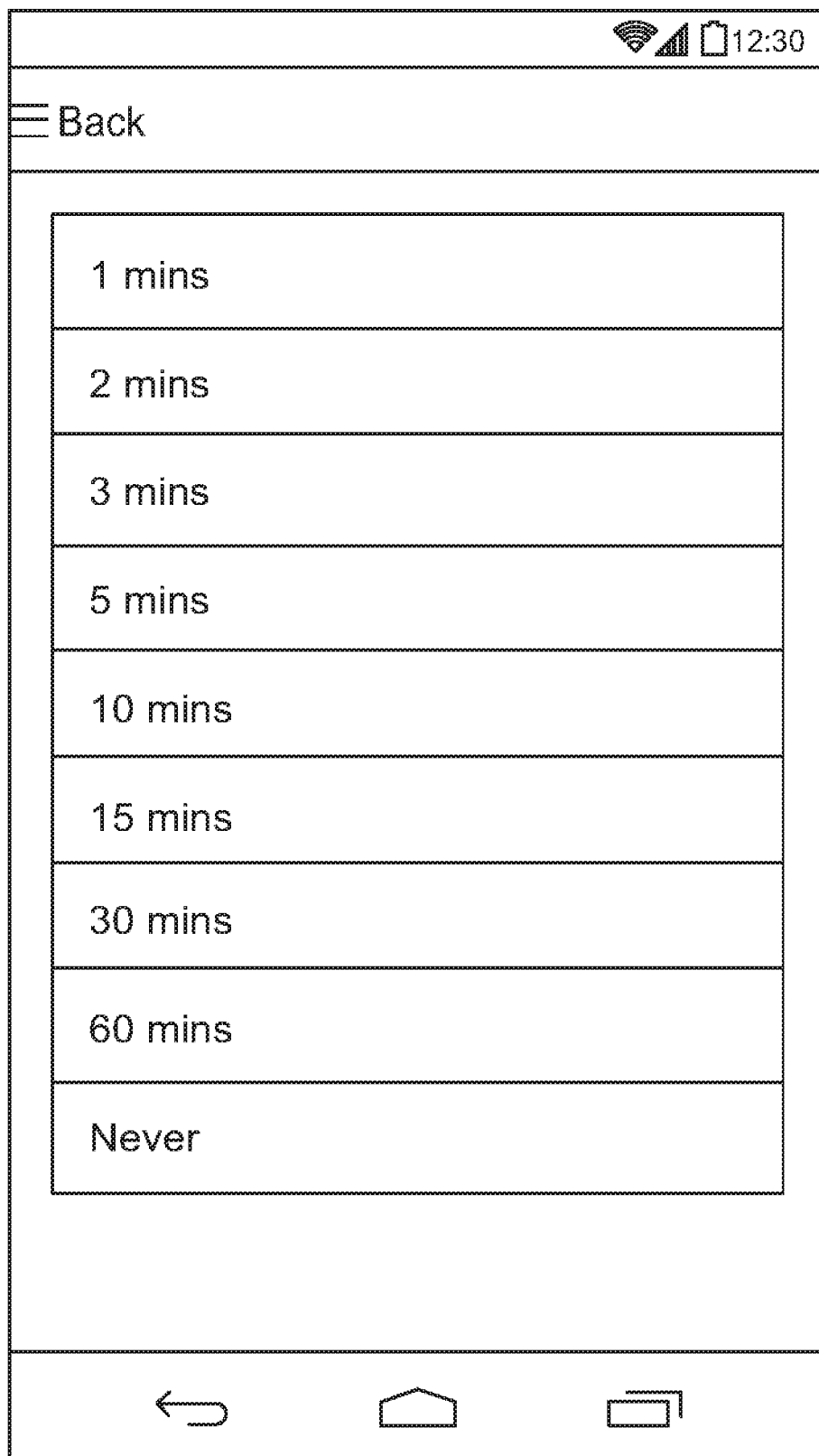
FIG. 78 is a diagram showing one embodiment of a shutoff selection screen.

FIGS. 67-78 illustrate embodiments of screens for setting various electronic device settings. FIG. 67 shows a device settings screen for a professional mode of operation. The device settings screen identifies current settings of the electronic device, including identity of the stethoscope to which the electronic device is paired, a mode of operation (which is "professional"), a gain, an automatic sleep time after which the stethoscope will go into a sleep mode or energy saving state, and an automatic shutdown time after which the stethoscope will turn off or go into OFF mode. FIG. 68 shows a device settings screen for a general mode of operation. The device settings screen identifies current settings of the electronic device, including identity of the stethoscope to which the electronic device is paired, a mode of operation (which is "general"), a gain, and an automatic sleep time after which the stethoscope will go into a sleep mode or energy saving state. FIG. 69 shows a device settings screen for a teacher mode of operation. The device settings screen identifies current settings of the electronic device, including identity of the stethoscope to which the electronic device is paired and whether automatic linking to student stethoscopes is allowed. FIG. 70 shows the device settings screen of FIG. 69 after six student stethoscopes have been linked to the stethoscope. FIG. 71 shows a device settings screen for a student mode of operation. The device settings screen identifies current settings of the electronic device, including identity of the stethoscope to which the electronic device is paired, identity of the teacher stethoscope to which the electronic device is paired, and whether the teacher's stethoscope is set as a favorite. FIG. 72 shows a stethoscope settings screen that allows the stethoscope linked to the electronic device to be unlinked (disconnected), to be turned off, to go to sleep, and to be renamed. FIG. 73 shows a mode selection screen that allows selection of whether to run the app in general, professional, teacher, or student mode. FIG. 74 shows the mode selection screen of FIG. 73 with professional mode selected. FIG. 75 shows a linked devices screen that identifies all stethoscopes linked with the electronic device. FIG. 76 shows another linked devices screen that indicates which of the linked stethoscopes of FIG. 75 are linked to one another, e.g., "my stethoscope" and "Nano stethoscope" being linked together and "Teacher stethoscope" and "Student" being linked together. FIG. 77 shows a sleep selection screen that allows the user to select the amount of time that elapses before the stethoscope sleeps. FIG. 78 shows a shutoff selection screen that allows the user to select the amount of time that elapses before the stethoscope shuts off.

Figure 79:
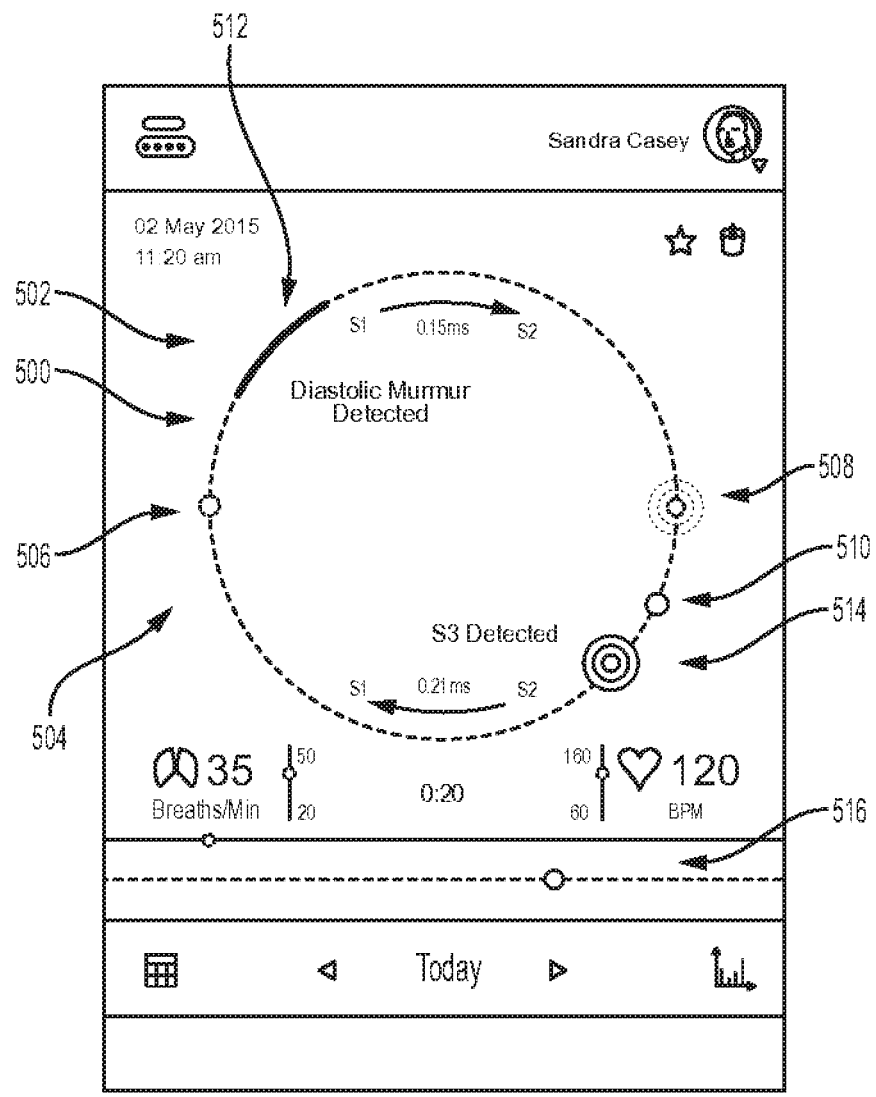
FIG. 79 is a diagram showing another embodiment of a cardiology information screen.

FIG. 79 shows one embodiment of a screen including cardiovascular information that can be gathered using a stethoscope (e.g., one of the stethoscopes described herein). The screen in this illustrated embodiment includes a "circle display" 500 providing real time cardiac data. A top hemisphere 502 of the circle display 500 can represent diastole cardiovascular information, and a bottom hemisphere 504 of the circle display 500 can represent systole cardiovascular information.

The circle display 500 can have statically displayed thereon S1 and S2 marks 506, 508 that represent a start of S1 and S2, respectively. Distance along the circle display 500 between the S1 and S2 marks 506, 508 can define the top and bottom hemispheres 502, 504. The S1 and S2 marks 506, 508 can be in a color that is different from a color of the line defining the circle display 500, which may facilitate quick visualization of the marks 506, 508. The S1 and S2 marks 506, 508 are each a same color in this illustrated embodiment.

A playhead (also referred to herein as a "marker") 510 can be configured to traverse around the circle display 500 in sync with the heart beat sound being detected by the stethoscope. This traversal can be similar to the spinning one or more lights that can spin around the stethoscope in a track-like pattern. The playhead 510 moves clockwise in this illustrated embodiment, but the playhead 510 can move counterclockwise in other embodiments. The playhead 510 includes a dot in this illustrated embodiment but can have other configurations, e.g., a square, an "x," a heart shape, etc. A one of the S1 and S2 marks 506, 508 to which the playhead 510 is currently closest can be focused, which may help facilitate quick visual identification of where the sound being gathered is in the patient's heart beat cycle. The S2 mark 508 is focuses in the form of a flared point in FIG. 79 since the playhead 510 is closer to S2 than S1. The playhead 510 can be in a color that is different from a color of the S1 and S2 marks 506, 508 and from a color of the line defining the circumference of the circle display 500, which may facilitate quick visualization of the playhead 510.

Each detected possible anomaly can be reflected with a symbol, mark, line, etc. (generally referred to herein as a "mark") on the circle display 500 at a point in time during a heartbeat cycle the abnormally detected sound was detected by where the mark is located around the circle display 500, e.g., at which point(s) during diastole and/or at which point(s) during systole the detected possible anomaly occurred. The timing of the abnormally detected sound may thus be easily identified through simple visual inspection of the screen. The mark can be configured to reflect a duration of the abnormally detected sound, for example by how long the mark extends around the line defining the circle display 500. By reflecting the length of the possible anomaly, the mark can indicate whether the abnormal sound was detected during diastole, during systole, or during both diastole and systole such that length of the abnormally detected sound can be easily identified through simple visual inspection of the screen. The mark can be configured to reflect a force or grade of the abnormally detected sound, for example by the thickness or darkness of the mark, with thicker marks indicating a higher force or grade and darker marks indicating a higher force or grade. The mark can be in a color that is different from a color of the playhead 510, from a color of the SI and S2 marks 506, 508, and from a color of the line defining the circumference of the circle display 500, which may facilitate quick visualization of the mark and, thus, the potential anomaly. In this illustrated embodiment, the circle display 500 has a first mark 512 thereon indicating a first possible anomaly and a second mark 514 thereon indicating a second possible anomaly. The first mark 512 is in the form of a line extending along the line that defines the circle display 500, with a length of the first mark 512 indicating a duration of the anomaly. If the first mark 512 repeatedly shows as the playhead 510 traverses over this portion of the circle display's line, the first mark 512 is more likely to indicate an actual anomaly such as a murmur. The second mark 514 is in the form of a dot at a discrete point around the circle display 500 indicating that possible anomaly was detected at a Specific point in time during the heart beat and is thus likely an additionally detected heart sound or S3, S4, etc. sound.

The circle display 500 can include thereon known pathologies of the subject. For example, if the subject is known to have a murmur or additional heart sound, the murmur or additional heart sound can be represented on the circle display 500 with a mark. If a mark appears on the circle display 500 indicative of a detected possible anomaly at the same location as the known pathology mark, this information may help a medical professional understand that the detected possible anomaly is likely real and is likely already considered in the subject's treatment plan.

The screen can include a baseline 516 that separates systolic and diastolic murmurs. A murmur below the line 516 can indicate a systole murmur, and a murmur above the line 516 can indicate a diastolic murmur.

The screen can provide an indication of a length of detected diastolic action (0.15 ms in this illustrated embodiment) and an indication of a length of detected systolic action (0.21 ms in this illustrated embodiment). The screen can provide other current status information, such as current heart rate (120 bpm in this illustrated embodiment), breaths per minute (35 breaths/minute in this illustrated embodiment), date, time, subject name and/or other identification, etc. The screen can provide historical data for the subject, directly or via selection icon, such as vital sign history for one or more vital signs, etc.

The screen displaying cardiovascular information can similarly display respiratory information that can be gathered using the stethoscope. The diastole cardiovascular information in the top hemisphere 502 of the circle display 500 can be replaced by inspiration respiratory information and the systole cardiovascular information in the bottom hemisphere 504 of the circle display 500 can be replaced by expiration respiratory information. Detected anomalies in respiration (e.g., wheezes, crackles, consolidation, fluid build-up, etc.) and known respiratory pathologies can be marked on the circle display 500 similar to that discussed above regarding the marks for the cardiac anomalies.

Figure 80:
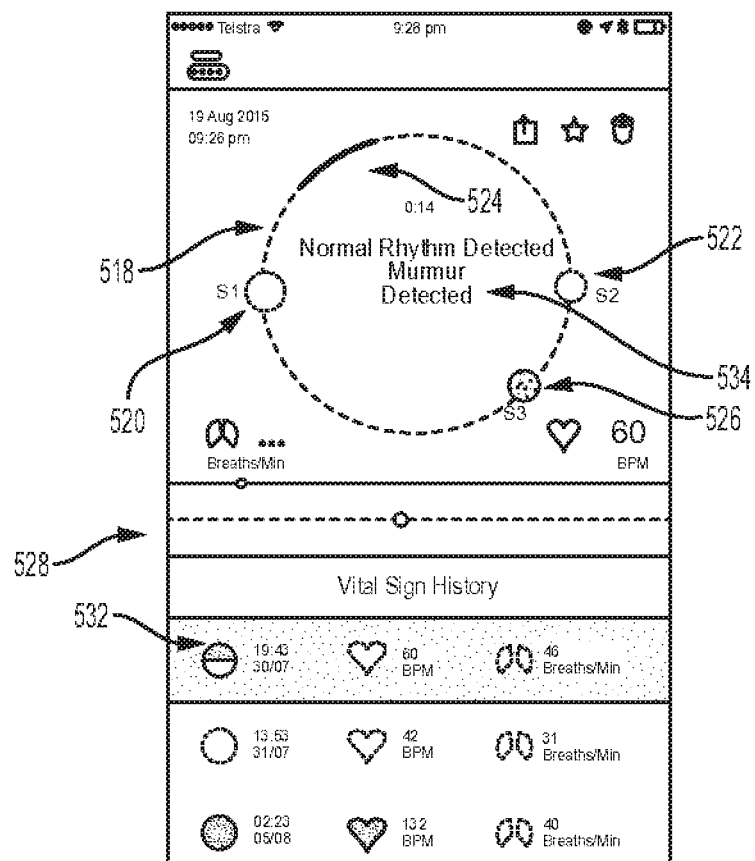
FIG. 80 is a diagram showing yet another embodiment of a cardiology information screen.

FIG. 80 shows another embodiment of a screen including cardiovascular information that can be gathered using a stethoscope and provided in real time. The screen of FIG. 80 can generally be configured and used similar to that of the screen of FIG. 79, e.g., can include a "circle display" 518, a playhead (not shown), an SI mark 520, an S2 mark 522, a possible anomaly mark 524, a known pathology mark 526, a baseline 528, current status information, and historical data. The historical data in this illustrated embodiment includes vital sign history for the subject for each of a plurality of previously recorded sounds. The vital sign history can provide coded information that may facilitate easy identification of past subject conditions. For example, as in this illustrated embodiment, a circle symbol representative of the circle display 518 can indicate with a solid circle that anomalies were detected in both of the systolic and diastolic phases, with a circle outline that no anomalies were detected in either of the systolic and diastolic phases, and with a circle 532 with one hemisphere shaded that an anomaly was detected in that shaded hemisphere phase (systolic in this illustrated embodiment). For another example, a color of a heart symbol representative of heart rate can indicate a range of the heart rate, e.g., a first color for a heart rate of 40-70 bpm, a second color for a heart rate of 70-120 bpm, and a third color for a heart rate of 120-180 bpm. For yet another example, a color of a lung symbol representative of breathing rate can indicate a range of the breathing rate.

As shown in this illustrated embodiment, the screen including cardiovascular information can include text summarizing the heart cycle status, which may help facilitate interpretation of the display. The text in this illustrated embodiment indicates rhythm status (normal) and abnormality detection status (murmur detected).

Figure 81:
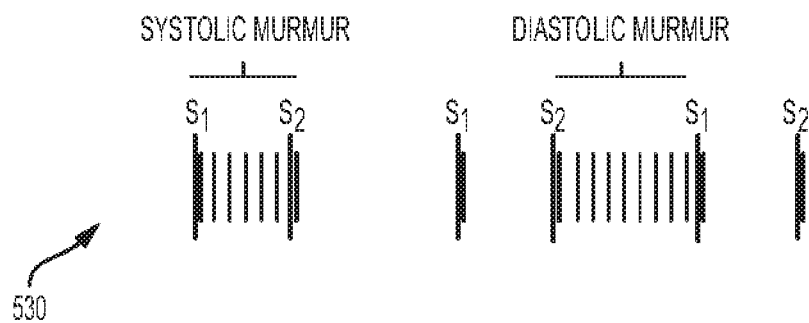
FIG. 81 is a diagram showing one embodiment of a grid for the screen of FIG. 80.

FIG. 81 shows a grid 530 representative of the possible anomaly mark 524 of FIG. 80 and representative of the known pathology mark 526 of FIG. 80. The grid 530 can be displayed on a screen, as discussed above, either the same screen as the circle display 518 or a different screen.

Figure 82:
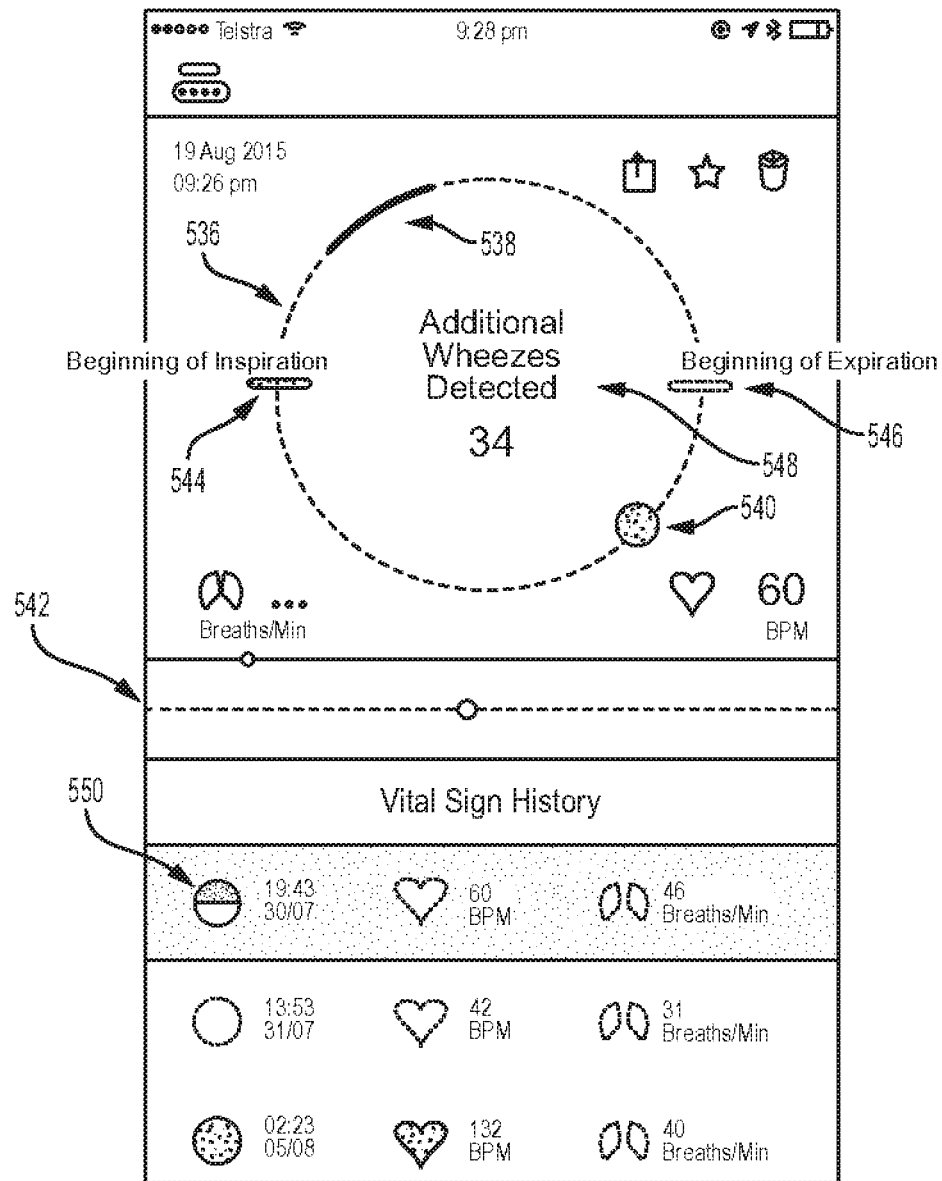
FIG. 82 is a diagram showing another embodiment of a respiratory information screen.

FIG. 82 shows one embodiment of a screen including respiratory information that can be gathered using a stethoscope and provided in real time. The screen of FIG. 82 can generally be configured and used similar to that of the screen of FIG. 79, e.g., can include a "circle display" 536, a playhead (not shown), a possible anomaly mark 538, a known pathology mark 540, a baseline 542, summarizing text 548, current status information, and historical data (which in this illustrated embodiment includes vital sign history similar to that of FIG. 80). In this illustrated embodiment, the vital sign history includes a circle 550 with one hemisphere shaded that an anomaly was detected in that shaded hemisphere phase (inspiration in this illustrated embodiment). Instead of including SI and S2 marks, the circle display 536 can include a beginning of inspiration mark 544 and a beginning of expiation mark 546. The mark for possible anomalies and known pathologies can be configured to reflect a timing or strength of the detected respiration sound, for example by the thickness or darkness of the mark, with thicker marks indicating a higher timing or strength and darker marks indicating a higher timing or strength. The marks can be configured to reflect a duration of the abnormally detected sound, as discussed above.

Figure 83:
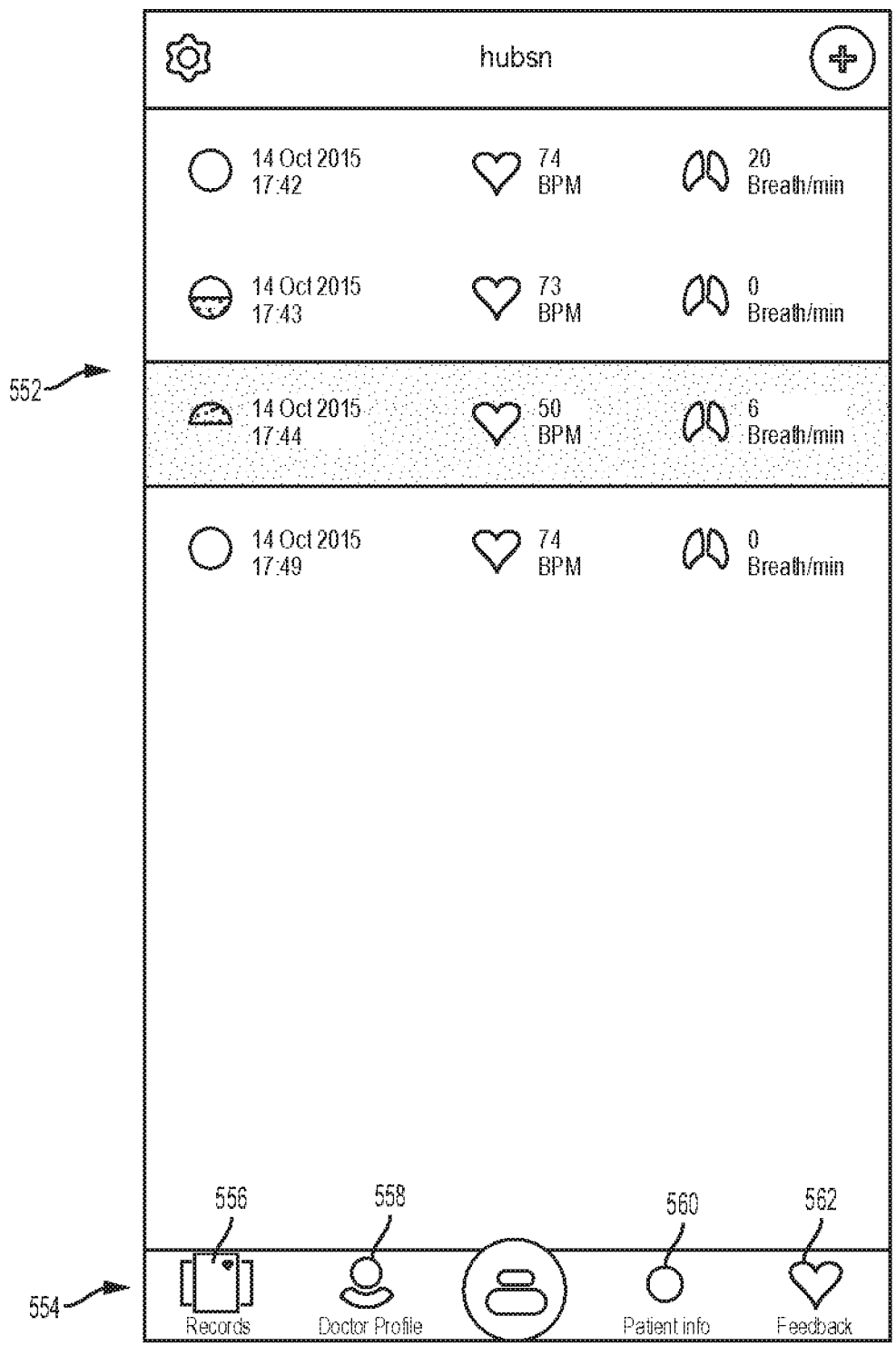
FIG. 83 is a showing one embodiment of a historical data screen.

FIG. 83 shows one embodiment of a screen including historical data 552, which in this illustrated embodiment includes vital sign history for a subject for each of a plurality of previously recorded sounds. The vital sign history can include information similar to that discussed above regarding the screen of FIG. 80, e.g., with circle symbols, heart symbols, and lung symbols.

As shown in this illustrated embodiment, the screen including historical data 552, or any other screen described herein, can include a data selection menu 554. The data selection menu 554 can be configured to allow a user to select which type of data to currently show on the electronic device including the display showing the screen. The data selection menu 554 can be present on or available through any screen, which may facilitate a user's selection of different data to view at any time during or after use of a stethoscope. For example, enabling the user to quickly access the user's vital sign history may help a medical professional easily and quickly identify trends and/or anomalies. The data selection menu 554 can include any number of data view options, which in this illustrated embodiment include selectable icons with identifying text. As in this illustrated embodiment, the data selection menu 554 can include an option 556 to view the historical data 552, an option 558 to view doctor profiles of one or more doctors, an option 560 to view information about the subject, and an option 562 to provide feedback.

FIG. 84 shows another embodiment of a recording detail screen. The recording detail screen of FIG. 84 can generally be configured and used similar to the recording detail screen discussed above with respect to FIG. 52. In this illustrated embodiment, the recording detail screen shows cardiovascular information similar to that discussed above regarding the screen of FIG. 80, e.g., can include a "circle display" 564, an SI mark 566, an S2 mark 568, a known pathology mark (not shown), a baseline 570, and current status information. The recording detail screen of FIG. 84 is shown before recording has begun, e.g., before a start button 572 has been selected, so the screen does not yet include a playhead or any possible anomaly marks.

The stethoscopes described herein can have an on-board computer system. The external electronic devices described herein as being configured to link to a stethoscope can each include a computer system.

Figure 85:
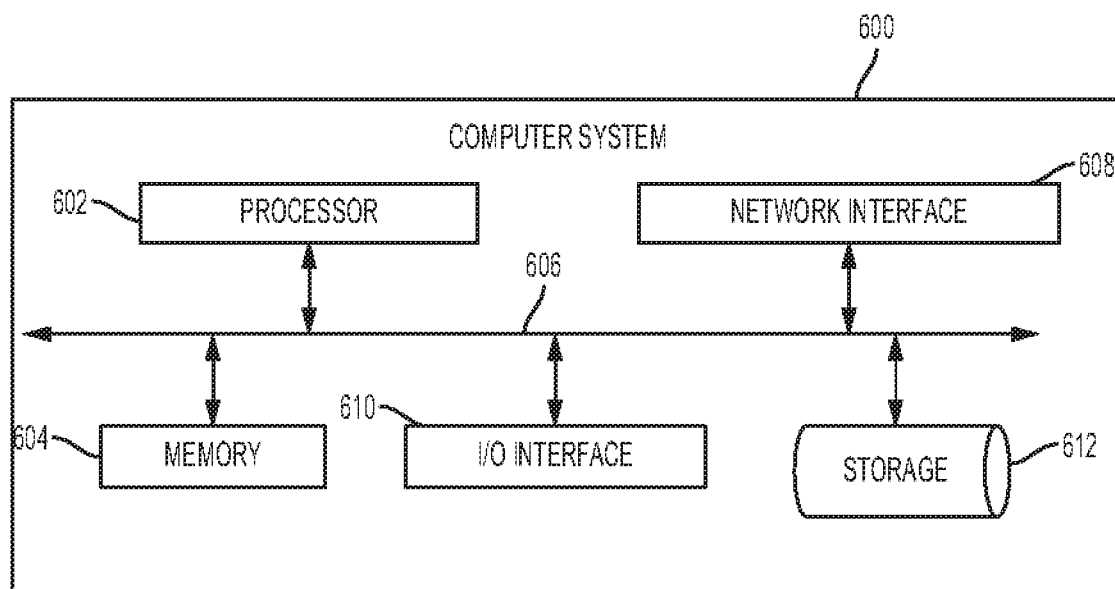
FIG. 85 is a schematic diagram of one embodiment of a computer system.

FIG. 85 illustrates one exemplary embodiment of a computer system 600. As shown, the computer system 600 can include one or more processors 602 which can control the operation of the computer system 600. The processor(s) 602 can include any type of microprocessor or central processing unit (CPU), including programmable general-purpose or special-purpose microprocessors and/or any one of a variety of proprietary or commercially available single or multi-processor systems. The computer system 600 can also include one or more memories 604, which can provide temporary storage for code to be executed by the processor(s) 602 or for data acquired from one or more users, storage devices, and/or databases. The memory 604 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 600 can be coupled to a bus system 606. The illustrated bus system 606 is an abstraction that represents any one or more separate physical busses, communication lines/interfaces, and/or multi-drop or point-to-point connections, connected by appropriate bridges, adapters, and/or controllers. The computer system 600 can also include one or more network interface(s) 608, one or more input/output (I/O) interface(s) 610, and one or more storage device(s) 612.

The network interface(s) 608 can enable the computer system 600 to communicate with remote devices, e.g., other computer systems, over a network, and can be, for example, remote desktop connection interfaces, Ethernet adapters, and/or other local area network (LAN) adapters. The I/O interface(s) 610 can include one or more interface components to connect the computer system 600 with other electronic equipment. For example, the I/O interface(s) 610 can include high speed data ports, such as USB ports, 1394 ports, Wi-Fi, Bluetooth, etc. Additionally, the computer system 600 can be accessible to a human user, and thus the I/O interface(s) 610 can include displays, speakers, keyboards, pointing devices, and/or various other video, audio, or alphanumeric interfaces. The storage device(s) 612 can include any conventional medium for storing data in a non-volatile and/or non-transient manner. The storage device(s) 612 can thus include a memory that holds data and/or instructions in a persistent state, i.e., the value is retained despite interruption of power to the computer system 600. The storage device(s) 612 can include one or more hard disk drives, flash drives, USB drives, optical drives, various media cards, diskettes, compact discs, and/or any combination thereof and can be directly connected to the computer system 600 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 85 can be some or all of the elements of a single physical machine. In addition, not all of the illustrated elements need to be located on or in the same physical machine, at least in the case of external electronic devices. Exemplary computer systems include conventional desktop computers, workstations, minicomputers, laptop computers, tablet computers, personal digital assistants (PDAs), mobile phones, and the like.

In an exemplary embodiment, the computer system 600 can be provided as a single unit, e.g., as a single server, as a single tower, contained within a single housing, etc. Systems and methods can thus be provided as a singular unit configured to display the various user interfaces and capture the data described herein. The singular unit can be modular such that various aspects thereof can be swapped in and out as needed for, e.g., upgrade, replacement, maintenance, etc., without interrupting functionality of any other aspects of the system. The singular unit can thus also be scalable with the ability to be added to as additional functionality is desired and/or improved upon.

A computer system can also include any of a variety of other software and/or hardware components, including by way of example, operating systems and database management systems. Although an exemplary computer system is depicted and described herein, it will be appreciated that this is for sake of generality and convenience. In other embodiments, the computer system may differ in architecture and operation from that shown and described here.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A digital stethoscope system configured to (i) record environmental data, and (ii) provide training data to a machine learning or AI-based system, in which the training data includes environmental data that captures a value of environmental variables detected by an electronic device at a time measurements of subject vital signs were made by a digital stethoscope device, in which the stethoscope system infers or generates a subject's breathing rate from heart rate or heart rate variability data determined by the stethoscope system, to enable the effect of the environmental data on the subject's breathing rate, and/or other vital sign data to be taken into account.

2. The system of claim 1 in which the system records one or more of: heart data, lung data, ECG/EKG data.

3. The system of claim 1 in which the system includes a processing sub-system programmed to analyse or classify data measured by the system and to identify anomalies from that data and normal organ functioning from that data.

4. The system of claim 1 in which the system detects and records environmental data, time stamped with subject data including one or more of heart data, ECG/EKG data, lung health data.

5. The system of claim 1 in which an environmental data is subject location data.

6. The system of claim 1 in which an environmental data is altitude data.

7. The system of claim 1 in which an environmental data is ambient temperature.

8. The system of claim 1 in which an environmental data is pollen count.

9. The system of claim 1 in which an environmental data is UV index.

10. The system of claim 1 in which an environmental data is wind speed.

11. The system of claim 1 in which an environmental data is wind direction.

12. The system of claim 1 in which an environmental data is humidity.

13. The system of claim 1 in which an environmental data is pollution index.

14. The system of claim 1 in which an environmental data is altitude.

15. The system of claim 1 in which the system includes a body that is placed on a subject, and in which the body includes an integral ECG/EKG sensor.

16. The system of claim 1 in which the system includes a body that is placed on a subject and a visual display.

17. The system of claim 16 in which the visual display is integral to the body.

18. The system of claim 16 in which the visual display is separate from the body.

19. The system of claim 16 in which the visual display is an application on a connected personal device, such as a smartphone or tablet or watch.

20. The digital stethoscope system of claim 1 in which the recorded environmental data has been time stamped and time matched to the measurements of the subject vital sign made by the digital stethoscope system.

21. The digital stethoscope system of claim 1 in which the training data includes time stamped vital sign data.

22. The digital stethoscope system of claim 1 in which the training data includes time stamped breathing rate data.

23. The digital stethoscope system of claim 1 in which the stethoscope system detects and records environmental data.

24. The digital stethoscope system of claim 1 in which the digital stethoscope system is further configured to determine a subject's breathing condition, such as asthma or pneumonia.

25. A method of providing training data to a machine learning or AI based-system using a digital stethoscope system, the method comprising the steps of:
 (i) measuring subject vital sign data by the digital stethoscope system;
 (ii) recording environmental data;
 (iii) capturing a value of the environmental data detected by an electronic device at a time measurements of subject vital signs were made by a digital stethoscope device;
 (iv) providing training data to the machine learning or AI-based system in which the training data includes environmental data that captures the value of the environmental data detected by the electronic device at the time measurements of subject vital signs were made by the digital stethoscope device;
 in which the stethoscope system infers or generates a subject's breathing rate from heart rate or heart rate variability data determined by the stethoscope system, to enable the effect of the environmental data on the subject's breathing rate, and/or other vital sign data to be taken into account.

* * * * *